United States Patent
Simmen et al.

(10) Patent No.: US 7,666,834 B2
(45) Date of Patent: Feb. 23, 2010

(54) MACROCYCLIC INHIBITORS OF HEPATITIS C VIRUS

(75) Inventors: Kenneth Alan Simmen, Tervuren (BE); Herman Augustinus De Kock, Arendonk (BE); Pierre Jean-Marie Bernard Raboisson, Sterrebeek (BE); Carl Erik Daniel Jönsson, Huddinge (SE); Karl Magnus Nilsson, Huddinge (SE); Bengt Bertil Samuelsson, Huddinge (SE); Åsa Annica Kristina Rosenquist, Huddinge (SE); Dmitry Antonov, Huddinge (SE); Lourdes Salvador Odén, Huddinge (SE); Susana Ayesa Alvarez, Huddinge (SE); Björn Olof Classon, Huddinge (SE)

(73) Assignee: Tibotec Pharmaceuticals Ltd., Little Island, Co. Cork (IE)

( * ) Notice: Subject to any disclaimer, the term of this patent is extended or adjusted under 35 U.S.C. 154(b) by 78 days.

(21) Appl. No.: 11/995,827

(22) PCT Filed: Jul. 28, 2006

(86) PCT No.: PCT/EP2006/064816

§ 371 (c)(1),
(2), (4) Date: Jan. 16, 2008

(87) PCT Pub. No.: WO2007/014922

PCT Pub. Date: Feb. 8, 2007

(65) Prior Publication Data

US 2009/0105302 A1    Apr. 23, 2009

(30) Foreign Application Priority Data

Jul. 29, 2005 (EP) .................. 05107070
Feb. 3, 2006 (EP) .................. 06101279

(51) Int. Cl.
*A61K 38/00* (2006.01)
(52) U.S. Cl. ......................................... 514/9
(58) Field of Classification Search ................ None
See application file for complete search history.

(56) References Cited

U.S. PATENT DOCUMENTS

| | | | |
|---|---|---|---|
| 5,484,801 A | 1/1996 | Al-Razzak | |
| 5,807,876 A | 9/1998 | Armistead et al. | |
| 5,948,436 A | 9/1999 | Al-Razzak et al. | |

(Continued)

FOREIGN PATENT DOCUMENTS

| | | |
|---|---|---|
| WO | WO 94/14436 | 7/1994 |
| WO | WO 95/07696 | 3/1995 |

(Continued)

OTHER PUBLICATIONS

Aresta, M. et al., "Mechanistic Studies on the Role of Carbon Dioxide in the Syssnthesis of Methylcarbamates from Amines and Dimethylcarbonate in the Presence of $Co_2$" Tetrahedron, 1991, 47, 9489.

(Continued)

*Primary Examiner*—Cecilia Tsang
*Assistant Examiner*—Marcela M Cordero Garcia

(57) ABSTRACT

Inhibitors of HCV replication of formula (I)

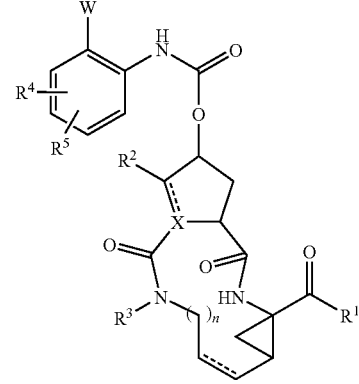

(I)

and the N-oxides, salts, or stereoisomers thereof, wherein
each dashed line (represented by - - - - -) represents an optional double bond;
X is N, CH and where X bears a double bond it is C;
$R^1$ is —$OR^6$, —NH—$SO_2R^7$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, or $C_{3-7}$cycloalkyl;
n is 3, 4, 5, or 6;
$R^4$ and $R^5$ independently from one another are hydrogen, halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, $C_{1-6}$alkoxy-carbonyl, amino, azido, mercapto, $C_{1-6}$alkylthio, polyhalo$C_{1-6}$alkyl, aryl or Het;
W is aryl or Het;
$R^6$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
$R^7$ is aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
aryl is phenyl or naphthyl, each optionally substituted with 1-3 substituents;
Het is a 5 or 6 membered saturated, partially unsaturated or completely unsaturated heterocyclic ring containing 1-4 heteroatoms each independently selected from N, O or S, and optionally substituted with 1-3 substituents;
pharmaceutical compositions containing compounds (I) and processes for preparing compounds (I). Bioavailable combinations of the inhibitors of HCV of formula (I) with ritonavir are also provided.

12 Claims, No Drawings

U.S. PATENT DOCUMENTS

| | | | |
|---|---|---|---|
| 6,037,157 | A | 3/2000 | Norbeck et al. |
| 6,054,472 | A | 4/2000 | Armistead et al. |
| 6,344,465 | B1 | 2/2002 | Armistead et al. |
| 6,498,178 | B2 | 12/2002 | Stamos et al. |
| 7,125,845 | B2 * | 10/2006 | Wu et al. ................... 514/10 |
| 2005/0065073 | A1 * | 3/2005 | Wu et al. ................... 514/10 |
| 2009/0062311 | A1 * | 3/2009 | Simmen et al. .......... 514/258.1 |

FOREIGN PATENT DOCUMENTS

| | | |
|---|---|---|
| WO | WO 95/09614 | 4/1995 |
| WO | WO 97/40028 | 10/1997 |
| WO | WO 98/17679 | 4/1998 |
| WO | WO 9822496 | 5/1998 |
| WO | WO 98/40381 | 9/1998 |
| WO | WO 99/07734 | 2/1999 |
| WO | WO 00/09543 | 2/2000 |
| WO | WO 00/56331 | 9/2000 |
| WO | WO 00/59929 | 10/2000 |
| WO | WO 02/18369 | 3/2002 |
| WO | WO 03/087092 | 10/2003 |
| WO | WO 03/099274 A1 | 12/2003 |
| WO | WO 2004/072243 | 8/2004 |
| WO | WO 2005/010029 | 2/2005 |
| WO | WO 2005/037214 A2 | 4/2005 |
| WO | WO 2005/073195 | 8/2005 |
| WO | WO 2005/073216 | 8/2005 |
| WO | WO 2005/095403 A2 | 10/2005 |

OTHER PUBLICATIONS

Bodanszky, M., "Peptide Chemistry", 2$^{nd}$ Red.Ed., Springer-Verlag, Berlin, Germany (1993).

Dolby, et al., in J. Org. Chem. 36 (1971) 1277-1285.

Goodman and Gillman's "The Pharmacological Basis of Therapeutics" Eighth Edition, McGraw-Hill, Inc., Health Professions Division, p. 1-20 Title Page and Table of Conents.

Greene, "Protective Groups in Organic Chemistry", Wiley, John & Sons, New York (1999) and "The Peptides: Analysis, Synthesis, Biology", vol. 9, Academic Press, NY (1987) Title Page and Table of Contents.

Huang, et al., "Olefin Metathesis-Active Ruthenium Complexes Bearing a Nucleophilic Carbene Ligand" J.Am. Chem. Soc. 1999 121, p. 2674-2678.

Kingsbury, J., "A Recyclable Ru-Based Metathesis Catalyst", et al., J.Am. Chem. Soc. 1999, 121, p. 791-799.

Krieger, N., et al., "Enhancement of Hepatitis C Virus RNA Replication by Cell Culture-Adaptive Mutations", Journal of Virology, May 2001, pp. 4614-4624.

Lohmann, V., et al., "Replication of Subgenomic Hepatitis C Virus RNAs in a Hepatoma Cell Line", Science 285, 1999, pp. 110-113.

Miller, S., et al., "Application of Ring-Closing Metathesis to the Synthesis of Rigidified Amino Acids and Peptides", J.Am. Chem. Soc. 1996, 118, p. 9606-9614.

Rosenquist, A., et al. "Synthesis of Enantiomerically Pure trans-3,4-Substituted Cyclopentanois by Enzymatic Resolution", Acta Chem. Scand. 46 (1992) 1127-1129.

Yoshida, Y. et al., Y., et al. "Novel Synthesis of Carbamate Ester from Carbon Dioxide, Amines, and Alkyl Halides", Bull Chem. Soc., Japan 1989, 62, 1534.

* cited by examiner

MACROCYCLIC INHIBITORS OF HEPATITIS C VIRUS

CROSS REFERENCE TO RELATED APPLICATIONS

This application claims priority of the benefits of the filing of Patent Application Nos. EP 05107070.4 filed Jul. 29, 2005; EP 06101279.5 filed Feb. 3, 2006; and PCT/EP2006/064816 filed Jul. 28, 2006. The complete disclosures of the aforementioned related applications are hereby incorporated herein by reference for all purposes.

The present invention is concerned with macrocylic compounds having inhibitory activity on the replication of the hepatitis C virus (HCV). It further concerns compositions comprising these compounds as active ingredients as well as processes for preparing these compounds and compositions.

Hepatitis C virus is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO00/59929 and VX-950 disclosed in WO03/87092. A number of similar HCV protease inhibitors have also been disclosed in the academic and patent literature. It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168A and/or A156S. Accordingly, additional drugs with different resistance patterns are required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosage regimes.

There is a need for HCV inhibitors which may overcome the disadvantages of current HCV therapy such as side effects, limited efficacy, the emerging of resistance, and compliance failures.

WO05/037214 relates to macrocyclic carboxylic acids and acylsulfonamides as inhibitors of HCV replication, as well as pharmaceutical compositions, methods of treating a Hepatitis C virus infection and methods of treating liver fibrosis.

The present invention concerns HCV inhibitors which are superior in one or more of the following pharmacological related properties, i.e. potency, decreased cytotoxicity, improved pharmacokinetics, improved resistance profile, acceptable dosage and pill burden.

In addition, the compounds of the present invention have relatively low molecular weight and are easy to synthesize, starting from starting materials that are commercially available or readily available through art-known synthesis procedures.

The present invention concerns inhibitors of HCV replication, which can be represented by formula (I):

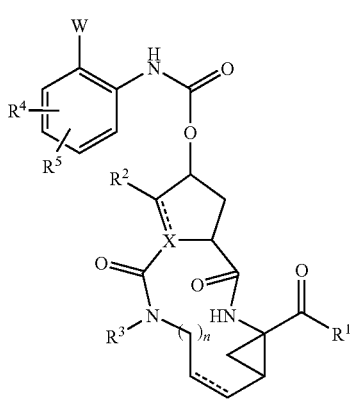

and the N-oxides, salts, and stereoisomers thereof, wherein each dashed line (represented by - - - - -) represents an optional double bond;
X is N, CH and where X bears a double bond it is C;
$R^1$ is —$OR^6$, —NH—$SO_2R^7$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, or $C_{3-7}$cycloalkyl;
n is 3, 4, 5, or 6;
$R^4$ and $R^5$ independently from one another are hydrogen, halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, $C_{1-6}$alkoxy-carbonyl, amino, azido, mercapto, $C_{1-6}$alkyl thio, polyhalo$C_{1-6}$alkyl, aryl or Het;
W is aryl or Het;
$R^6$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
$R^7$ is aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
aryl as a group or part of a group is phenyl or naphthyl, each of which may be optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$ alkyl, $C_{1-6}$alkylcarbonyl, amino, mono- or di$C_{1-6}$alkylamino, azido, mercapto, polyhalo$C_{1-6}$alkyl, polyhalo$C_{1-6}$ alkoxy, $C_{3-7}$cycloalkyl, pyrrolidinyl, piperidinyl, piperazinyl, 4-$C_{1-6}$alkyl-piperazinyl, 4-$C_{1-6}$alkylcarbonyl-piperazinyl, and morpholinyl; wherein the morpholinyl and piperidinyl groups may be optionally substituted with one or with two $C_{1-6}$alkyl radicals;
Het as a group or part of a group is a 5 or 6 membered saturated, partially unsaturated or completely unsaturated heterocyclic ring containing 1 to 4 heteroatoms each independently selected from nitrogen, oxygen and sulfur, and being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di-$C_{1-6}$alkylamino, azido, mercapto, polyhalo$C_{1-6}$alkyl, polyhalo$C_{1-6}$alkoxy, $C_{3-7}$cycloalkyl, pyrrolidinyl, piperidinyl, piperazinyl, 4-$C_{1-6}$alkyl-piperazinyl, 4-$C_{1-6}$alkylcarbonyl-piperazinyl, and morpholinyl; wherein the morpholinyl and piperidinyl groups may be optionally substituted with one or with two $C_{1-6}$alkyl radicals.

The invention further relates to methods for the preparation of the compounds of formula (I), the N-oxides, addition salts, quaternary amines, metal complexes, and stereochemically isomeric forms thereof, their intermediates, and the use of the intermediates in the preparation of the compounds of formula (I).

The invention relates to the compounds of formula (I) per se, the N-oxides, addition salts, quaternary amines, metal complexes, and stereochemically isomeric forms thereof, for use as a medicament. The invention further relates to pharmaceutical compositions comprising the aforementioned compounds for administration to a subject suffering from HCV infection. The pharmaceutical compositions may comprise combinations of the aforementioned compounds with other anti-HCV agents.

The invention also relates to the use of a compound of formula (I), or a N-oxide, addition salt, quaternary amine, metal complex, or stereochemically isomeric forms thereof, for the manufacture of a medicament for inhibiting HCV replication. Or the invention relates to a method of inhibiting HCV replication in a warm-blooded animal said method comprising the administration of an effective amount of a compound of formula (I), or a N-oxide, addition salt, quaternary amine, metal complex, or stereochemically isomeric forms thereof.

As used in the foregoing and hereinafter, the following definitions apply unless otherwise noted.

The term halo is generic to fluoro, chloro, bromo and iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$ alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{1-16}$alkanediyl defines bivalent straight and branched chain saturated hydrocarbon radicals having from 1 to 6 carbon atoms such as, for example, methylene, ethylene, 1,3-propanediyl, 1,4-butanediyl, 1,2-propanediyl, 2,3-butanediyl, 1,5-pentanediyl, 1,6-hexanediyl and the like. Of interest amongst $C_{1-6}$alkanediyl is $C_{1-4}$alkanediyl.

$C_{1-6}$alkoxy means $C_{1-6}$alkyloxy wherein $C_{1-6}$alkyl is as defined above.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

The radical Het is a heterocycle as specified in this specification and claims. Examples of Het comprise, for example, pyrrolidinyl, piperidinyl, morpholinyl, thiomorpholinyl, piperazinyl, pyrrolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, and the like. Of interest amongst the Het radicals are those which are non-saturated, in particular those having an aromatic character. Of further interest are those Het radicals having one or two nitrogens.

Each of the Het or W radicals mentioned in this and the following paragraphs may be optionally substituted with the number and kind of substituents mentioned in the definitions of the compounds of formula (I) or any of the subgroups of compounds of formula (I). Some of the Het or W radicals mentioned in this and the following paragraphs may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one. Where Het is piperazinyl, it preferably is substituted in its 4-position by a substituent linked to the 4-nitrogen with a carbon atom, e.g. 4-$C_{1-6}$alkyl, 4-polyhalo$C_{1-6}$alkyl, $C_{1-6}$alkoxy$C_{1-6}$alkyl, $C_{1-6}$alkylcarbonyl, $C_{3-7}$cycloalkyl.

Interesting Het radicals comprise, for example pyrrolidinyl, piperidinyl, morpholinyl, thiomorpholinyl, piperazinyl, pyrrolyl, pyrazolyl, imidazolyl, oxazolyl, isoxazolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, or any of such heterocycles condensed with a benzene ring, such as indolyl, indazolyl (in particular 1H-indazolyl), indolinyl, quinolinyl, tetrahydroquinolinyl (in particular 1,2,3,4-tetrahydroquinolinyl), isoquinolinyl, tetrahydroisoquinolinyl (in particular 1,2,3,4-tetrahydroisoquinolinyl), quinazolinyl, phthalazinyl, benzimidazolyl, benzoxazolyl, benzisoxazolyl, benzothiazolyl, benzoxadiazolyl, benzothiadiazolyl, benzofuranyl, benzothienyl.

The Het radicals pyrrolidinyl, piperidinyl, morpholinyl, thiomorpholinyl, piperazinyl, 4-substituted piperazinyl preferably are linked via their nitrogen atom (i.e. 1-pyrrolidinyl, 1-piperidinyl, 4-thiomorpholinyl, 4-morpholinyl, 1-piperazinyl, 4-substituted 1-piperazinyl).

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), each and any of the subgroups thereof, their prodrugs, N-oxides, addition salts, quaternary amines, metal complexes, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their N-oxides, salts, solvates, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The present invention is also intended to include prodrugs of the compounds of formula (I). The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

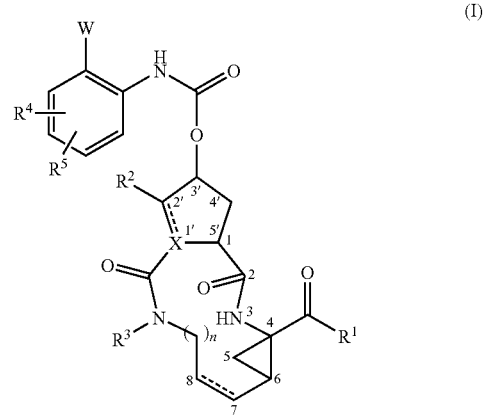

Asymmetric centers are present at positions 1, 4 and 6 of the macrocycle as well as at the carbon atom 3' in the 5-membered ring, carbon atom 2' when the $R^2$ substituent is $C_{1-6}$alkyl, and at carbon atom 1' when X is CH. Each of these asymmetric centers can occur in their R or S configuration.

The stereochemistry at position 1 preferably corresponds to that of an L-amino acid configuration, i.e. that of L-proline.

When X is CH, the 2 carbonyl groups substituted at positions 1' and 5' of the cyclopentane ring preferably are in a trans configuration. The carbonyl substituent at position 5' preferably is in that configuration that corresponds to an L-proline configuration. The carbonyl groups substituted at positions 1' and 5' preferably are as depicted below in the structure of the following formula

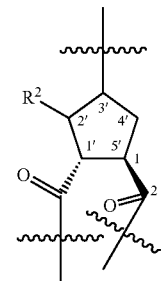

The compounds of formula (I) include a cyclopropyl group as represented in the structural fragment below:

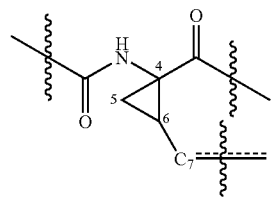

wherein $C_7$ represents the carbon at position 7 and carbons at position 4 and 6 are asymmetric carbon atoms of the cyclopropane ring.

Notwithstanding other possible asymmetric centers at other segments of the compounds of formula (I), the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

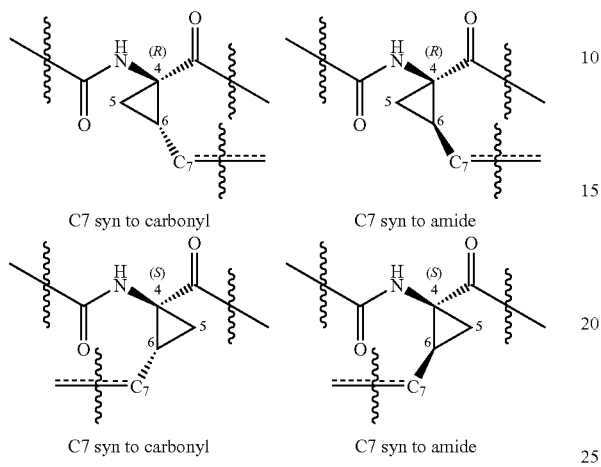

C7 syn to carbonyl  C7 syn to amide

C7 syn to carbonyl  C7 syn to amide

One embodiment concerns compounds of formula (I) wherein the carbon at position 7 is configured syn to the carbonyl. Another embodiment concerns compounds of formula (I) wherein the configuration at the carbon at position 4 is R. A specific subgroup of compounds of formula (I) are those wherein the carbon at position 7 is configured syn to the carbonyl and wherein the configuration at the carbon at position 4 is R.

The compounds of formula (I) may include a proline residue (when X is N) or a cyclopentyl or cyclopentenyl residue (when X is CH or C). Preferred are the compounds of formula (I) wherein the substituent at the 1 (or 5') position and the carbamate substituent at position 3' are in a trans configuration. Of particular interest are the compounds of formula (I) wherein position 1 has the configuration corresponding to L-proline and the carbamate substituent at position 3' is in a trans configuration in respect of position 1. Preferably the compounds of formula (I) have the stereochemistry as indicated in the structures of formulae (I-a) and (I-b) below:

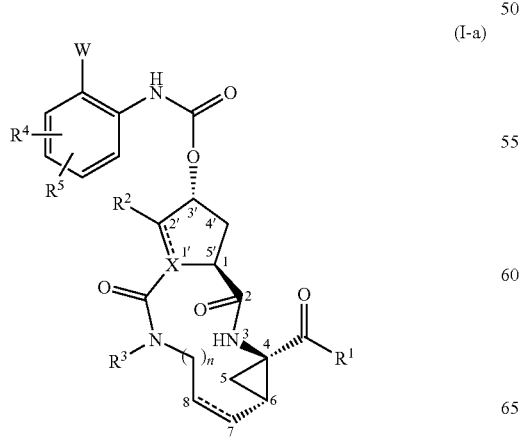

(I-a)

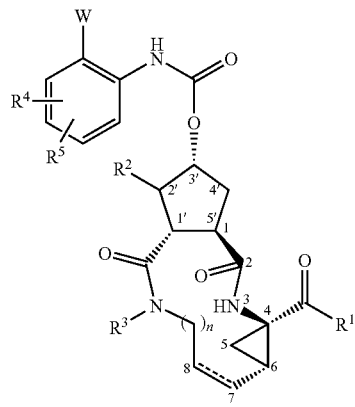

(I-b)

One embodiment of the present invention concerns compounds of formula (I) or of formula (I-a) or of any subgroup of compounds of formula (I), wherein one or more of the following conditions apply:

(a) $R^2$ is hydrogen;

(b) X is nitrogen;

(c) a double bond is present between carbon atoms 7 and 8.

One embodiment of the present invention concerns compounds of formula (I) or of formulae (I-a), (I-b), or of any subgroup of compounds of formula (I), wherein one or more of the following conditions apply:

(a) $R^2$ is hydrogen;

(b) X is CH;

(c) a double bond is present between carbon atoms 7 and 8.

Particular subgroups of compounds of formula (I) are those represented by the following structural formulae:

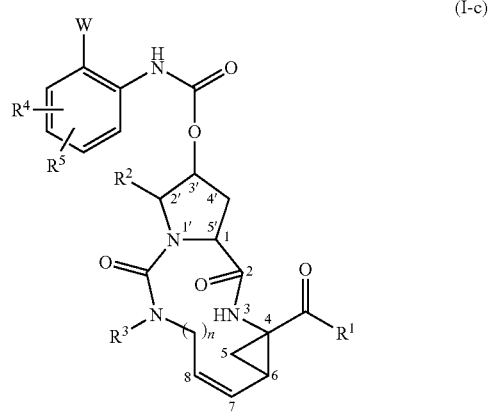

(I-c)

-continued

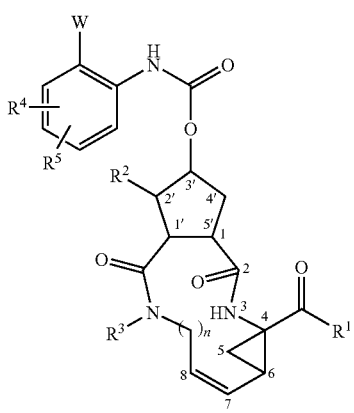
(I-d)

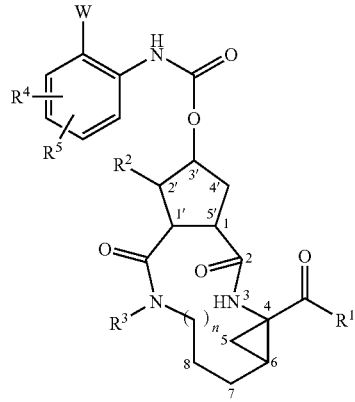
(I-g)

Amongst the compounds of formula (I-c) and (I-d), those having the stereochemical configuration of the compounds of formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c) and (I-d).

A double bond between carbon atoms 1' and 2' may be present in the compounds of formula (I), or in any subgroup of compounds of formula (I), as depicted in formula (I-e) below.

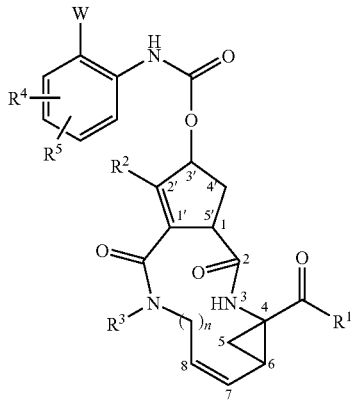
(I-e)

Yet another particular subgroup of compounds of formula (I) are those represented by the following structural formulae:

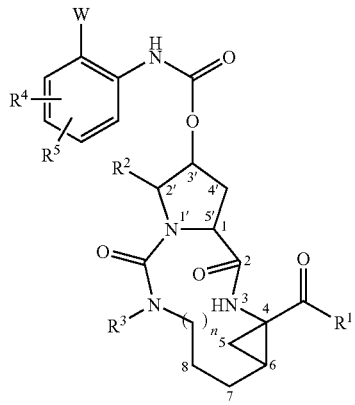
(I-f)

(I-h)

Amongst the compounds of formulae (I-f), (I-g) or (I-h), those having the stereochemical configuration of the compounds of formulae (I-a) and (I-b) are of particular interest.

In (I-a), (I-b), (I-c), (I-d), (I-e), (I-f), (I-g) and (I-h), where applicable, X, W, n, $R^1$, $R^2 R^3$, $R^4$ and $R^5$ are as specified in the definitions of the compounds of formula (I) or in any of the subgroups of compounds of formula (I) specified herein.

It is to be understood that the above defined subgroups of compounds of formulae (I-a), (I-b), (I-c), (I-d), (I-e), (I-f), (I-g) or (I-h), as well as any other subgroup defined herein, are meant to also comprise any prodrugs, N-oxides, addition salts, quaternary amines, metal complexes and stereochemically isomeric forms of such compounds.

When n is 2, the moiety —$CH_2$— bracketed by "n" corresponds to ethanediyl in the compounds of formula (I) or in any subgroup of compounds of formula (I). When n is 3, the moiety —$CH_2$— bracketed by "n" corresponds to propanediyl in the compounds of formula (I) or in any subgroup of compounds of formula (I). When n is 4, the moiety —$CH_2$— bracketed by "n" corresponds to butanediyl in the compounds of formula (I) or in any subgroup of compounds of formula (I). When n is 5, the moiety —$CH_2$— bracketed by "n" corresponds to pentanediyl in the compounds of formula (I) or in any subgroup of compounds of formula (I). When n is 6, the moiety —$CH_2$— bracketed by "n" corresponds to hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein (a) $R^1$ is —$OR^6$, in particular wherein $R^6$ is $C_{1-6}$alkyl, such as methyl, ethyl, or tert-butyl and most preferably where $R^6$ is hydrogen;
(b) $R^1$ is —$NHS(=O)_2R^7$, in particular wherein $R^7$ is $C_{1-6}$alkyl, $C_3$-$C_7$cycloalkyl, or aryl, e.g. wherein $R^7$ is methyl, cyclopropyl, or phenyl; or
(c) $R^1$ is —$NHS(=O)_2R^7$, in particular wherein $R^7$ is $C_{3-7}$cycloalkyl substituted with $C_{1-6}$alkyl, preferably wherein $R^7$ is cyclopropyl, cyclobutyl, cyclopentyl, or cyclohexyl, any of which is substituted with $C_{1-4}$alkyl, i.e. with methyl, ethyl, propyl, isopropyl, butyl, tert-butyl, or isobutyl.

Further embodiments of the invention are compounds of formula (I) or any of the subgroups of compounds of formula (I) wherein $R^1$ is —$NHS(=O)_2R^7$, in particular wherein $R^7$ is cyclopropyl substituted with $C_{1-4}$alkyl, i.e. with methyl, ethyl, propyl, or isopropyl.

Further embodiments of the invention are compounds of formula (I) or any of the subgroups of compounds of formula (I) wherein $R^1$ is —$NHS(=O)_2R^7$, in particular wherein $R^7$ is 1-methylcyclopropyl.

Further embodiments of the invention are compounds of formula (I) or any of the subgroups of compounds of formula (I) wherein (a) $R^2$ is hydrogen;
(b) $R^2$ is $C_{1-6}$alkyl, preferably methyl.

Embodiments of the invention are compounds of formula (I) or any of the subgroups of compounds of formula (I) wherein (a) X is N, C (X being linked via a double bond) or CH (X being linked via a single bond) and $R^2$ is hydrogen;
(b) X is C (X being linked via a double bond) and $R^2$ is $C_{1-6}$alkyl, preferably methyl.

Further embodiments of the invention are compounds of formula (I) or any of the subgroups of compounds of formula (I) wherein (a) $R^3$ is hydrogen;
(b) $R^3$ is $C_{1-6}$alkyl;
(c) $R^3$ is $C_{1-6}$alkoxy$C_{1-6}$alkyl or $C_{3-7}$cycloalkyl.

Preferred embodiments of the invention are compounds of formula (I) or any of the subgroups of compounds of formula (I) wherein $R^3$ is hydrogen, or $C_{1-6}$alkyl, more preferably hydrogen or methyl.

Embodiments of the invention are compounds of formula (I) or any of the subgroups of compounds of formula (I) wherein W is phenyl, naphthyl, furanyl, thienyl, pyrrolyl, pyrazolyl, imidazolyl, thiazolyl, triazolyl, tetrazolyl, pyridyl, pyridazinyl, pyrimidinyl, pyrrolidinyl, piperidinyl, or morpholinyl; all optionally substituted with one, two or three substituents selected from those mentioned in relation to aryl and Het in the definitions of the compounds of formula (I), or of any of the subgroups thereof.

Other subgroups of the compounds of formula (I) are those compounds of formula (I), or any subgroup of compounds of formula (I) specified herein, wherein W is phenyl, naphthyl (in particular naphth-1-yl, or naphth-2-yl), pyrrolyl (in particular pyrrol-1-yl), pyridyl (in particular 3-pyridyl), pyrimidinyl (in particular pyrimidin-4-yl), pyridazinyl (in particular pyridazin-3-yl and pyridazin-2-yl), 6-oxo-pyridazin-1-yl, triazolyl (in particular 1,2,3-triazolyl, 1,2,4-triazolyl, more in particular 1,2,3-triazol-2-yl, 1,2,4-triazol-3-yl), tetrazolyl (in particular tetrazol-1-yl, tetrazol-2-yl), pyrazolyl (in particular pyrazol-1-yl, pyrazol-3-yl), imidazolyl (in particular imidazol-1-yl, imidazol-2-yl), thiazolyl (in particular thiazol-2-yl), pyrrolidinyl (in particular pyrrolidin-1-yl), piperidinyl (in particular piperidin-1-yl), piperazinyl (in particular 1-piperazinyl), 4-$C_{1-6}$alkylpiperazinyl (in particular 4-$C_{1-6}$alkylpiperazin-1-yl, more in particular 4-methyl-piperazin-1-yl), furanyl (in particular furan-2-yl), thienyl (in particular thien-3-yl), morpholinyl (in particular morpholin-4-yl); all optionally substituted with one or two substituents selected from $C_{1-6}$alkyl, polyhalo$C_{1-6}$alkyl, or $C_{1-6}$alkoxycarbonyl.

Further subgroups of the compounds of formula (I) are those compounds of formula (I), or any subgroup of compounds of formula (I) specified herein, wherein W is thiazol-2-yl substituted with one or two $C_{1-6}$alkyl, such as methyl, ethyl, isopropyl or tert-butyl. Preferred subgroups of the compounds of formula (I) are those compounds of formula (I), or any subgroup of compounds of formula (I) specified herein, wherein W is selected from the following structures:

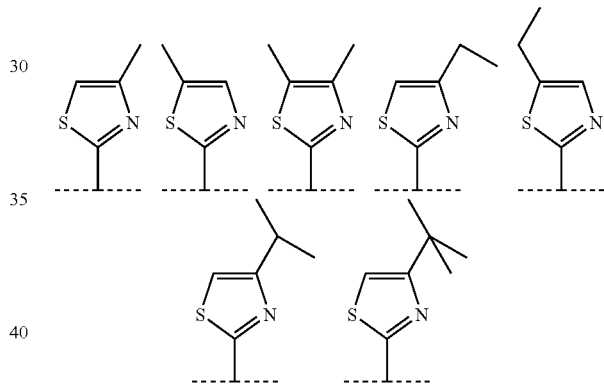

Embodiments of the invention are compounds of formula (I) or any of the subgroups of compounds of formula (I) wherein $R^4$ and $R^5$ independently from one another are hydrogen, halo, nitro, carboxyl, $C_{1-6}$alkyl, $C_{1-6}$alkoxy, $C_{1-6}$alkylcarbonyl, $C_{1-6}$alkoxy-carbonyl, $C_{1-6}$alkylthio, polyhalo$C_{1-6}$alkyl, cyano, aryl or Het.

Embodiments of the invention are compounds of formula (I) or any of the subgroups of compounds of formula (I) wherein $R^4$ and $R^5$ independently from one another are hydrogen, halo, nitro, carboxyl, methyl, ethyl, isopropyl, tert-butyl, methoxy, ethoxy, isopropoxy, tert-butoxy, methylcarbonyl, ethylcarbonyl, isopropylcarbonyl, tert-butyl-carbonyl, methoxycarbonyl, ethoxycarbonyl, isopropoxycarbonyl, tert-butoxycarbonyl, methylthio, ethylthio, isopropylthio, tert-butylthio, trifluoromethyl, or cyano.

Preferred embodiments of the invention are compounds of formula (I) or any of the subgroups of compounds of formula (I) wherein one of $R^4$ and $R^5$ is hydrogen.

Preferred embodiments of the invention are compounds of formula (I) or any of the subgroups of compounds of formula (I) wherein one of $R^4$ and $R^5$ is halo (in particular fluoro), trifluoromethyl or $C_{1-6}$alkyl (in particular methyl). Other preferred embodiments are those wherein one of $R^4$ and $R^5$ is halo (in particular fluoro), trifluoromethyl or methyl, and the other of $R^4$ and $R^5$ is hydrogen.

Preferred embodiments of the invention are compounds of formula (I) or any of the subgroups of compounds of formula (I) wherein one of $R^4$ and $R^5$ is in para position in respect of the W group. Further preferred embodiments are compounds of formula (I) or any of the subgroups of compounds of formula (I) wherein one of $R^4$ and $R^5$ is halo (in particular fluoro), trifluoromethyl or methyl, and is in para position in respect of the W group; the other of $R^4$ and $R^5$ may be as defined above or may be hydrogen.

The compounds of formula (I) consist of three building blocks P1, P2, P3. Building block P1 further contains a P1' tail. The carbonyl group marked with an asterisk in compound (I-c) below may be part of either building block P2 or of building block P3. For reasons of chemistry, building block P2 of the compounds of formula (I) wherein X is C incorporates the carbonyl group attached to the position 1'.

The linking of building blocks P1 with P2, P2 with P3, and P1 with P1' (when $R^1$ is —NH—$SO_2R^7$) involves forming an amide bond. The linking of blocks P1 and P3 involves double bond formation. The linking of building blocks P1, P2 and P3 to prepare compounds (I-i) or (I-j) can be done in any given sequence. One of the steps involves a cyclization whereby the macrocycle is formed.

Represented herebelow are compounds (I-i) which are compounds of formula (I) wherein carbon atoms C7 and C8 are linked by a double bond, and compounds (I-j) which are compounds of formula (I) wherein carbon atoms C7 and C8 are linked by a single bond. The compounds of formula (I-j) can be prepared from the corresponding compounds of formula (I-I) by reducing the double bond in the macrocycle.

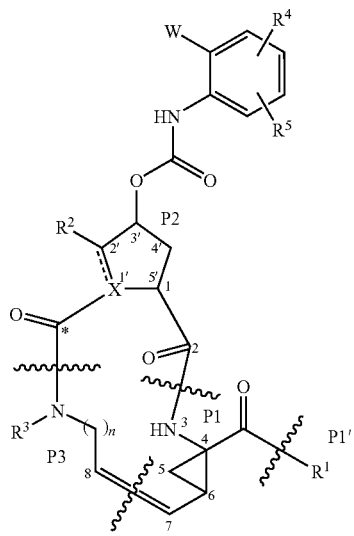

(I-i)

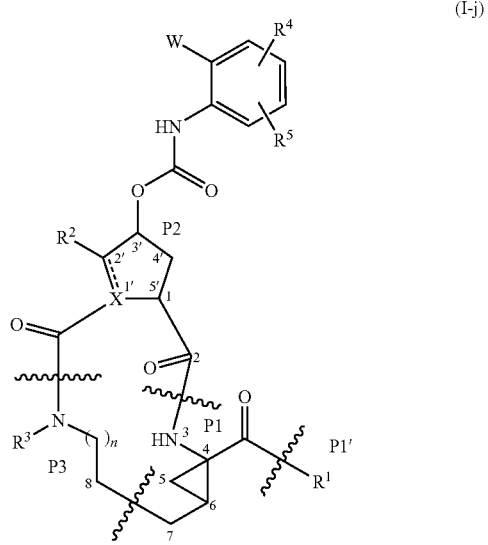

(I-j)

The synthesis procedures described hereinafter are meant to be applicable for as well the racemates, stereochemically pure intermediates or end products, as any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-a) and (I-b).

In the synthesis procedures described hereinafter, $R^8$ represents a radical

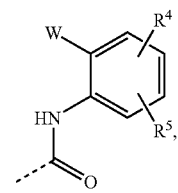

wherein the dotted line represents the bond by which the radical is linked to the remainder of the molecule.

In a preferred embodiment, compounds (I) wherein the bond between $C_7$ and $C_8$ is a double bond, which are compounds of formula (I-i), as defined above, may be prepared as outlined in the following reaction scheme:

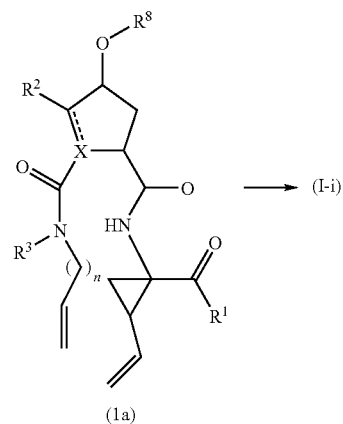

(1a)

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. Benzylidene-bis(tricyclohexylphosphine)dichlororuthenium and (1,3-bis-(2,4,6-trimethylphenyl)-2-imidazolidinylidene)dichloro(phenylmethylene)-(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2,4,6-trimethylphenyl)-2-imidazolidinylidene)dichloro(o-isopropoxyphenylmethylene)ruthenium respectively. Also other catalysts containing other transition metals such as Mo can be used for this reaction.

The metathesis reactions may be conducted in a suitable solvent such as for example ethers, e.g. THF, dioxane; halogenated hydrocarbons, e.g. dichoromethane, $CHCl_3$, 1,2-dichloroethane and the like, hydrocarbons, e.g. toluene. In a preferred embodiment, the metathesis reaction is conducted in toluene. These reactions are conducted at increased temperatures under nitrogen atmosphere.

Compounds of formula (I) wherein the link between C7 and C8 in the macrocycle is a single bond, i.e. compounds of formula (I-j), can be prepared from the compounds of formula (I-i) by a reduction of the $C_7$-$C_8$ double bond in the compounds of formula (I-i). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The $R^1$ group can be connected to the P1 building block at any stage of the synthesis, i.e. before or after the cyclization, or before or after the cyclization and reduction as described herein above. The compounds of formula (I) wherein $R^1$ represents —$NHSO_2R^7$, said compounds being represented by formula (I-k-1), can be prepared by linking the $R^1$ group to P1 by forming an amide bond between both moieties. Similarly, the compounds of formula (I) wherein $R^1$ represents —$OR^6$, i.e. compounds (I-k-2), can be prepared by linking the $R^1$ group to P1 by forming an ester bond. In one embodiment, the —$OR^6$ groups are introduced in the last step of the synthesis of the compounds (I) as outlined in the following reaction schemes wherein G represents a group:

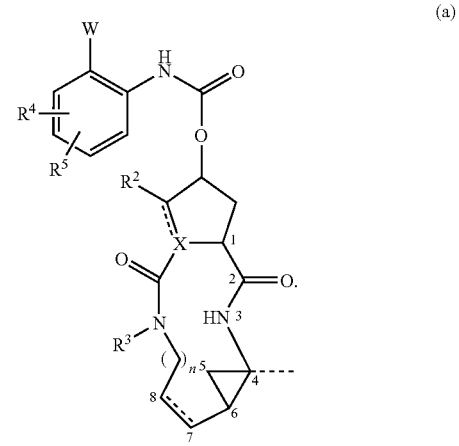

(a)

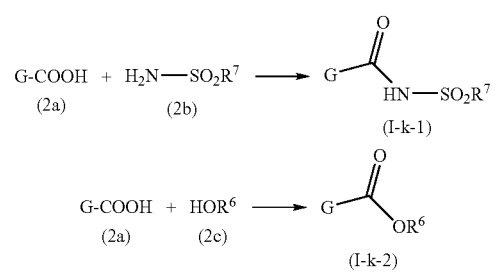

Intermediate (2a) can be coupled with the amine (2b) by an amide forming reaction such as any of the procedures for the formation of an amide bond described hereinafter. In particular, (2a) may be treated with a coupling agent, for example N,N'-carbonyl-diimidazole (CDI), EEDQ, IIDQ, EDCI or benzotriazol-1-yl-oxy-tris-pyrrolidino-phosphonium hexafluorophosphate (commercially available as PyBOP®), in a solvent such as an ether, e.g. THF, or a halogenated hydrocarbon, e.g. dichloromethane, chlorophorm, dichloroethane, and reacted with the desired sulfonamide (2b), preferably after reacting (2a) with the coupling agent. The reactions of (2a) with (2b) preferably are conducted in the presence of a base, for example a trialkylamine such as triethylamine or diisopropylethylamine, or 1,8-diazabicyclo[5.4.0]undec-7-ene (DBU). Intermediate (2a) can also be converted into an activated form, e.g. an activated form of general formula G-CO—Z, wherein Z represents halo, or the rest of an active ester, e.g. Z is an aryloxy group such as phenoxy, p.nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. $C_{1-4}$alkyl, such as methyl, ethyl, propyl, i.propyl, butyl, t.butyl, i.butyl, or benzyl). The activated form G-CO—Z is reacted with the sulfonamide (2b).

The activation of the carboxylic acid in (2a) as described in the above reactions may lead to an internal cyclization reaction to an azalactone intermediate of formula

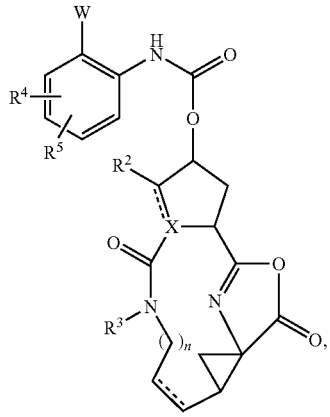

(2a-1)

wherein X, W, R², R³, R⁴ R⁵, n are as specified above and wherein the stereogenic centers may have the stereochemical configuration as specified above, for example as in (I-a) or (I-b). The intermediates (2a-1) can be isolated from the reaction mixture, using conventional methodology, and the isolated intermediate (2a-1) is then reacted with (2b), or the reaction mixture containing (2a-1) can be reacted further with (2b) without isolation of (2a-1). In one embodiment, where the reaction with the coupling agent is conducted in a water-immiscible solvent, the reaction mixture containing (2a-1) may be washed with water or with slightly basic water in order to remove all water-soluble side products. The thus obtained washed solution may then be reacted with (2b) without additional purification steps. The isolation of intermediates (2a-1) on the other hand may provide certain advantages in that the isolated product, after optional further purification, may be reacted with (2b), giving rise to less side products and an easier work-up of the reaction.

Intermediate (2a) can be coupled with the alcohol (2c) by an ester forming reaction. For example, (2a) and (2c) are reacted together with removal of water either physically, e.g. by azeotropical water removal, or chemically by using a dehydrating agent. Intermediate (2a) can also be converted into an activated form G-CO—Z, such as the activated forms mentioned above, and subsequently reacted with the alcohol (2c). The ester forming reactions preferably are conducted in the presence of a base such as an alkali metal carbonate or hydrogen carbonate, e.g. sodium or potassium hydrogen carbonate, or a tertiary amine such as the amines mentioned herein in relation to the amide forming reactions, in particular a trialkylamine, e.g. triethylamine. Solvents that can be used in the ester forming recations comprise ethers such as THF; halogenated hydrocarbons such as dichoromethane, $CH_2Cl_2$; hydrocarbons such as toluene; polar aprotic solvents such as DMF, DMSO, DMA; and the like solvents.

The compounds of formula (I) wherein R³ is hydrogen, said compounds being represented by (I-1), can also be prepared by removal of a protecting group PG, from a corresponding nitrogen-protected intermediate (3a), as in the following reaction scheme. The protecting group PG in particular is any of the nitrogen protecting groups mentioned hereinafter and can be removed using procedures also mentioned hereinafter:

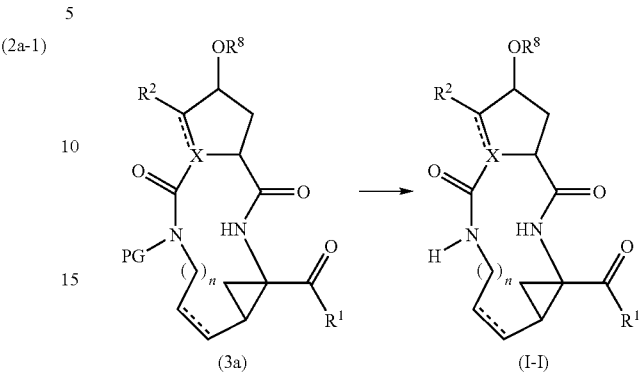

The starting materials (3a) in the above reaction can be prepared following the procedures for the preparation of compounds of formula (I), but using intermediates wherein the group R³ is PG.

The compounds of formula (I) can also be prepared by reacting an intermediate (4a) with an aniline (4b) in the presence of a carbamate forming reagent as outlined in the following reaction scheme wherein the various radicals have the meanings specified above:

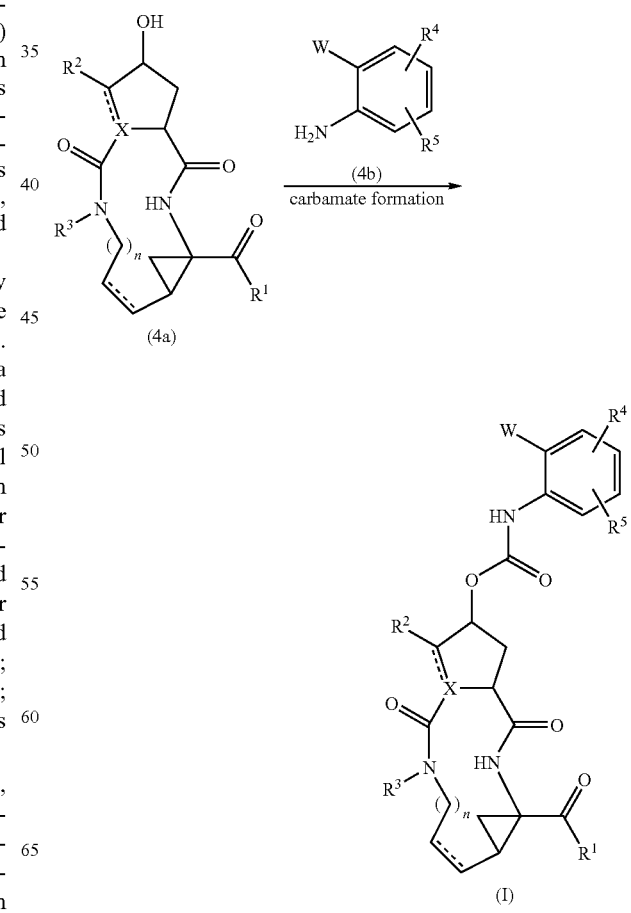

The reaction of intermediates (4a) with the carbamate forming reagent is conducted in the same solvents and bases as those used for the amide bond formation as described hereinafter.

Carbamate forming reactions may be conducted using a variety of methods, in particular by reaction of amines with alkyl chloroformates; by reaction of alcohols with carbamoyl chlorides or isocyanates; via reactions involving metal complexes or acyl transfer agents. See for example, Greene, T. W. and Wuts, P. G. M., "Protective Groups in Organic Synthesis"; 1999; Wiley and Sons, p. 309-348. Carbon monoxide and certain metal catalysts can be used to synthesize carbamates from several starting compounds, including amines. Metals such as palladium, iridium, uranium, and platinum may be used as catalysts. Methods using carbon dioxide for synthesis of carbamates that have been also been reported, can also be used (see for example, Yoshida, Y., et al., *Bull. Chem. Soc. Japan* 1989, 62, 1534; and Aresta, M., et al., *Tetrahedron*, 1991, 47, 9489).

One approach for the preparation of carbamates involves the use of intermediates (4b)

wherein Q is leaving group such as halo, in particular chloro and bromo, or a group used in active esters for amide bond formation, such as those mentioned above, for example phenoxy or substituted phenoxy such as p.chloro and p.nitrophenoxy, trichlorophenoxy, pentachlorophenoxy, N-hydroxysuccinimidyl, and the like. Intermediates (4b) can be derived from alcohols (4a) and phosgene, thus forming a chloroformate, or by transferring the chloro in the latter to intermediates (5a) which are intermediates of formula (5) wherein Q is $Q^1$. In this and the following reaction procedures, $Q^1$ represents any of the active ester moieties such as those mentioned above. Intermediates (4b) are reacted with (4a), obtaining compounds (I).

Intermediates (4b-1), which are intermediates (4b) wherein Q is $Q^1$, can also be prepared by reacting the alcohol (4a) with carbonates $Q^1$-CO-$Q^1$ such as e.g. bisphenol, bis-(substituted phenol) or bis N-hydroxy-succinimidyl carbonates:

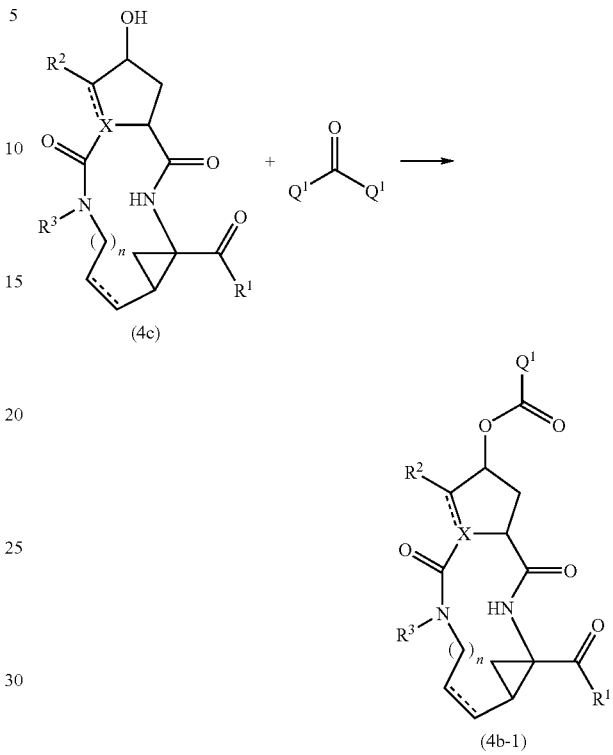

(4c)

(4b-1)

The reagents (5a) may also be prepared from chloroformates Cl—CO-$Q^1$ as follows:

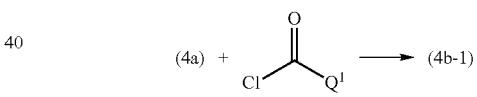

The above reactions to prepare reagents (4b-1) may be conducted in the presence of the bases and solvents mentioned hereinafter for the synthesis of amide bonds, in particular triethylamine and dichloromethane.

Alternatively, in order to prepare the compounds of formula (I), first an amide bond between building blocks P2 and P1 is formed, followed by coupling of the P3 building block to the P1 moiety in P1-P2, and a subsequent carbamate or ester bond formation between P3 and the P2 moiety in P2-P1-P3 with concomitant ring closure.

Yet another alternative synthetic methodology is the formation of an amide bond between building blocks P2 and P3, followed by the coupling of building block P1 to the P3 moiety in P3-P2, and a last amide bond formation between P1 and P2 in P1-P3-P2 with concomitant ring closure.

Building blocks P1 and P3 can be linked to a P1-P3 sequence. If desired, the double bond linking P1 and P3 may be reduced. The thus formed P1-P3 sequence, either reduced or not, can be coupled to building block P2 and the thus forming sequence P1-P3-P2 subsequently cyclized, by forming an amide bond.

Building blocks P1 and P3 in any of the previous approaches can be linked via double bond formation, e.g. by the olefin metathesis reaction described hereinafter, or a Wittig type reaction. If desired, the thus formed double bond can be reduced, similarly as described above for the conversion of (I-i) to (I-j). The double bond can also be reduced at a later stage, i.e. after addition of a third building block, or after formation of the macrocycle. Building blocks P2 and P1 are linked by amide bond formation and P3 and P2 are linked by carbamate or ester formation.

The tail P1' can be bonded to the P1 building block at any stage of the synthesis of the compounds of formula (I), for example before or after coupling the building blocks P2 and P1; before or after coupling the P3 building block to P1; or before or after ring closure.

The individual building blocks can first be prepared and subsequently coupled together or alternatively, precursors of the building blocks can be coupled together and modified at a later stage to the desired molecular composition.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, DBU (1,8-diazabicyclo[5.4.0]undec-7-ene), or 4-DMAP. Further coupling agents are (benzotriazol-1-yloxy)tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyloxy-1,2-dihydroquinoline (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicycle[5.4.0]undec-7-ene (DBU). The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:

1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and
7) thiol containing groups such as phenylthiocarbonyl and dithiasuccinoyl. Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethyl-formamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (1a) wherein X is N, said intermediates being represented by formula (1a-1), may be prepared using an urea forming reaction, starting from intermediates (5a) which are reacted with an alkenamine (5b) in the presence of a carbonyl introducing agent as outlined in the following reaction scheme.

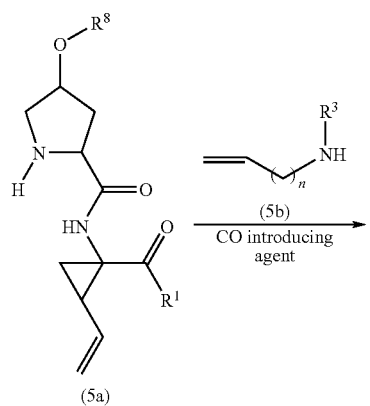

-continued

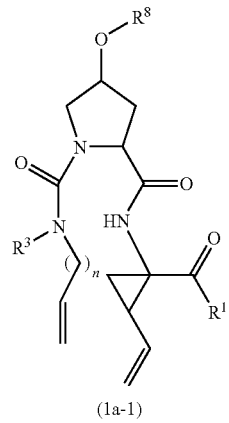

(1a-1)

Carbonyl (CO) introducing agents include phosgene, or phosgene derivatives such as carbonyl diimidazole (CDI), and the like. In one embodiment (5a) is reacted with the CO introducing agent in the presence of a suitable base and a solvent, which can be the bases and solvents used in the amide forming reactions as described above. Thereafter, the amine (5b) is added thereby obtaining intermediates (1a-1) as in the above scheme. In a particular embodiment, the base is a hydrogencarbonate, e.g. $NaHCO_3$, or a tertiary amine such as triethylamine and the like, and the solvent is an ether or halogenated hydrocarbon, e.g. THF, $CH_2Cl_2$, $CHCl_3$, and the like. An alternative route using similar reaction conditions involves first reacting the CO introducing agent with the amine (5b) and then reacting the thus formed intermediate with (5a).

The intermediates (1a-1) can alternatively be prepared as follows:

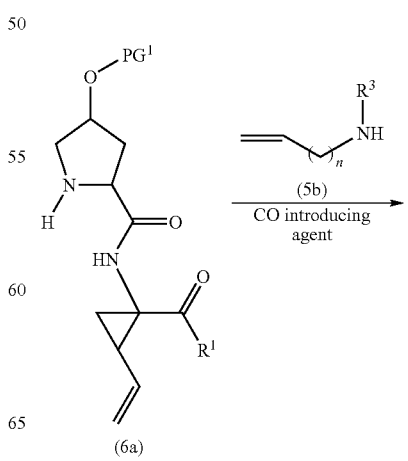

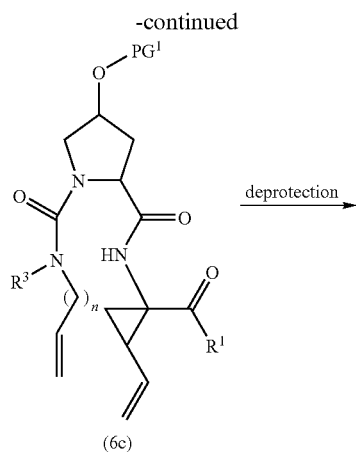

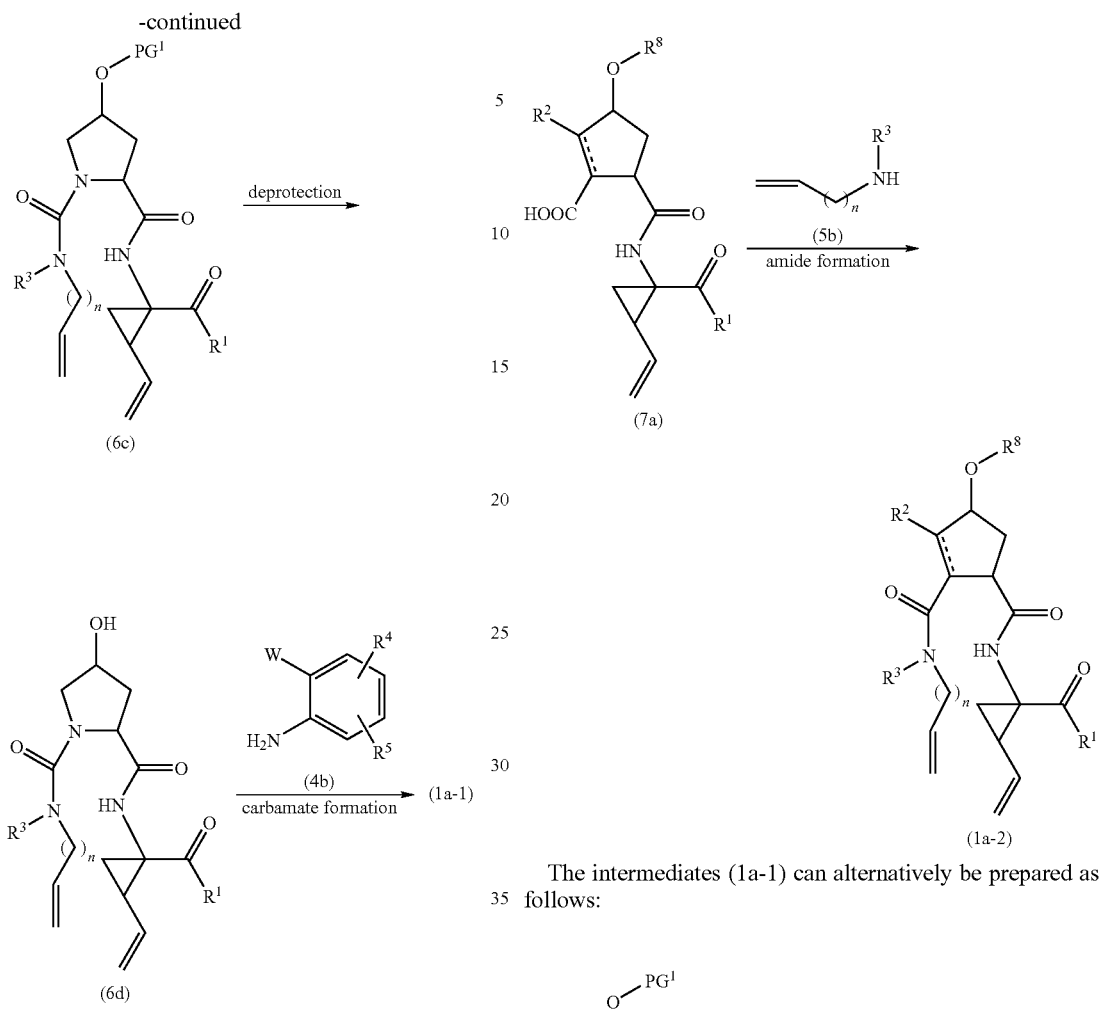

The intermediates (1a-1) can alternatively be prepared as follows:

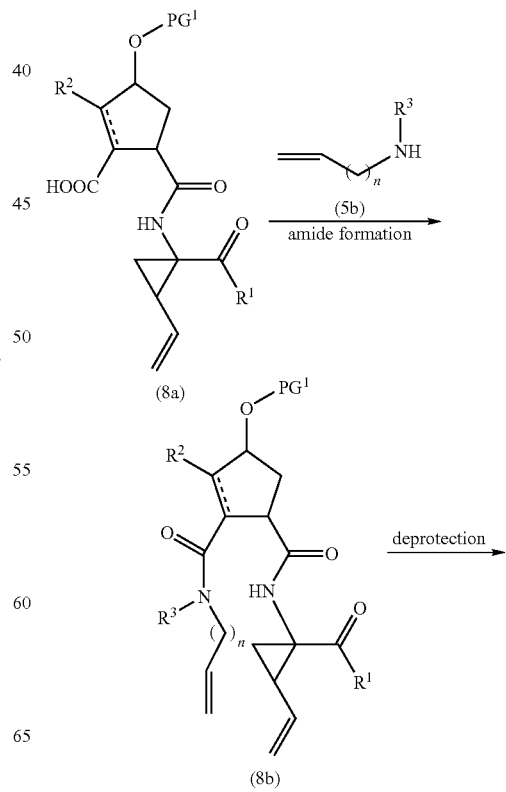

PG$^1$ is an O-protecting group, which can be any of the groups mentioned herein and in particular is a benzoyl or substituted benzoyl group such as 4-nitrobenzoyl. In the latter instance this group can be removed by reaction with a an alkali metal hydroxide (LiOH, NaOH, KOH), in particular where PG$^1$ is 4-nitrobenzoyl, with LiOH, in an aqueous medium comprising water and a water-soluble organic solvent such as an alkanol (methanol, ethanol) and THF.

Intermediates (6a) are reacted with (5b) in the presence of a carbonyl introducing agent, similar as described above, and this reaction yields intermediates (6c). These are deprotected, in particular using the reaction conditions mentioned above. The resulting alcohol (6d) is reacted with intermediates (4b) in a carbamate forming reaction, as described above for the reaction of (4a) with (4b), and this reaction results in intermediates (1a-1).

The intermediates of formula (1a) wherein X is C, said intermediates being represented by formula (1a-2), may be prepared by an amide forming reaction starting from intermediates (7a) which are reacted with an alkenamine (5b) as shown in the following reaction scheme, using reaction conditions for preparing amides such as those described above.

-continued

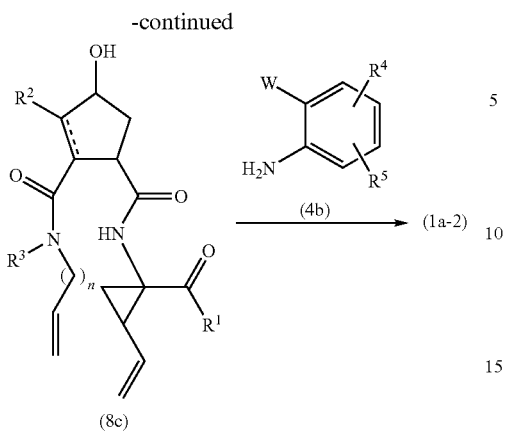

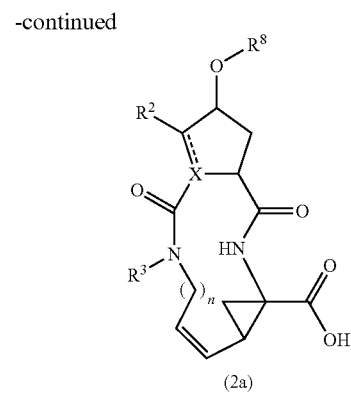

PG$^1$ is an O-protecting group as described above. The same reaction conditions as described above may be used: amide formation as described above, removal of PG$^1$ as in the description of the protecting groups and introduction of R$^8$ as in the reactions of (4a) with the anilines (4b).

The intermediates of formula (2a) may be prepared by first cyclizing an open amide (9a) to a macrocyclic ester (9b), which in turn is converted to an intermediate (2a) as follows:

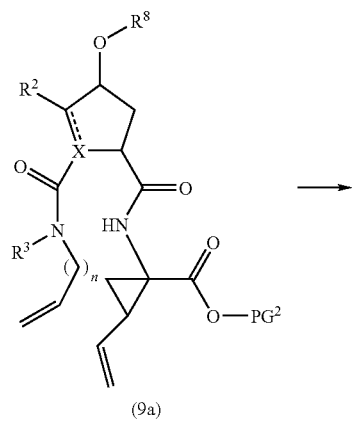

PG$^2$ is a carboxyl protecting group, e.g. one of the carboxyl protecting groups mentioned above, in particular a C$_{1-4}$alkyl or benzyl ester, e.g. a methyl, ethyl or t.butyl ester. The reaction of (9a) to (9b) is a metathesis reaction and is conducted as described above. Removal of PG$^2$ as described above, yields intermediates (2a). Where PG$^1$ is a C$_{1-4}$alkyl ester, it is removed by alkaline hydrolysis, e.g. with NaOH or preferably LiOH, in an aqueous solvent, e.g. a C$_{1-4}$alkanol/water mixture, such as methanol/water or ethanol/water. A benzyl group can be removed by catalytic hydrogenation.

In an alternative synthesis, intermediates (2a) can be prepared as follows:

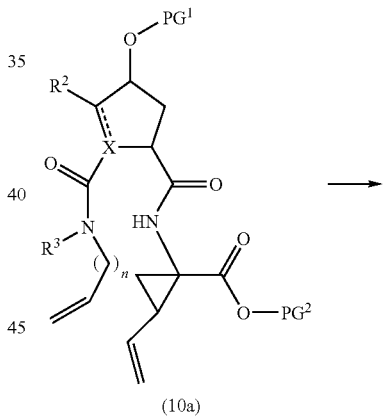

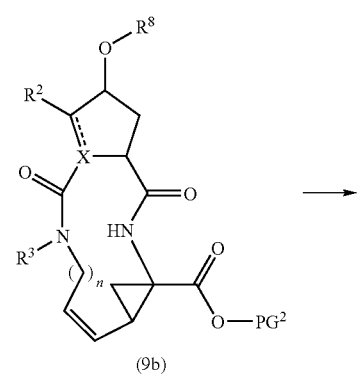

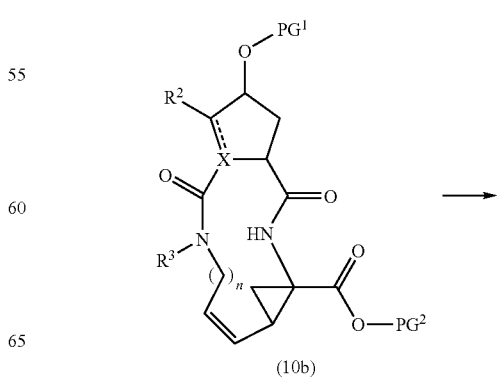

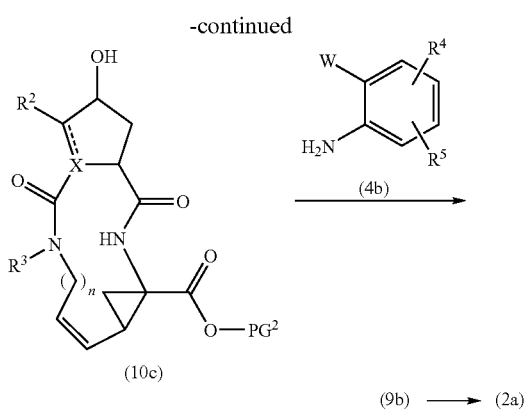

The PG¹ group is selected such that it is selectively cleavable towards PG². PG² may be e.g. methyl or ethyl esters, which can be removed by treatment with an alkali metal hydroxide in an aqueous medium, in which case PG¹ e.g. is t.butyl or benzyl. Or alternatively, PG² may be t.butyl esters removable under weakly acidic conditions or PG¹ may be benzyl esters removable with strong acid or by catalytic hydrogenation, in the latter two cases PG¹ e.g. is a benzoic ester such as a 4-nitrobenzoic ester.

First, intermediates (10a) are cyclized to the macrocyclic esters (10b), the latter are deprotected by removal of the PG¹ group to intermediates (10c), which are reacted with anilines (4b), followed by removal of the carboxyl protecting group PG². The cyclization, deprotection of PG¹ and PG², and the coupling with (4b) are as described above.

The R¹ groups can be introduced at any stage of the synthesis, either as the last step as described above, or earlier, before the macrocycle formation, as illustrated in the following scheme:

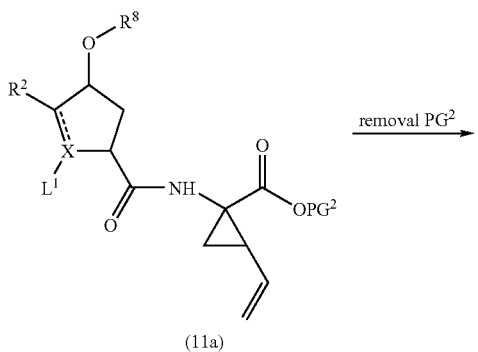

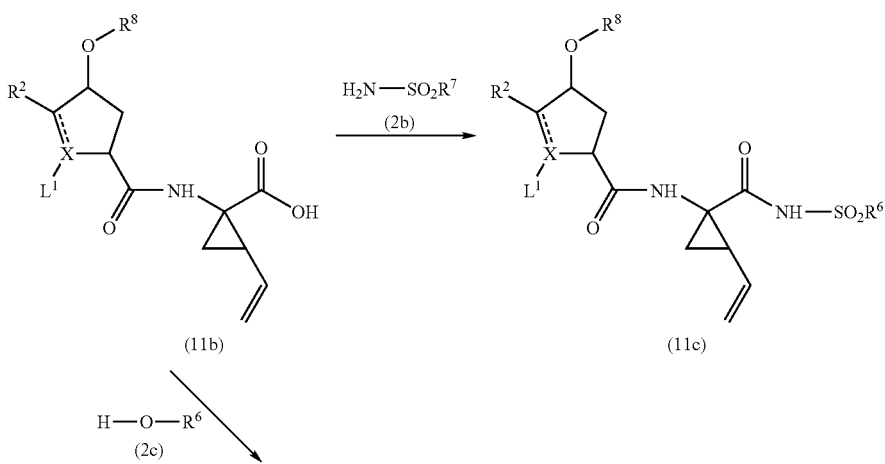

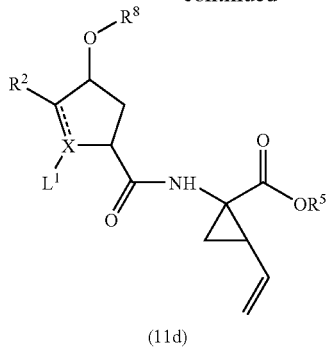

(11d)

In the above scheme, $R^2$, $R^6$, $R^7$, $R^8$, X and $PG^2$ are as defined above and $L^1$ is a P3 group

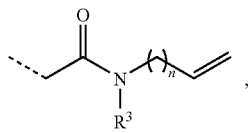

(b)

wherein n and $R^3$ are as defined above and where X is N, $L^1$ may also be a nitrogen-protecting group (PG, as defined above) and where X is C, $L^1$ may also be a group —COOPG$^{2a}$, wherein the group PG$^{2a}$ is a carboxyl protecting group similar as $PG^2$, but wherein PG$^{2a}$ is selectively cleavable towards $PG^2$. In one embodiment PG$^{2a}$ is t.butyl and $PG^2$ is methyl or ethyl.

The intermediates (11c) and (11d) wherein $L^1$ represents a group (b) correspond to the intermediates (1a) and may be processed further as specified above.

Coupling of P1 and P2 Building Blocks

The P1 and P2 building blocks are linked using an amide forming reaction following the procedures described above. The P1 building block may have a carboxyl protecting group $PG^2$ (as in (12b)) or may already be linked to P1' group (as in (12c)). $L^3$ is a N-protecting group (PG), or a group (b), as specified above. $L^3$ is hydroxy, —OPG$^1$ or a group —O—$R^8$ as specified above. Where in any of the following reaction schemes $L^3$ is hydroxy, prior to each reaction step, it may be protected as a group —OPG$^1$ and, if desired, subsequently deprotected back to a free hydroxy function. Similarly as described above, the hydroxy function may be converted to a group —O—$R^8$

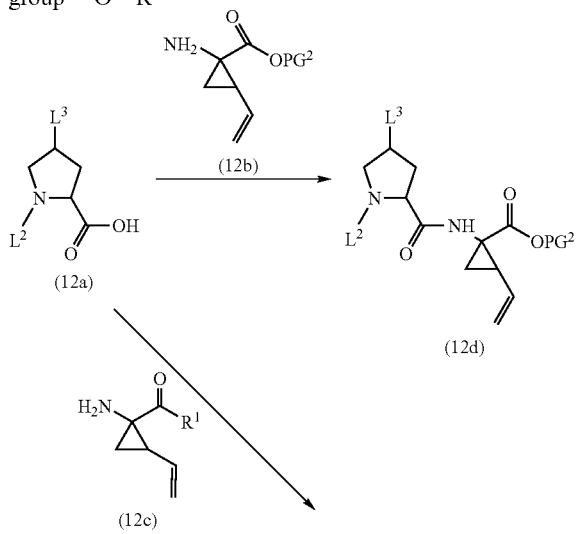

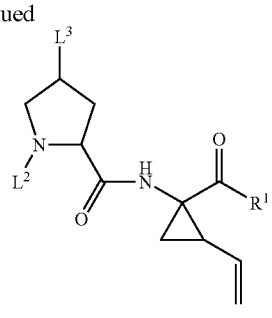

(12e)

In the procedure of the above scheme, a cyclopropyl amino acid (12b) or (12c) is coupled to the acid function of the P2 building block (12a) with the formation of an amide linkage, following the procedures described above. Intermediates (12d) or (12e) are obtained. Where in the latter $L^2$ is a group (b), the resulting products are P3-P2-P1 sequences encompassing some of the intermediates (11c) or (11d) in the previous reaction scheme. Removal of the acid protecting group in (12d), using the appropriate conditions for the protecting group used, followed by coupling with an amine $H_2N$—$SO_2R^7$ (2b) or with HOR$^6$ (2c) as described above, again yields the intermediates (12e), wherein —COR$^1$ are amide or ester groups. Where $L^2$ is a N-protecting group, it can be removed yielding intermediates (5a) or (6a). In one embodiment, PG in this reaction is a BOC group and PG is methyl or ethyl. Where additionally $L^3$ is hydroxy, the starting material (12a) is Boc-L-hydroxyproline. In a particular embodiment, PG is BOC, $PG^2$ is methyl or ethyl and $L^3$ is —O—$R^8$.

In one embodiment, $L^2$ is a group (b) and these reactions involve coupling P1 to P2-P3, which results in the intermediates (1a-1) or (1a) mentioned above. In another embodiment, $L^2$ is a N-protecting group PG, which is as specified above, and the coupling reaction results in intermediates (12d-1) or (12e-1), from which the group PG can be removed, using reaction conditions mentioned above, obtaining intermediates (12-f) or respectively (12g), which encompass intermediates (5a) and (6a) as specified above:

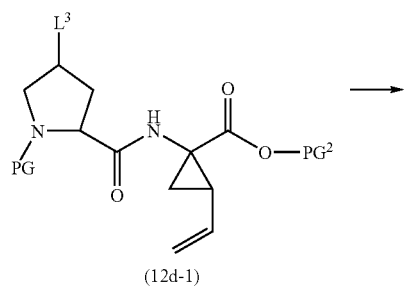

(12d-1)

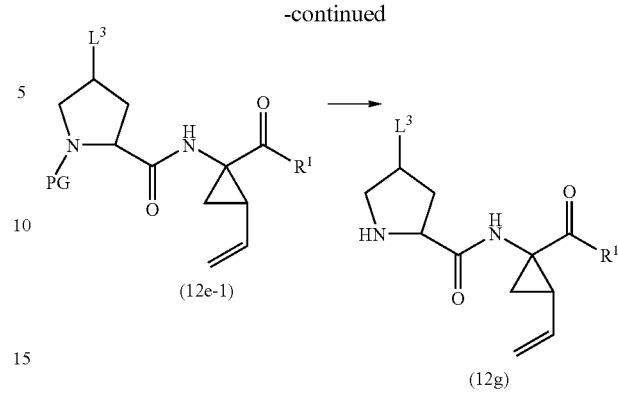

(12e-1)

(12g)

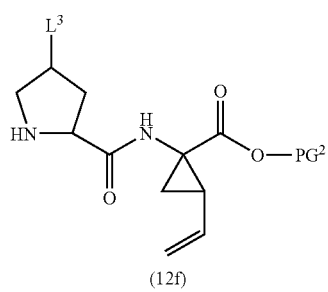

(12f)

In one embodiment, the group $L^3$ in the above schemes represents a group —O-$PG^1$ which can be introduced on a starting material (12a) wherein $L^3$ is hydroxy. In this instance $PG^1$ is chosen such that it is selectively cleavable towards group $L^2$ being PG.

In a similar way, P2 building blocks wherein X is C, which are cyclopentane or cyclopentene derivatives, can be linked to P1 building blocks as outlined in the following scheme wherein $R^1$, $R^2$, $L^3$, $PG^2$ and $PG^{2a}$ are carboxyl protecting groups. $PG^{2a}$ typically is chosen such that it is selectively cleavable towards group $PG^2$. Removal of the $PG^{2a}$ group in (13c) yields intermediates (7a) or (8a), which can be reacted with (5b) as described above.

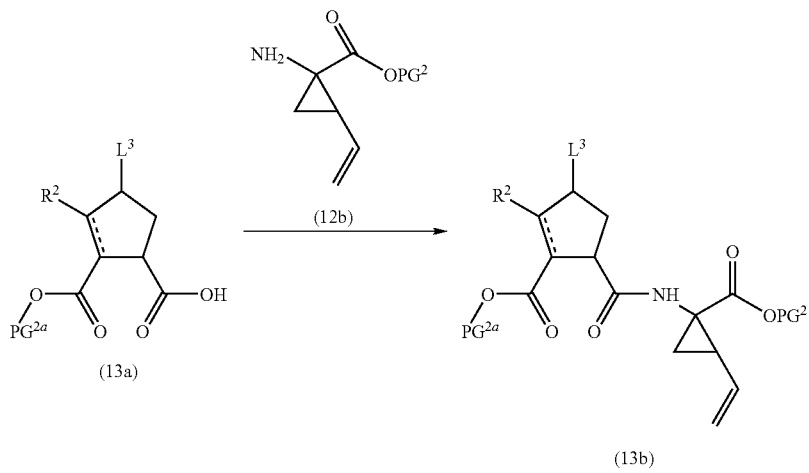

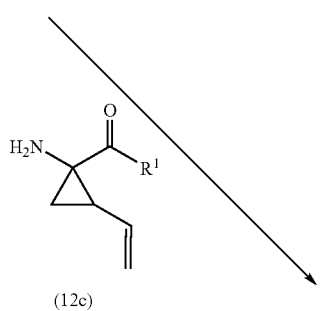

(12c)

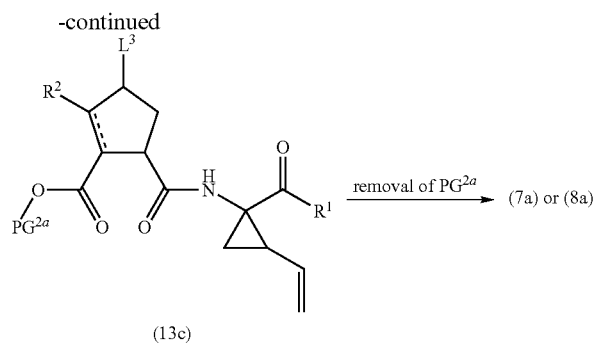

(13c)

In one particular embodiment, where X is C, $R^2$ is H, and where X and the carbon bearing $R^2$ are linked by a single bond (P2 being a cyclopentane moiety), $PG^{2a}$ and $L^3$ taken together form a bond and the P2 building block is represented by formula:

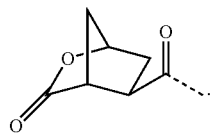

(c)

Bicyclic acid (14a) is reacted with (12b) or (12c) similar as described above to (14b) and (14c) respectively, wherein the lactone is opened to give intermediates (14c) and (14e). The lactone can be opened using ester hydrolysis procedures, for example using the reaction conditions described above for the alkaline removal of a $PG^1$ group in (9b), in particular using basic conditions such as an alkali metal hydroxide, e.g. NaOH, KOH, in particular LiOH.

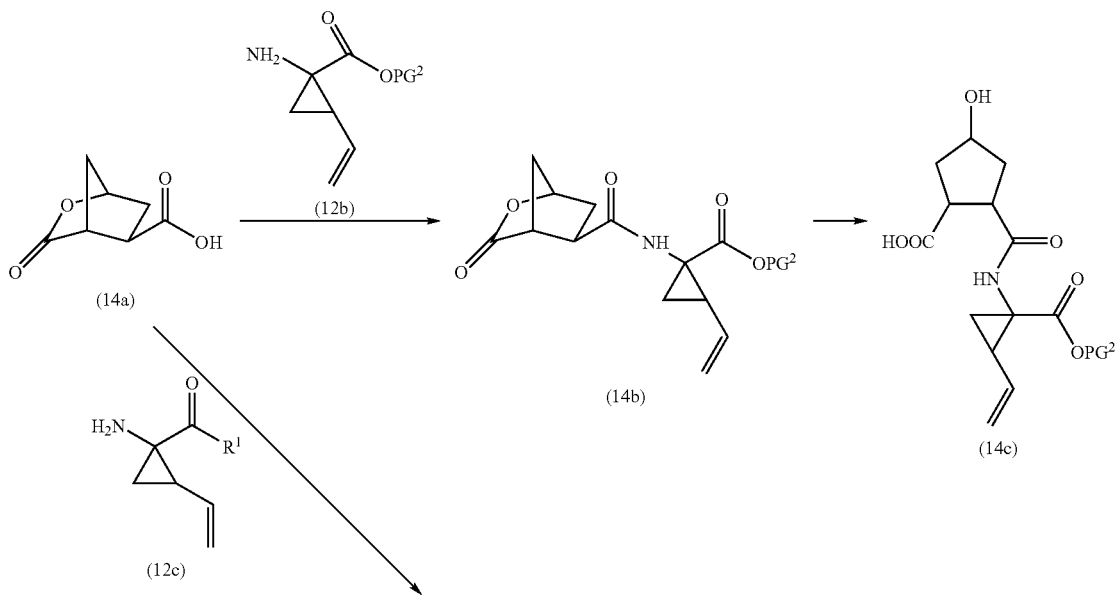

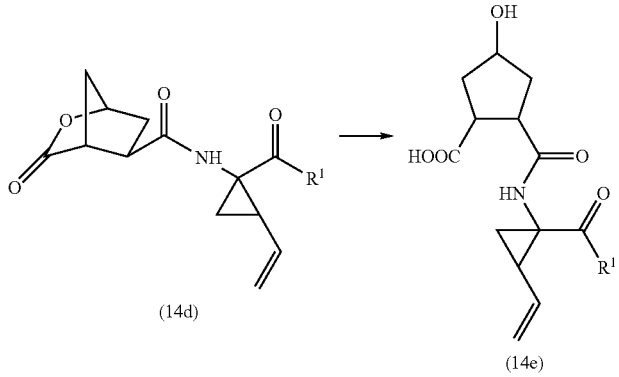

Intermediates (14c) and (14e) can be processed further as described hereinafter.

Coupling of P3 and P2 Building Blocks

For P2 building blocks that have a pyrrolidine moiety, the P3 and P2 or P3 and P2-P1 building blocks are linked using an urea forming reaction following the procedures described above for the coupling of (5a) with (5b). A general procedure for coupling P2 blocks having a pyrrolidine moiety is represented in the following reaction scheme wherein $L^3$ is as specified above and $L^4$ is a group —O—$PG^2$, a group

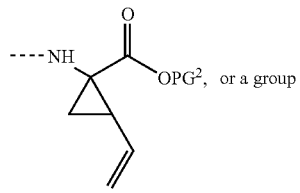

(d)

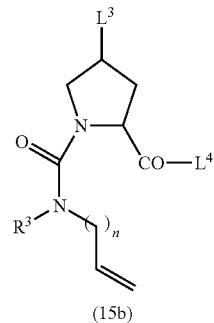

(15b)

In one embodiment $L^4$ in (15a) is a group —$OPG^2$, the $PG^2$ group may be removed and the resulting acid coupled with cyclopropyl amino acids (12a) or (12b), yielding intermediates (12d) or (12e) wherein $L^2$ is a radical (d) or (e).

A general procedure for coupling P3 blocks with a P2 block or a with a P2-P1 block wherein the P2 is a cyclopentane or cyclopentene is shown in the following scheme. $L^3$ and $L^4$ are as specified above.

(e)

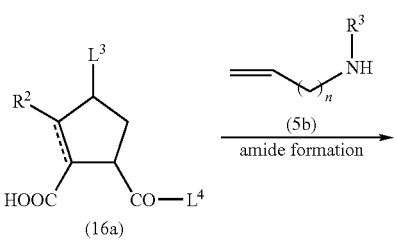

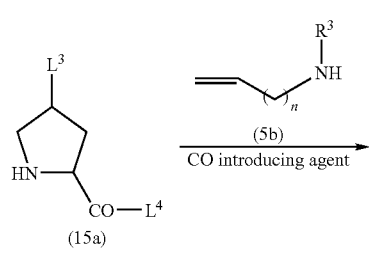

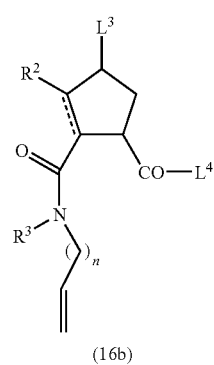

In a particular embodiment $L^3$ and $L^4$ taken together may form a lactone bridge as in (14a), and the coupling of a P3 block with a P2 block is as follows:

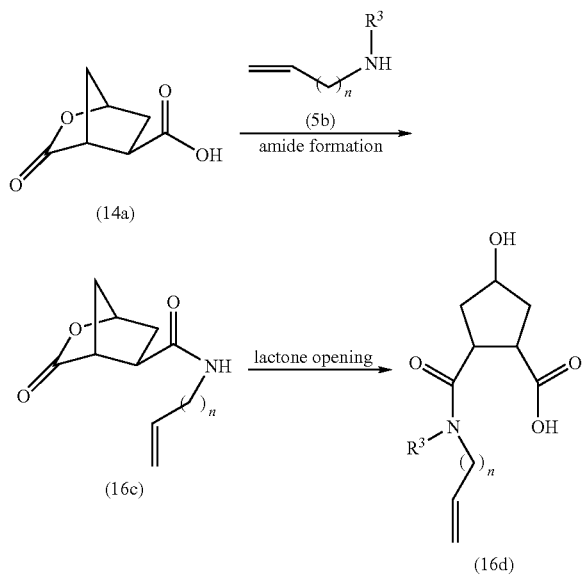

Bicyclic lactone (14a) is reacted with (5b) in an amide forming reaction to amide (16c) in which the lactone bridge is opened to (16d). The reaction conditions for the amide forming and lactone opening reactions are as described above or hereinafter. Intermediate (16d) in turn can be coupled to a P1 group as described above.

The reactions in the above two schemes are conducted using the same procedures as described above for the reactions of (5a), (7a) or (8a) with (5b) and in particular the above reactions wherein $L^4$ is a group (d) or (e) correspond to the reactions of (5a), (7a) or (8a) with (5b), as described above.

The building blocks P1, P1', P2 and P3 used in the preparation of the compounds of formula (I) can be prepared starting from art-known intermediates. A number of such syntheses are described hereafter in more detail.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

Synthesis of P2 Building Blocks

The P2 building blocks contain either a pyrrolidine, a cyclopentane, or a cyclopentene moiety substituted with a group —O—$R^8$.

P2 building blocks containing a pyrrolidine moiety can be derived from commercially available hydroxy proline.

The preparation of P2 building blocks that contain a cylopentane ring may be performed as shown in the scheme below.

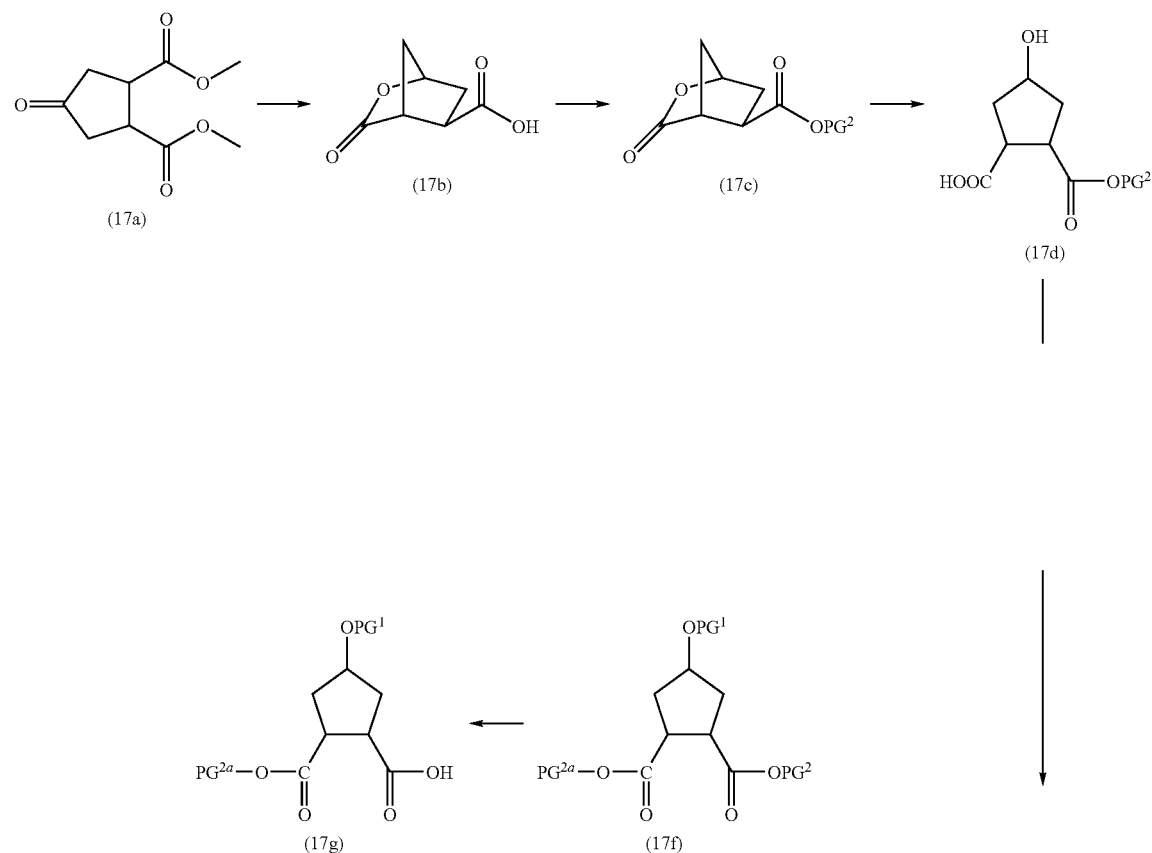

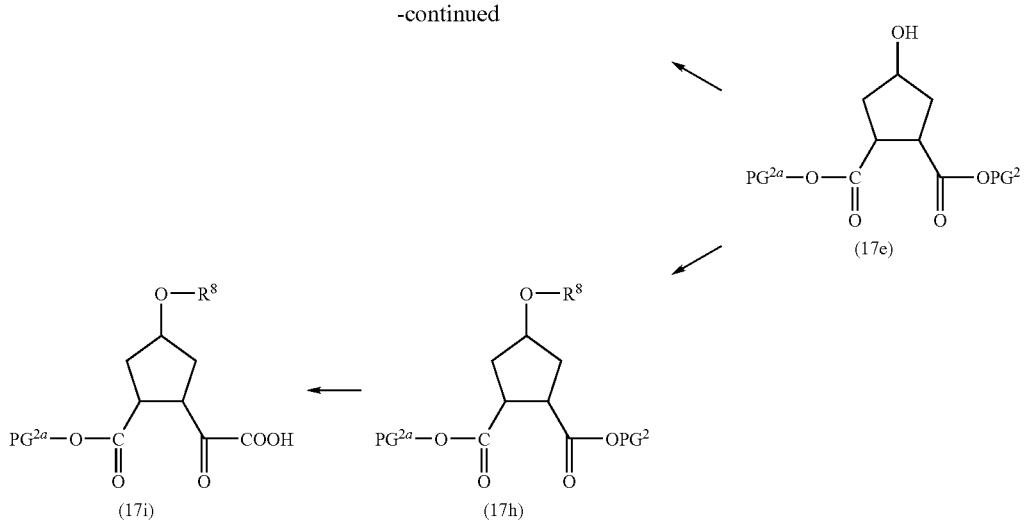

The bicyclic acid (17b) can be prepared, for example, from 3,4-bis(methoxycarbonyl)-cyclopentanone (17a), as described by Rosenquist et al. in Acta Chem. Scand. 46 (1992) 1127-1129. A first step in this procedure involves the reduction of the keto group with a reducing agent like sodium borohydride in a solvent such as methanol, followed by hydrolysis of the esters and finally ring closure to the bicyclic lactone (17b) using lactone forming procedures, in particular by using acetic anhydride in the presence of a weak base such as pyridine. The carboxylic acid functionality in (17b) can then be protected by introducing an appropriate carboxyl protecting group, such as a group $PG^2$, which is as specified above, thus providing bicyclic ester (17c). The group $PG^2$ in particular is acid-labile such as a t.butyl group and is introduced e.g. by treatment with isobutene in the presence of a Lewis acid or with di-tert-butyl dicarbonate in the presence of a base such as a tertiary amine like dimethylamino-pyridine or triethylamine in a solvent like dichloromethane. Lactone opening of (17c) using reaction conditions described above, in particular with lithium hydroxide, yields the acid (17d), which can be used further in coupling reactions with P1 building blocks. The free acid in (17d) may also be protected, preferably with an acid protecting group $PG^{2a}$ that is selectively cleavable towards $PG^2$, and the hydroxy function may be converted to a group —$OPG^1$ or to a group —O—$R^8$. The products obtained upon removal of the group $PG^2$ are intermediates (17g) and (17i) which correspond to intermediates (13a) or (16a) specified above.

Intermediates with specific stereochemistry may be prepared by resolving the intermediates in the above reaction sequence. For example, (17b) may be resolved following art-known procedures, e.g. by salt form action with an optically active base or by chiral chromatography, and the resulting stereoisomers may be processed further as described above. The OH and COOH groups in (17d) are in cis position. Trans analogs can be prepared by inverting the stereochemistry at the carbon bearing the OH function by using specific reagents in the reactions introducing $OPG^1$ or O—$R^8$ that invert the stereochemistry, such as, e.g. by applying a Mitsunobu reaction.

In one embodiment, the intermediates (17d) are coupled to P1 blocks (12b) or (12c), which coupling reactions correspond to the coupling of (13a) or (16a) with the same P1 blocks, using the same conditions. Subsequent introduction of a —O—$R^8$-substituent as described above followed by removal of the acid protection group $PG^2$ yields intermediates (8a-1), which are a subclass of the intermediates (7a), or part of the intermediates (16a). The reaction products of the $PG^2$ removal can be further coupled to a P3 building block. In one embodiment $PG^2$ in (17d) is t.butyl which can be removed under acidic conditions, e.g. with trifluoroacetic acid.

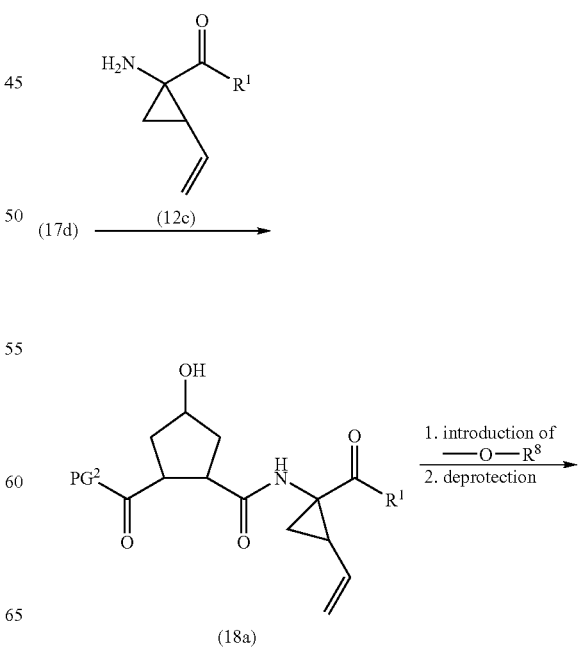

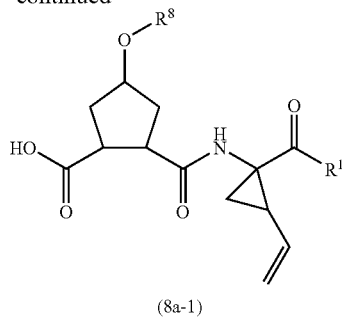

(8a-1)

An unsaturated P2 building block, i.e. a cyclopentene ring, may be prepared as illustrated in the scheme below.

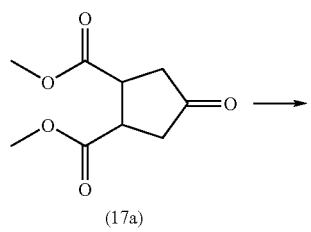

(17a)

A bromination-elimination reaction of 3,4-bis(methoxy-carbonyl)cyclopentanone (17a) as described by Dolby et al. in J. Org. Chem. 36 (1971) 1277-1285 followed by reduction of the keto functionality with a reducing agent like sodium borohydride provides the cyclopentenol (19a). Selective ester hydrolysis using for example lithium hydroxide in a solvent like a mixture of dioxane and water, provides the hydroxy substituted monoester cyclopentenol (19b).

An unsaturated P2 building block wherein $R^2$ can also be other than hydrogen, may be prepared as shown in the scheme below.

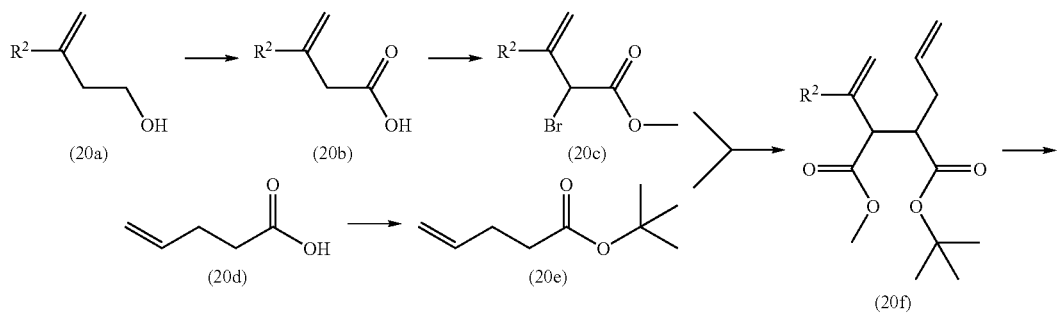

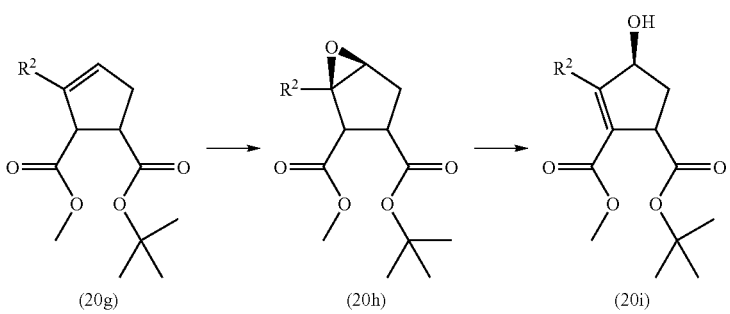

Oxidation of commercially available 3-methyl-3-buten-1-ol (20a), in particular by an oxidizing agent like pyridinium chlorochromate, yields (20b), which is converted to the corresponding methyl ester, e.g. by treatment with acetyl chloride in methanol, followed by a bromination reaction with bromine yielding the α-bromo ester (20c). The latter can then be condensed with the alkenyl ester (20e), obtained from (20d) by an ester forming reaction. The ester in (20e) preferably is a t.butyl ester which can be prepared from the corresponding commercially available acid (20d), e.g. by treatment with di-tert-butyl dicarbonate in the presence of a base like dimethylaminopyridine. Intermediate (20e) is treated with a base such as lithium diisopropyl amide in a solvent like tetrahydrofuran, and reacted with (20c) to give the alkenyl diester (20f). Cyclisation of (20f) by an olefin metathesis reaction, performed as described above, provides cyclopentene derivative (20g). Stereoselective epoxidation of (20g) can be carried out using the Jacobsen asymmetric epoxidation method to obtain epoxide (20h). Finally, an epoxide opening reaction under basic conditions, e.g. by addition of a base, in particular DBN (1,5-diazabicyclo-[4.3.0]non-5-ene), yields the alcohol (20i). Optionally, the double bond in intermediate (20i) can be reduced, for example by catalytic hydrogenation using a catalyst like palladium on carbon, yielding the corresponding cyclopentane compound. The t.butyl ester may be removed to the corresponding acid, which subsequently is coupled to a P1 building block.

The —O—$R^8$ group can be introduced on the pyrrolidine, cyclopentane or cyclopentene rings at any convenient stage of the synthesis of the compounds according to the present invention. One approach is to first introduce the —O—$R^8$ group to the said rings and subsequently add the other desired building blocks, i.e. P1 (optionally with the P1' tail) and P3, followed by the macrocycle formation. Another approach is to couple the building blocks P2, bearing no —O—$R^8$ substituent, with each P1 and P3, and to add the —O—$R^8$ group either before or after the macrocycle formation. In the latter procedure, the P2 moieties have a hydroxy group, which may be protected by a hydroxy protecting group $PG^1$.

$R^8$ groups can be introduced on building blocks P2 by reacting hydroxy substituted intermediates (21a) or (21b) with intermediates (4b) similar as described above for the synthesis of (I) starting from (4a). These reactions are represented in the schemes below, wherein $L^2$ is as specified above and $L^5$ and $L^{5a}$ independently from one another, represent hydroxy, a carboxyl protecting group —$OPG^2$ or —$OPG^{2a}$, or $L^5$ may also represent a P1 group such as a group (d) or (e) as specified above, or $L^{5a}$ may also represent a P3 group such as a group (b) as specified above The groups $PG^2$ and $PG^{2a}$ are as specified above. Where the groups $L^5$ and $L^{5a}$ are $PG^2$ or $PG^{2a}$, they are chosen such that each group is selectively cleavable towards the other. For example, one of $L^5$ and $L^{5a}$ may be a methyl or ethyl group and the other a benzyl or t.butyl group.

In one embodiment in (21a), $L^2$ is PG and $L^5$ is —$OPG^2$, or in (21d), $L^{5a}$ is —$OPG^2$ and $L^5$ is —$OPG^2$ and the $PG^2$ groups are removed as described above.

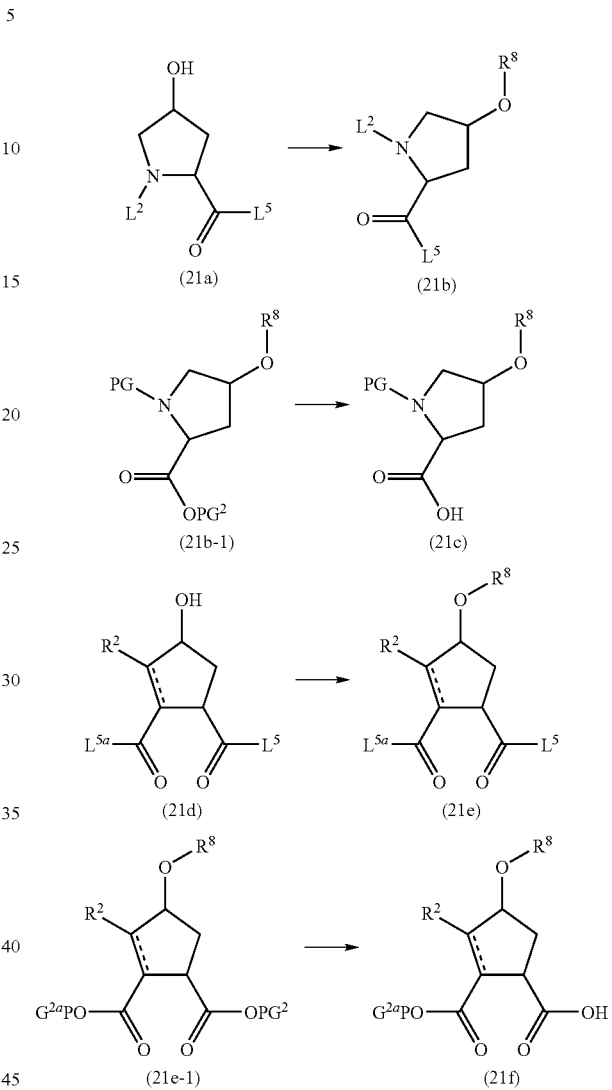

In another embodiment the group $L^2$ is BOC, $L^5$ is hydroxy and the starting material (21a) is commercially available BOC-hydroxyproline, or any other stereoisomeric form thereof, e.g. BOC-L-hydroxyproline, in particular the trans isomer of the latter. Where $L^5$ in (21b) is a carboxyl-protecting group, it may be removed following procedures described above to (21c). In still another embodiment PG in (21b-1) is Boc and $PG^2$ is a lower alkyl ester, in particular a methyl or ethyl ester. Hydrolysis of the latter ester to the acid can be done by standard procedures, e.g. acid hydrolysis with hydrochloric acid in methanol or with an alkali metal hydroxide such as NaOH, in particular with LiOH. In another embodiment, hydroxy substituted cyclopentane or cyclopentene analogs (21d) are converted to (21e), which, where $L^5$ and $L^{5a}$ are —$OPG^2$ or —$OPG^{2a}$, may be converted to the corresponding acids (21f) by removal of the group $PG^2$. Removal of $PG^{2a}$ in (21e-1) leads to similar intermediates.

Intermediates (4b), which are aniline derivatives, can be prepared using art-known procedures.

The anilines described herein, either as such or incorporated onto the pyrrolidine, cyclopentane or cyclopentene moieties in the group —OR$^8$ in the compounds of formula (I) or in any of the intermediates mentioned herein, can be further functionalized. Halo groups can be substituted by $C_{1-6}$alkoxy or heteroaryl groups. A preferred halo for these reactions is fluoro. Usually this type of aromatic substition reaction is conducted in the presence of a base, e.g. an alkali metal alkyl or alkoxide (e.g. butyl lithium, sodium methoxide or ethoxide) or, in a reaction inert solvent, such as dipolar aprotic solvents (DMA, DMF, DMSO, HMPT and the like), halogenated hydrocarbons (dichloro-methane, chlorophorm, dichloroethane) or ethers (THF, dioxan), and in some cases alcohols such as methanol and ethanol. Nitro groups can be reduced to amino groups using standard procedures. Heterocyclyl substituted anilines can also be prepared by building up the heterocycle, for example from anilines or the precursor nitro analogs that are further substituted with an amide or thioamide group. The latter can be converted to a thiazole moiety by condensation with α-bromoketones.

Synthesis of P1 Building Blocks

The cyclopropane amino acid used in the preparation of the P1 fragment is commercially available or can be prepared using art-known procedures.

In particular the amino-vinyl-cyclopropyl ethyl ester (12b) may be obtained according to the procedure described in WO 00/09543 or as illustrated in the following scheme, wherein PG$^2$ is a carboxyl protecting group as specified above:

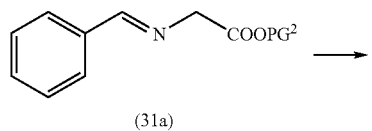

(31a)

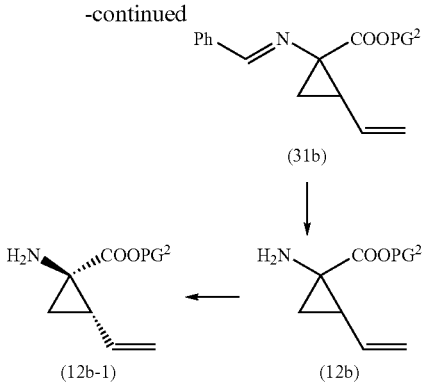

Treatment of commercially available or easily obtainable imine (31a) with 1,4-dihalo-butene in presence of a base produces (31b), which after hydrolysis yields cyclopropyl amino acid (12b), having the allyl substituent syn to the carboxyl group. Resolution of the enantiomeric mixture (12b) results in (12b-1). The resolution is performed using art-known procedures such as enzymatic separation; crystallization with a chiral acid; or chemical derivatization; or by chiral column chromatography. Intermediates (12b) or (12b-1) may be coupled to the appropriate P2 derivatives as described above.

P1 building blocks for the preparation of compounds according to general formula (I) wherein R$^1$ is —OR$^6$ or —NH—SO$_2$R$^7$ can be prepared by reacting amino acids (32a) with the appropriate alcohol or amine respectively under standard conditions for ester or amide formation. Cyclopropyl amino acids (32a) are prepared by introducing a N-protecting group PG, and removal of PG$^2$ and the amino acids (32a) are converted to the amides (12c-1) or esters (12c-2), which are subgroups of the intermediates (12c), as outlined in the following reaction scheme, wherein PG is as specified above.

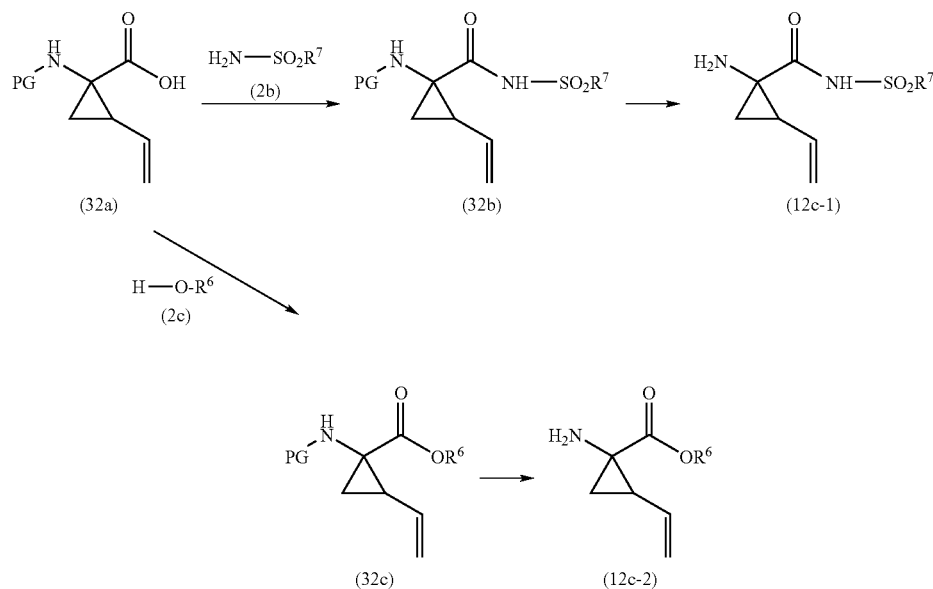

The reaction of (32a) with amine (2b) is an amide forming procedure. The similar reaction with (2c) is an ester forming reaction. Both can be performed following the procedures described above. This reaction yields intermediates (32b) or (32c) from which the amino protecting group is removed by standard methods such as those described above. This in turn results in the desired intermediate (12c-1). Starting materials (32a) may be prepared from the above mentioned intermediates (12b) by first introducing a N-protecting group PG and subsequent removal of the group $PG^2$.

In one embodiment the reaction of (32a) with (2b) is done by treatment of the amino acid with a coupling agent, for example N,N'-carbonyl-diimidazole (CDI) or the like, in a solvent like THF followed by reaction with (2b) in the presence of a base such as 1,8-diazabicyclo[5.4.0]undec-7-ene (DBU). Alternatively the amino acid can be treated with (2b) in the presence of a base like diisopropylethylamine followed by treatment with a coupling agent such as benzotriazole-1-yl-oxy-tris-pyrrolidino-phosphonium hexafluorophosphate (commercially available as PyBOP®) to effect the introduction of the sulfonamide group.

Intermediates (12c-1) or (12c-2) in turn may be coupled to the appropriate proline, cyclopentane or cyclopentene derivatives as described above.

Synthesis of the P3 Building Blocks

The P3 building blocks are available commercially or can be prepared according to methodologies known to the skilled in the art. One of these methodologies is shown in the scheme below and uses monoacylated amines, such as trifluoroacetamide or a Boc-protected amine.

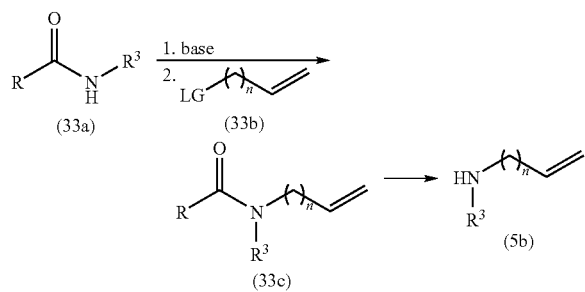

In the above scheme, R together with the CO group forms a N-protecting group, in particular R is t-butoxy, trifluoromethyl; $R^3$ and n are as defined above and LG is a leaving group, in particular halogen, e.g. chloro or bromo.

The monoacylated amines (33a) are treated with a strong base such as sodium hydride and are subsequently reacted with a reagent LG-$C_{5-8}$alkenyl (33b), in particular halo$C_{5-8}$alkenyl, to form the corresponding protected amines (33c). Deprotection of (33c) affords (5b), which are building blocks P3. Deprotection will depend on the functional group R, thus if R is t-butoxy, deprotection of the corresponding Boc-protected amine can be accomplished with an acidic treatment, e.g. trifluoroacetic acid. Alternatively, when R is for instance trifluoromethyl, removal of the R group is accomplished with a base, e.g. sodium hydroxide.

The following scheme illustrates yet another method for preparing a P3 building block, namely a Gabriel synthesis of primary $C_{5-8}$alkenylamines, which can be carried out by the treatment of a phthalimide (34a) with a base, such as NaOH or KOH, and with (33b), which is as specified above, followed by hydrolysis of the intermediate N-alkenyl imide to generate a primary $C_{5-8}$alkenylamine (5b-1).

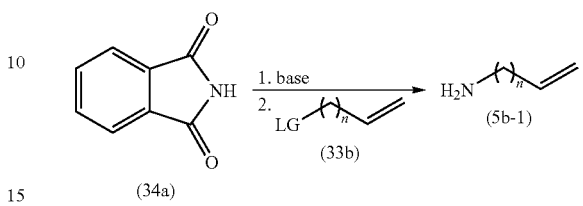

In the above scheme, n is as defined above.

Compounds of formula (I) may be converted into each other following art-known functional group transformation reactions. For example, amino groups may be N-alkylated, nitro groups reduced to amino groups, a halo atom may be exchanged for another halo.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis. A number of the compounds of this invention moreover are active against mutated strains of HCV. Additionally, many of the compounds of this invention show a favorable pharmacokinetic profile and have attractive properties in terms of bioavailabilty, including an acceptable half-life, AUC (area under the curve) and peak values and lacking unfavorable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001) Journal of Virology 75: 4614-4624, which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV.

Anti-HCV compounds encompass agents selected from an HCV polymerase inhibitor, an HCV protease inhibitor, an inhibitor of another target in the HCV life cycle, and immunomodulatory agent, an antiviral agent, and combinations thereof.

HCV polymerase inhibitors include, but are not limited to, NM283 (valopicitabine), R803, JTK-109, JTK-003, HCV-371, HCV-086, HCV-796 and R-1479.

Inhibitors of HCV proteases (NS2-NS3 inhibitors and NS3-NS4A inhibitors) include, but are not limited to, the compounds of WO02/18369 (see, e.g., page 273, lines 9-22 and page 274, line 4 to page 276, line 11); BILN-2061, VX-950, GS-9132 (ACH-806), SCH-503034, and SCH-6. Further agents that can be used are those disclosed in WO98/17679, WO00/056331 (Vertex); WO 98/22496 (Roche); WO 99/07734, (Boehringer Ingelheim), WO 2005/073216, WO 2005073195 (Medivir) and structurally similar agents.

Inhibitors of other targets in the HCV life cycle, including NS3 helicase; metallo-protease inhibitors; antisense oligonucleotide inhibitors, such as ISIS-14803, AVI-4065 and the like; siRNA's such as SIRPLEX-140-N and the like; vector-encoded short hairpin RNA (shRNA); DNAzymes; HCV specific ribozymes such as heptazyme, RPI.13919 and the like; entry inhibitors such as HepeX-C, HuMax-HepC and the like; alpha glucosidase inhibitors such as celgosivir, UT-231B and the like; KPE-02003002; and BIVN 401.

Immunomodulatory agents include, but are not limited to; natural and recombinant interferon isoform compounds, including α-interferon, β-interferon, γ-interferon, ω-interferon and the like, such as Intron A®, Roferon-A®, Canferon-A300®, Advaferon®, Infergen®, Humoferon®, Sumiferon MP®, Alfaferone®, IFN-beta®, Feron® and the like; polyethylene glycol derivatized (pegylated) interferon compounds, such as PEG interferon-α-2a (Pegasys®), PEG interferon-α-2b (PEG-Intron®), pegylated IFN-α-con1 and the like; long acting formulations and derivatizations of interferon compounds such as the albumin-fused interferon albuferon α and the like; compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isatoribine and the like; thymosin α-1; ANA-245; ANA-246; histamine dihydrochloride; propagermanium; tetrachlorodecaoxide; ampligen; IMP-321; KRN-7000; antibodies, such as civacir, XTL-6865 and the like; and prophylactic and therapeutic vaccines such as InnoVac C, HCV E1E2/MF59 and the like.

Other antiviral agents include, but are not limited to, ribavirin, amantadine, viramidine, nitazoxanide; telbivudine; NOV-205; taribavirin; inhibitors of internal ribosome entry; broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, and mycophenolic acid and derivatives thereof, and including, but not limited to VX-950, merimepodib (VX-497), VX-148, and/or VX-944); or combinations of any of the above.

Thus, to combat or treat HCV infections, the compounds of formula (I) may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and another HCV inhibitory compound, e.g. (pegylated) IFN-α and/or ribavirin.

In still another aspect there are provided combinations of a compound of formula (I) as specified herein and an anti-HIV compound. The latter preferably are those HIV inhibitors that have a positive effect on drug metabolism and/or pharmacokinetics that improve bioavailabilty. An example of such an HIV inhibitor is ritonavir.

As such, the present invention further provides a combination comprising (a) an HCV NS3/4a protease inhibitor of formula (I) or a pharmaceutically acceptable salt thereof; and (b) ritonavir or a pharmaceutically acceptable salt thereof.

The compound ritonavir, and pharmaceutically acceptable salts thereof, and methods for its preparation are described in WO94/14436. For preferred dosage forms of ritonavir, see U.S. Pat. No. 6,037,157, and the documents cited therein: U.S. Pat. No. 5,484,801, U.S. Ser. No. 08/402,690, and WO95/07696 and WO95/09614. Ritonavir has the following formula:

In one embodiment of the present invention there is provided a pharmaceutical composition comprising a combination according to any one of the embodiments described herein and a pharmaceutically acceptable excipient. In particular, the present invention provides a pharmaceutical composition comprising (a) a therapeutically effective amount of an HCV NS3/4a protease inhibitor of the formula (I) or a pharmaceutically acceptable salt thereof, (b) a therapeutically effective amount of ritonavir or a pharmaceutically acceptable salt thereof, and (c) a pharmaceutically acceptable excipient. Optionally, the pharmaceutical composition further comprises an additional agent selected from an HCV polymerase inhibitor, an HCV protease inhibitor, an inhibitor of another target in the HCV life cycle, and immunomodulatory agent, an antiviral agent, and combinations thereof.

The compositions may be formulated into suitable pharmaceutical dosage forms such as the dosage forms described above. Each of the active ingredients may be formulated

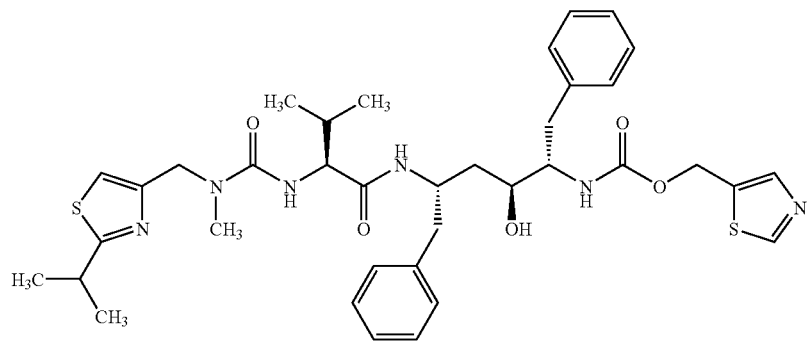

In a further embodiment, the combination comprising (a) an HCV NS3/4a protease inhibitor of formula (I) or a pharmaceutically acceptable salt thereof; and (b) ritonavir or a pharmaceutically acceptable salt thereof, further comprises an additional anti-HCV compound selected from the compounds as described herein.

In one embodiment of the present invention there is provided a process for preparing a combination as described herein, comprising the step of combining an HCV NS3/4a protease inhibitor of formula (I) or a pharmaceutically acceptable salt thereof, and ritonavir or a pharmaceutically acceptable salt thereof. An alternative embodiment of this invention provides a process wherein the combination comprises one or more additional agent as described herein.

The combinations of the present invention may be used as medicaments. Said use as a medicine or method of treatment comprises the systemic administration to HCV-infected subjects of an amount effective to combat the conditions associated with HCV and other pathogenic flavi- and pestiviruses. Consequently, the combinations of the present invention can be used in the manufacture of a medicament useful for treating, preventing or combating infection or disease associated with HCV infection in a mammal, in particular for treating conditions associated with HCV and other pathogenic flavi- and pestiviruses.

separately and the formulations may be co-administered or one formulation containing both and if desired further active ingredients may be provided.

As used herein, the term "composition" is intended to encompass a product comprising the specified ingredients, as well as any product which results, directly or indirectly, from the combination of the specified ingredients.

In one embodiment the combinations provided herein may also be formulated as a combined preparation for simultaneous, separate or sequential use in HIV therapy. In such a case, the compound of general formula (I) or any subgroup thereof, is formulated in a pharmaceutical composition containing other pharmaceutically acceptable excipients, and ritonavir is formulated separately in a pharmaceutical composition containing other pharmaceutically acceptable excipients. Conveniently, these two separate pharmaceutical compositions can be part of a kit for simultaneous, separate or sequential use.

Thus, the individual components of the combination of the present invention can be administered separately at different times during the course of therapy or concurrently in divided or single combination forms. The present invention is therefore to be understood as embracing all such regimes of simultaneous or alternating treatment and the term "administering"

is to be interpreted accordingly. In a preferred embodiment, the separate dosage forms are administered about simultaneously.

In one embodiment, the combination of the present invention contains an amount of ritonavir, or a pharmaceutically acceptable salt thereof, which is sufficient to clinically improve the bioavailability of the HCV NS3/4a protease inhibitor of formula (I) relative to the bioavailability when said HCV NS3/4a protease inhibitor of formula (I) is administered alone.

In another embodiment, the combination of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

A further embodiment relates to a method for improving the bioavailability of a HCV NS3/4a protease inhibitor comprising administering to an individual in need of such improvement a combination as defined herein, comprising a therapeutically effective amount of each component of said combination.

In a further embodiment, the invention relates to the use of ritonavir or a pharmaceutically acceptable salt thereof, as an improver of at least one of the pharmacokinetic variables of a HCV NS3/4a protease inhibitor of formula (I) selected from $t_{1/2}$, $C_{min}$, $C_{max}$, $C_{ss}$, AUC at 12 hours, or AUC at 24 hours; with the proviso that said use is not practised in the human or animal body.

The term "individual" as used herein refers to an animal, preferably a mammal, most preferably a human, who has been the object of treatment, observation or experiment. Bioavailability is defined as the fraction of administered dose reaching systemic circulation. $t_{1/2}$ represents the half life or time taken for the plasma concentration to fall to half its original value. $C_{ss}$ is the steady state concentration, i.e. the concentration at which the rate of input of drug equals the rate of elimination. $C_{min}$ is defined as the lowest (minimum) concentration measured during the dosing interval. $C_{max}$, represents the highest (maximum) concentration measured during the dosing interval. AUC is defined as the area under the plasma concentration-time curve for a defined period of time.

The combinations of this invention can be administered to humans in dosage ranges specific for each component comprised in said combinations. The components comprised in said combinations can be administered together or separately. The NS3/4a protease inhibitors of formula (I) or any subgroup thereof, and ritonavir or a pharmaceutically acceptable salt or ester thereof, may have dosage levels of the order of 0.02 to 5.0 grams-per-day.

When the HCV NS3/4a protease inhibitor of formula (I) and ritonavir are administered in combination, the weight ratio of the HCV NS3/4a protease inhibitor of formula (I) to ritonavir is suitably in the range of from about 40:1 to about 1:15, or from about 30:1 to about 1:15, or from about 15:1 to about 1:15, typically from about 10:1 to about 1:10, and more typically from about 8:1 to about 1:8. Also useful are weight ratios of the HCV NS3/4a protease inhibitors of formula (I) to ritonavir ranging from about 6:1 to about 1:6, or from about 4:1 to about 1:4, or from about 3:1 to about 1:3, or from about 2:1 to about 1:2, or from about 1.5:1 to about 1:1.5. In one aspect, the amount by weight of the HCV NS3/4a protease inhibitors of formula (I) is equal to or greater than that of ritonavir, wherein the weight ratio of the HCV NS3/4a protease inhibitor of formula (I) to ritonavir is suitably in the range of from about 1:1 to about 15:1, typically from about 1:1 to about 10:1, and more typically from about 1:1 to about 8:1. Also useful are weight ratios of the HCV NS3/4a protease inhibitor of formula (I) to ritonavir ranging from about 1:1 to about 6:1, or from about 1:1 to about 5:1, or from about 1:1 to about 4:1, or from about 3:2 to about 3:1, or from about 1:1 to about 2:1 or from about 1:1 to about 1.5:1.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated.

Since the instant invention refers to combinations comprising two or more agents, the "therapeutically effective amount" is that amount of the agents taken together so that the combined effect elicits the desired biological or medicinal response. For example, the therapeutically effective amount of a composition comprising (a) the compound of formula (I) and (b) ritonavir, would be the amount of the compound of formula (I) and the amount of ritonavir that when taken together have a combined effect that is therapeutically effective.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as one, two, three, four or more (sub-)doses at appropriate intervals throughout the day. Said (sub-)doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

According to one embodiment, the HCV NS3/4a protease inhibitor of formula (I) and ritonavir may be co-administered once or twice a day, preferably orally, wherein the amount of the compounds of formula (I) per dose is from about 1 to about 2500 mg, and the amount of ritonavir per dose is from 1 to about 2500 mg. In another embodiment, the amounts per dose for once or twice daily co-administration are from about 50 to about 1500 mg of the compound of formula (I) and from about 50 to about 1500 mg of ritonavir. In still another embodiment, the amounts per dose for once or twice daily co-administration are from about 100 to about 1000 mg of the compound of formula (I) and from about 100 to about 800 mg of ritonavir. In yet another embodiment, the amounts per dose for once or twice daily co-administration are from about 150 to about 800 mg of the compound of formula (I) and from about 100 to about 600 mg of ritonavir. In yet another embodiment, the amounts per dose for once or twice daily co-administration are from about 200 to about 600 mg of the compound of formula (I) and from about 100 to about 400 mg of ritonavir. In yet another embodiment, the amounts per dose for once or twice daily co-administration are from about 200 to about 600 mg of the compound of formula (I) and from about 20 to about 300 mg of ritonavir. In yet another embodiment, the amounts per dose for once or twice daily co-administration are from about 100 to about 400 mg of the compound of formula (I) and from about 40 to about 100 mg of ritonavir.

Exemplary combinations of the compound of formula (I) (mg)/ritonavir (mg) for once or twice daily dosage include 50/100, 100/100, 150/100, 200/100, 250/100, 300/100, 350/100, 400/100, 450/100, 50/133, 100/133, 150/133, 200/133, 250/133, 300/133, 50/150, 100/150, 150/150, 200/150, 250/150, 50/200, 100/200, 150/200, 200/200, 250/200, 300/200, 50/300, 80/300, 150/300, 200/300, 250/300, 300/300, 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200. Other exemplary combinations of the compound of formula (I) (mg)/ritonavir (mg) for once or twice daily dosage include 1200/400, 800/400, 600/400, 400/200, 600/200, 600/100, 500/100, 400/50, 300/50, and 200/50.

In one embodiment of the present invention there is provided an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, or a combination according to the invention combining an HCV NS3/4a protease inhibitor of formula (I) or a pharmaceutically acceptable salt thereof, and ritonavir or a pharmaceutically acceptable salt thereof, in an amount effective for use as a standard or reagent in a test or assay for determining the ability of potential pharmaceuticals to inhibit HCV NS3/4a protease, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto.

General: LC/MS analyses were performed on a Waters Alliance 2795 HT attached to a Micromass ZMD mass spectrometer using electrospray ionisation in positive mode.

Eluent: A: water, 0.1% TFA, B: acetonitrile, 0.1% TFA. Detection: UV (diode array: 210-300 nm). Gradients: Method A: 20 to 70% B in A (1.5 ml min$^{-1}$) over 5 min.

Method B: 30 to 80% B in A (1.5 ml min$^{-1}$) over 5 min.
Method C: 40 to 80% B in A (1.5 ml min$^{-1}$) over 5 min.
Method D: 50 to 90% B in A (1.5 ml min$^{-1}$) over 5 min.

Method E: 20 to 70% B in A (0.9 ml min$^{-1}$) over 2.5 min.
Method F: 30 to 80% B in A (0.9 ml min$^{-1}$) over 2.5 min.
Method G: 40 to 80% B in A (0.9 ml min$^{-1}$) over 2.5 min.

Method H: 50 to 90% B in A (0.9 ml min$^{-1}$) over 2.5 min. Column: Methods A-D: Phenomonex, Synergi MAX RP-80A column (5.0 cm, 4.6 mm φ, 4 μm). Methods E-H: Phenomonex, Synergi MAX RP-80A column (3.0 cm, 3.0 mm φ, 4 μm).

Example 1

Preparation of 1-[(3-Oxo-2-oxa-bicyclo[2.2.1]heptane-5-carbonyl)-amino]-2-vinyl-cyclopropane carboxylic acid ethyl ester (3)

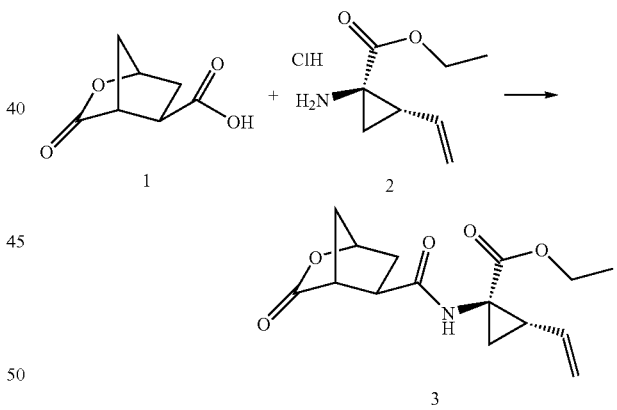

To a solution of 1 (857 mg, 5.5 mmol), in DMF (14 ml) and DCM (25 ml) at room temperature, was added 2 (1.15 g, 6.0 mmol), HATU (2.29 g, 6.0 mmol) and DIPEA (3.82 ml, 22 mmol). The reaction was stirred under N$_2$-atmosphere at ambient temperature for 1 h. LC/MS analysis showed complete conversion, and the reaction mixture was concentrated in vacuo. The residue was re-dissolved in DCM (100 ml) and 0.1 M HCl (aqueous) and the layers separated. The organic phase was washed with NaHCO$_3$ (aqueous) and brine, dried (MgSO$_4$) and filtered. Removal of the solvent in vacuo afforded the target compound 3 (1.6 g, 99%). LC/MS (Method A): t$_R$=2.46 min, >95%, m/z (ESI$^+$)=294 (MH$^+$)

Example 2

Preparation of 2-(1-Ethoxycarbonyl-2-vinylcyclopropylcarbamoyl)-4-hydroxy-cyclopentane carboxylic acid diisopropylethylamine salt (4)

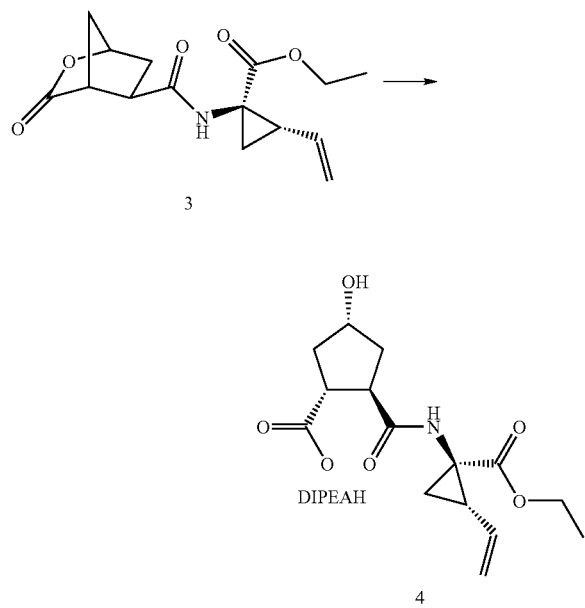

To a solution of 3 (800 mg, 2.73 mmol) in water (15 ml) in a 20 ml microwave reaction vessel was added DIPEA (1.2 ml, 6.8 mmol) and a stir bar. The reaction vessel was sealed and the immiscible slurry was shaken vigorously before insertion in the microwave cavity. After 1 min of pre-stirring, the reaction was irradiated for 40 min to a set temperature of 100° C. After cooling to 40° C., the transparent solution was concentrated in vacuo, and the residual brown oil co-evaporated 3 times with acetonitrile to remove any residual water. The crude product 4, in the form of a DIPEA salt, was immediately taken forward to the next step. LC/MS (Method A): $t_R$=1.29 min, >95%, m/z (ESI$^+$)=312 (MH$^+$).

Example 3

Preparation of 1-{[2-(Hex-5-enylmethylcarbamoyl)-4-hydroxycyclo-pentanecarbonyl]amino}-2-vinylcyclopropane carboxylic acid ethyl ester (6)

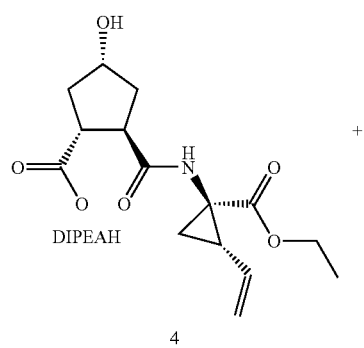

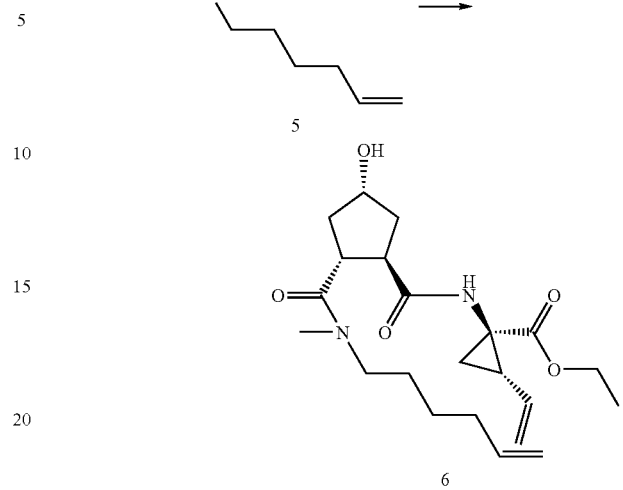

The crude compound 4 (5.5 mmol) was dissolved in DCM (50 ml) and DMF (14 ml) followed by addition of HATU (2.09 g, 5.5 mmol), 5 (678 mg, 6.0 mmol) and DIPEA (3.08 ml, 17.5 mmol) at room temperature. The reaction was stirred at ambient temperature for 1 h. LC/MS analysis showed complete conversion and the reaction mixture was concentrated in vacuo. The residue was re-dissolved in ethyl acetate (100 ml) and the organic layer washed with 0.1 M HCl (aqueous), K$_2$CO$_3$ (aqueous) and brine, dried (MgSO$_4$) and filtered. Evaporation of the solvent in vacuo gave an oil which was purified by flash chromatography (Silica, ethyl acetate/methanol) to afford the target compound 6 (1.65 g, 74%). TLC (Silica): methanol/ethyl acetate 5:95, R$_f$=0.5; LC/MS (Method A): $t_R$=3.44 min, >95%, m/z (ESI$^+$)=407 (MH$^+$).

Example 4

Preparation of 1-{[2-(Hex-5-enylmethylcarbamoyl)-4-hydroxycyclo-pentanecarbonyl]amino}-2-vinylcyclopropanecarboxylic acid (7)

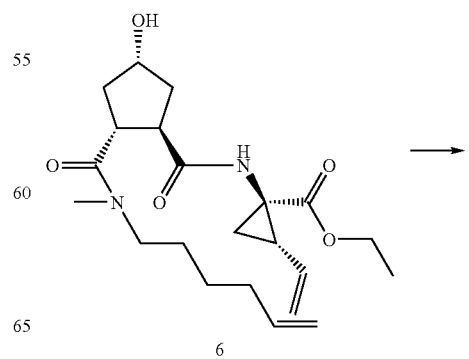

-continued

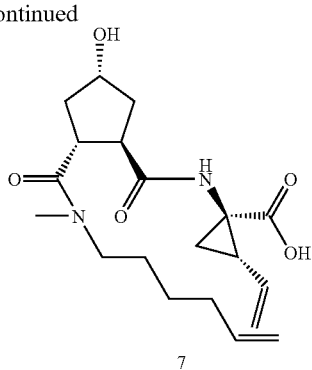

7

Compound 6 (493 mg, 1.21 mmol) was dissolved in DMF (1 ml) and transferred to a 20 ml microwave reaction vessel. Then, aqueous LiOH (2 M, 10.5 ml) and a stirbar were added. The reaction vessel was sealed and the immiscible slurry was shaken vigorously before insertion in the microwave cavity. The reaction was irradiated for 30 min to 130° C. The reaction mixture was cooled to 40° C. and the clear solution acidified to pH 2 with aqueous HCl (1 M, 24 ml) and extracted 3 times with ethyl acetate (20 ml). The pooled organic layers were washed with brine, dried (MgSO$_4$) and filtered. The solvent was evaporated in vacuo to afford compound 7 (410 mg, 90%). LC/MS (Method A): t$_R$=2.46 min, >95%, m/z (ESI$^+$)= 379 (MH$^+$).

Example 5

Preparation of 4-Hydroxy-cyclopentane-1,2-dicarboxylic acid 1-[(1-cyclopropanesulfonylamino carbonyl-2-vinyl-cyclopropyl)-amide] 2-(hex-5-enylmethyl-amide) (8)

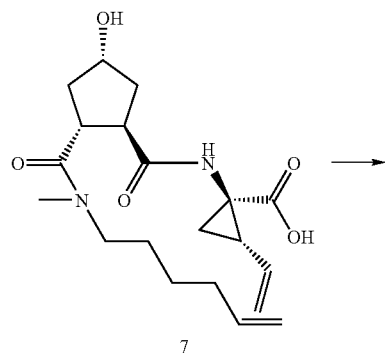

The crude acid 7 (410 mg, 1.09 mmol) was dissolved in DMF (1.5 ml) and DCM (4.5 ml) followed by addition of EDAC (417 mg, 2.18 mmol) at room temperature. The mixture was allowed to incubate with stirring at room temperature. After 10 min, DMAP (133 mg, 1.09 mmol) was added followed by another 20 min incubation at room temperature. Subsequently, a pre-mixed solution of cyclopropanesulfonic acid amide (527 mg, 4.36 mmol) and DBU (663 mg, 4.36 mmol) in DMF (2 ml) and DCM (2 ml) was added followed by heating in the microwave to 100° C. for 30 min. The resulting red solution was concentrated in vacuo and re-dissolved in ethyl acetate (20 ml). The organic phase was washed with 1 M HCl (aqueous) (3×10 ml) and brine (10 ml), dried (MgSO$_4$) and filtered. The solvent was evaporated in vacuo to yield the crude sulfonamide which was further purified by chromatography (Silica, ethyl acetate/methanol, 97.5:2.5) to afford the target compound 8 (403 mg, 77%); LC/MS (Method A): t$_R$=3.31 min, >95%, m/z (ESI$^+$)=482 (MH$^+$).

Introduction of P2 Carbamate

Example 6-1

Procedure A for carbamate formation, exemplified with synthesis of (2-Piperidin-1-ylphenyl)carbamic acid 3-(1-cyclopropanesulfonylaminocarbonyl-2-vinylcyclopropylcarbamoyl)-4-(hex-5-enylmethyl-carbamoyl)cyclopentyl ester (10)

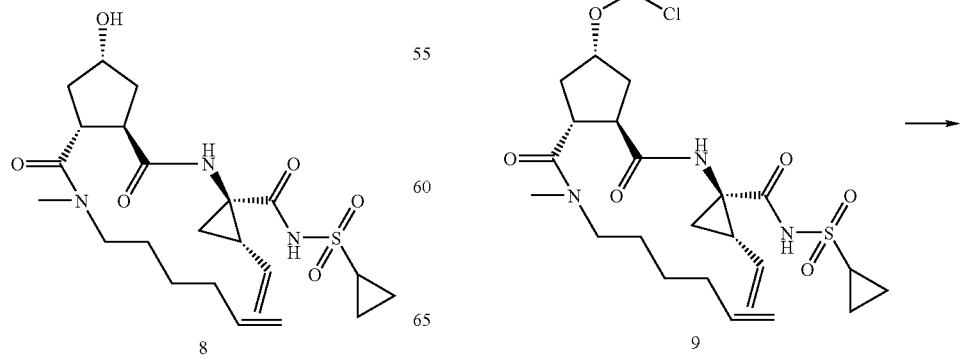

-continued

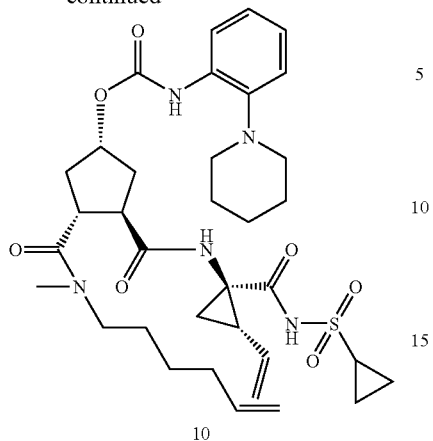

10

Compound 8 (19.4 mg, 40 μmol) was dissolved in DCM (1.8 ml) followed by addition of solid NaHCO$_3$ (14 mg, 160 μmol) and a stirbar. To this slurry was then added phosgene in toluene (1.93 M, 430 μl, 0.8 mmol) and the mixture stirred vigorously for 2 h to afford the chloroformate 9. LC/MS (Method G): t$_R$=2.65 min, >95%, m/z (ESI$^+$)=544 (MH$^+$). The solvent was evaporated in vacuo and the residue was co-evaporated 3 times with DCM to remove any residual phosgene.

The afforded chloroformate 9 was subsequently re-dissolved in DCM (1 ml) and 2-piperidin-1-ylaniline (12 mg, 68 μmol) was added. The mixture was allowed to stir at ambient temperature for 2 h after which time LC/MS showed complete conversion.

Then, DCM (1 ml) was added and the resulting solution was washed twice with 1 M HCl (aqueous), NaHCO$_3$ (aqueous) and brine. The organic phase was dried (MgSO$_4$) and filtered. Evaporation of the solvent in vacuo gave a crude which was further purified by preparative LC/MS to afford compound 10 (23.3 mg, 85%); LC/MS (Method G): t$_R$=1.49 min, >95%, m/z (ESI$^+$)=684 (MH$^+$).

Example 6-2
Preparation of [2-(3-Methylpyrazol-1-yl)-5-trifluoromethylphenyl]-carbamic acid 3-(1-cyclopropanesulfonylaminocarbonyl-2-vinylcyclopropyl-carbamoyl)-4-(hex-5-enylmethylcarbamoyl)cyclopentyl ester (15)

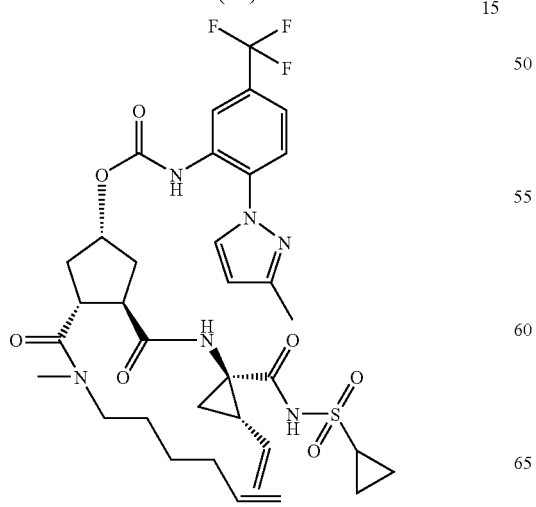

15

The title compound was synthesized from 2-(3-methylpyrazol-1-yl)-5-trifluoromethyl-aniline according to the procedure described in Example 6-1. LC/MS (Method H): t$_R$=2.20 min, >95%, m/z (ESI$^+$)=749 (MH$^+$).

Example 6-3

Preparation of (2-Pyrazol-1-yl-5-trifluoromethylphenyl)carbamic acid 3-(1-cyclopropane sulfonyl-aminocarbonyl-2-vinylcyclopropylcarbamoyl)-4-(hex-5-enyl-methyl-carbamoyl)-cyclopentyl ester (16)

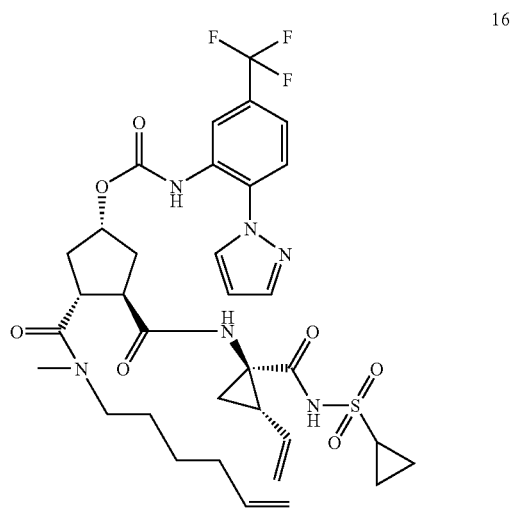

16

The title compound was synthesized from 2-pyrazol-1-yl-5-trifluoromethylaniline according to the procedure described in Example 6-1. LC/MS (Method H): t$_R$=2.0 min, >95%, m/z (ESI$^+$)=735 (MH$^+$).

Example 6-4

Preparation of [2-(5-Methylpyrazol-1-yl)-5-trifluoromethylphenyl]-carbamic acid 3-(1-cyclopropanesulfonylaminocarbonyl-2-vinylcyclopropyl-carbamoyl)-4-(hex-5-enylmethyl-carbamoyl)cyclopentyl ester (17)

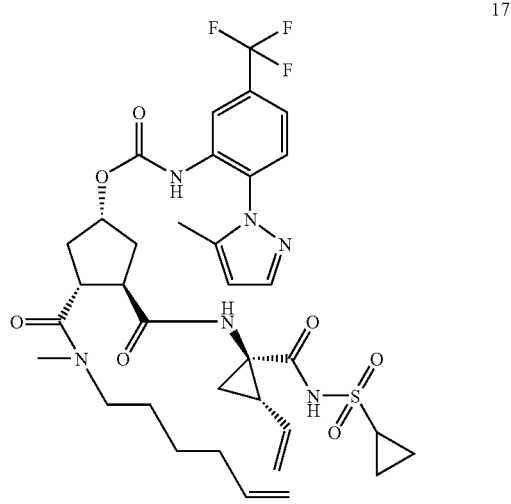

17

The title compound was synthesized from 2-(5-methylpyrazol-1-yl)-5-trifluoromethyl-aniline according to the procedure described in Example 6-1. LC/MS (Method H): $t_R$=1.93 min, >95%, m/z (ESI$^+$)=749 (MH$^+$). Example 6-5

Preparation of [5-Fluoro-2-(3-methylpyrazol-1-yl)phenyl]carbamic acid 3-(1-cyclopropane sulfonylaminocarbonyl-2-vinylcyclopropylcarbamoyl)-4-(hex-5-enylmethyl-carbamoyl)cyclopentyl ester (18)

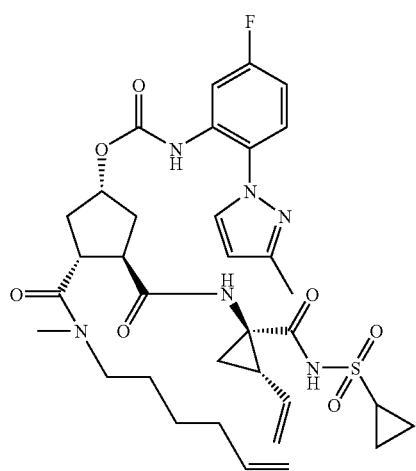

The title compound was synthesized from 5-fluoro-2-(3-methyl-pyrazol-1-yl)aniline according to the procedure described in Example 6-1. LC/MS (Method H): $t_R$=1.76 min, >90%, m/z (ESI$^+$)=699 (MH$^+$).

Example 7-1

Procedure B for carbamate formation, exemplified with synthesis of biphenyl-2-ylcarbamic acid 3-(1-cyclopropanesulfonylaminocarbonyl-2-vinyl-cyclopropylcarbamoyl)-4-(hex-5-enylmethylcarbamoyl)cyclopentyl ester (19)

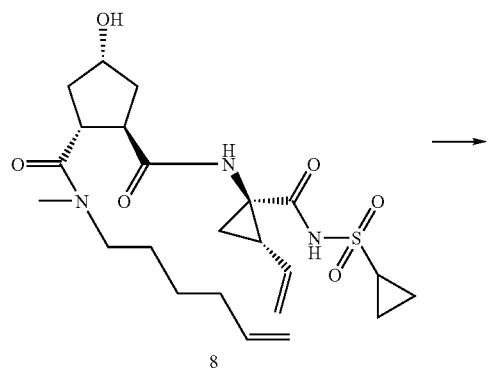

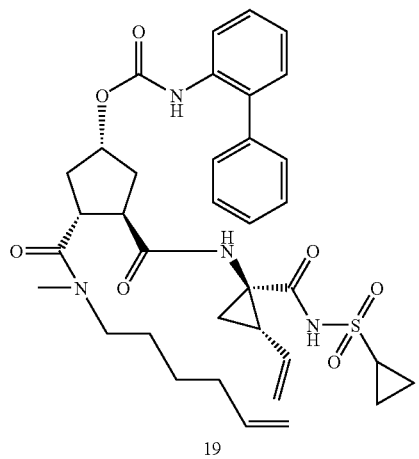

Compound 8 (48.5 mg, 0.1 mmol) was dissolved in dried THF (5 ml) and to this solution was added KOBu$^t$ (45 mg, 0.4 mmol) causing the reaction to turn yellow and to form a precipitate. After 1 min, 2-isocyanatobiphenyl (21.5 mg, 0.11 mmol) was added and the reaction was stirred at ambient temperature for 1 h. LC/MS analysis showed complete carbamoylation. The reaction was quenched by addition of NH$_4$Cl (aqueous) (5 ml), then ethyl acetate (5 ml) was added and the layers separated. The organic layer was subsequently washed with 1 M HCl (aqueous) and brine, dried (MgSO$_4$) and filtered. Evaporation of the solvent in vacuo afforded a crude, which was further purified by preparative LC/MS to afford compound 19 (66 mg, 97%). LC/MS (Method D): $t_R$=2.88 min, >90%, m/z (ESI$^+$)=677 (MH$^+$).

Example 7-2

Preparation of (2-Fluorophenyl)carbamic acid 3-(1-cyclopropane-sulfonylaminocarbonyl-2-vinylcyclopropylcarbamoyl)-4-(hex-5-enylmethyl-carbamoyl)cyclopentyl ester (20)

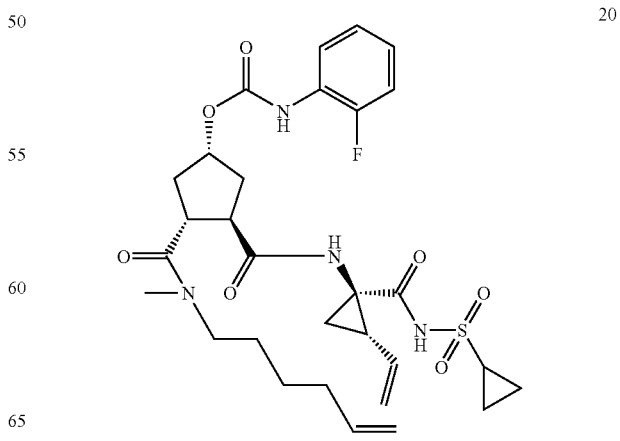

The title compound was synthesized from 1-fluoro-2-isocyanatobenzene according to the procedure described in Example 7-1. LC/MS (Method D): $t_R$=2.21 min, >90%, m/z (ESI$^+$)=619 (MH$^+$).

Example 8-1

Procedure C for carbamate formation, exemplified with synthesis of 2-[3-(1-Cyclopropanesulfonylaminocarbonyl-2-vinylcyclopropylcarbamoyl)-4-(hex-5-enylmethylcarbamoyl)cyclopentyloxycarbonylamino]benzoic acid ethyl ester (23)

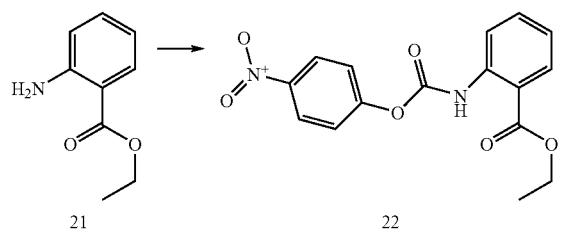

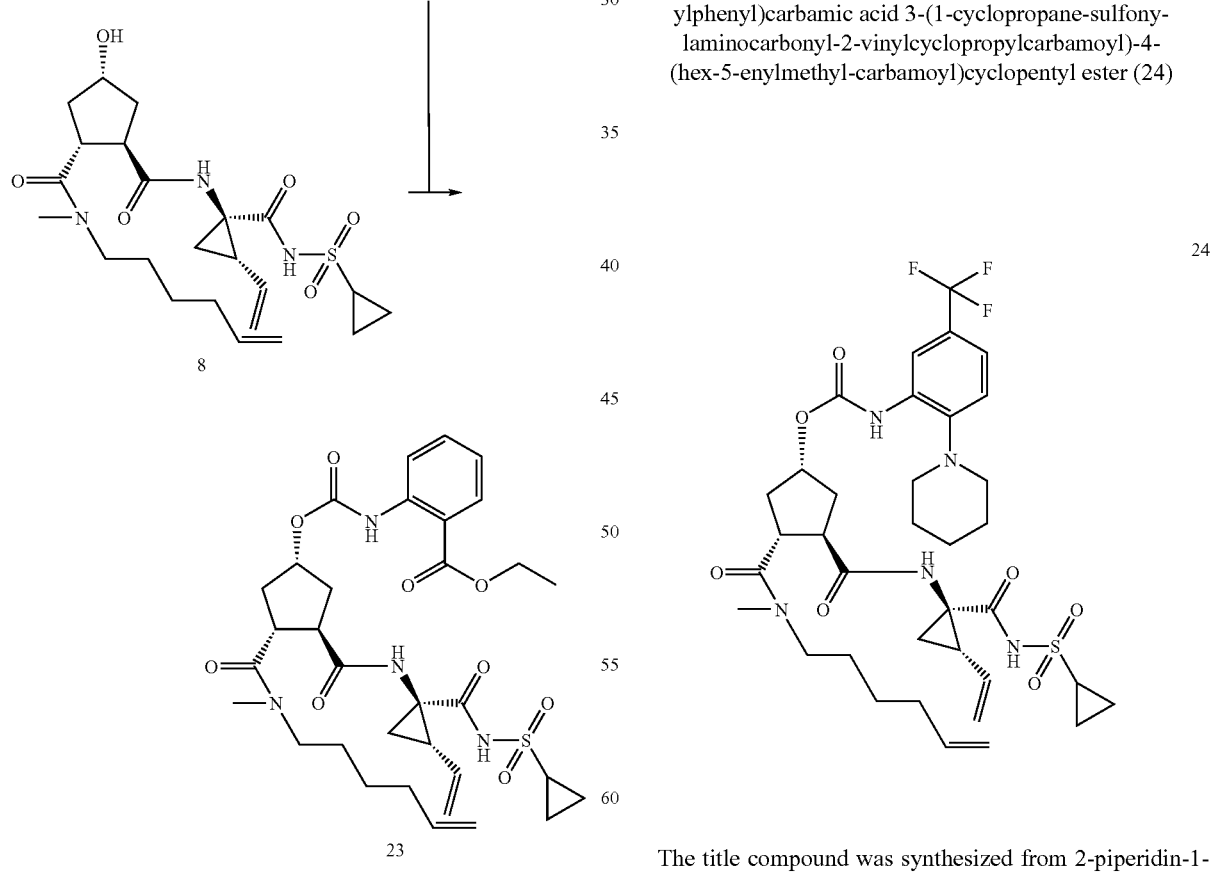

p-Nitrophenyl chloroformate (25.9 mg, 0.129 mmol) was dissolved in acetonitrile (1 mL). To this solution was added solid NaHCO$_3$ (15.7 mg, 0.19 mmol) and the suspension was cooled in an ice/water bath. To the cooled solution was then added a solution of ethyl anthranilate 21 (18.2 μL, 0.123 mmol) in acetonitrile (0.5 ml) and the reaction was allowed to incubate at ambient temperature for 2 h. LC/MS analysis showed complete conversion to compound 22. LC/MS (Method D): $t_R$=3.11 min, >95%, m/z (ESI$^+$)=331 (MH$^+$). This solution was then added to a mixture of 8 (49.2 mg, 102 μmol) and NaH (60% in oil) (4.5 mg, 112 μmol) followed by heating of the reaction to 50° C. for 1 h. LC/MS analysis showed complete disappearance of intermediate 22. The reaction was quenched with NH$_4$Cl (aqueous) (5 ml) and ethyl acetate was added (5 ml). The organic layer was washed with 1 M HCl (aqueous) and brine, dried (MgSO$_4$) and filtered. Evaporation of the solvent gave an oil which was further purified using preparative LC/MS to afford compound 23. (5.9 mg, 8%). LC/MS (Method D): $t_R$=3.29 min, >95%, m/z (ESI$^+$)=673 (MH$^+$).

Example 8-2

Preparation of (2-Piperidin-1-yl-5-trifluoromethylphenyl)carbamic acid 3-(1-cyclopropane-sulfonylaminocarbonyl-2-vinylcyclopropylcarbamoyl)-4-(hex-5-enylmethyl-carbamoyl)cyclopentyl ester (24)

The title compound was synthesized from 2-piperidin-1-yl-5-trifluoromethylaniline according to the procedure described in Example 8-1. LC/MS (Method D): $t_R$=4.05 min, >95%, m/z (ESI$^+$)=752 (MH$^+$).

Example 9-1

Macrocycle formation by ring-closing metathesis, exemplified with synthesis of (2-Piperidin-1-yl-phenyl)carbamic acid 4-cyclopropanesulfonylaminocarbonyl-13-methyl-2,14-dioxo-3,13-diaza-tricyclo[13.3.0.0$^{4,6}$]octadec-7-en-17-yl ester (26).

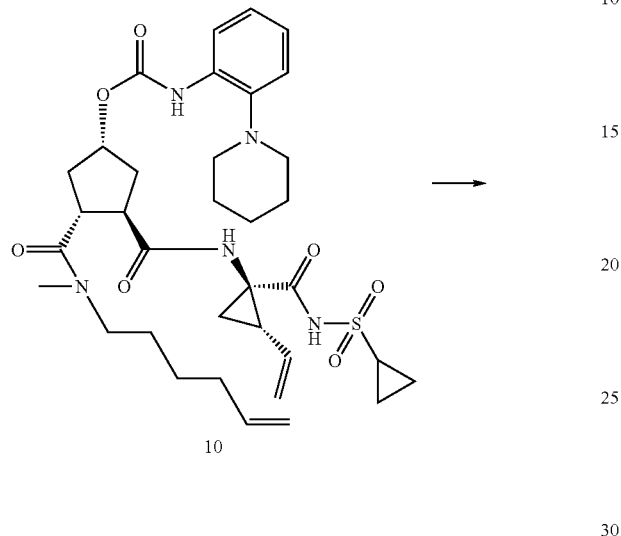

10

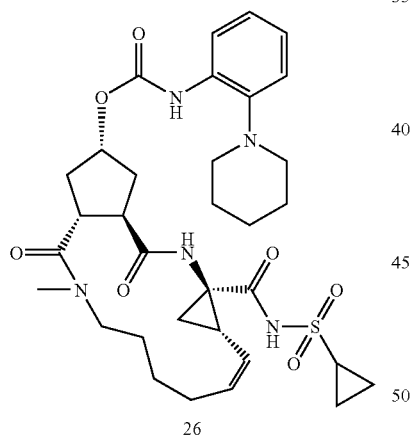

26

Compound 10 (10 mg, 14.6 μmol) was dissolved in DCE (dried over mol sieves, N$_2$-gassed) (10 ml) in a 20 ml microwave reaction vessel with a stir bar. To this solution was added Hoveyda-Grubb's 2$^{nd}$ generation catalyst (2.3 mg, 3.6 μmol) and the reaction vessel was purged with N$_2$(g) and sealed. The reaction was irradiated for 15 min with a set temperature of 150° C. The solvent was removed in vacuo and the residue purified by flash chromatography (Silica; DCM, then 10% methanol in DCM). The product was subsequently purified by preparative LC/MS to afford the target compound 26 (3.4 mg, 36%). LC/MS (Method D): t$_R$=2.21 min, >95%, m/z (ESI$^+$)=656 (MH$^+$).

Example 9-2

Preparation of [2-(3-Methylpyrazol-1-yl)-5-trifluoromethylphenyl]-carbamic acid 4-cyclopropanesulfonylaminocarbonyl-13-methyl-2,14-dioxo-3,13-diaza-tricyclo[13.3.0.0$^{4,6}$]-octadec-7-en-17-yl ester (31).

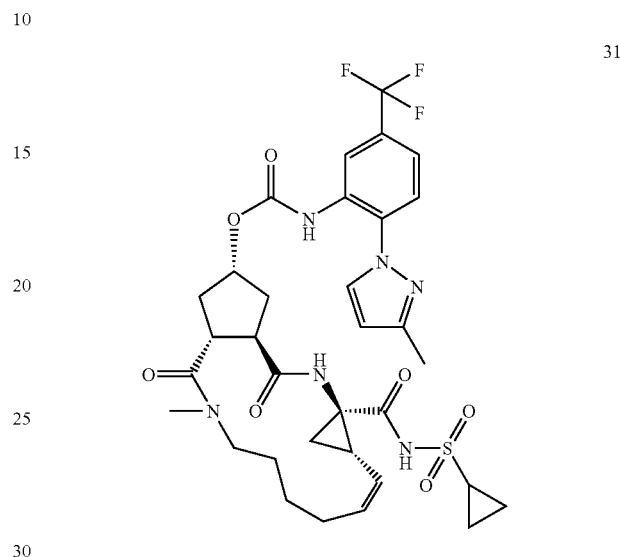

31

Synthesized according to the procedure described in Example 9-1. LC/MS (Method H): t$_R$=1.82 min, >95%, m/z (ESI$^+$)=721 (MH$^+$).

Example 9-3

Preparation of (2-Pyrazol-1-yl-5-trifluoromethylphenyl)carbamic acid 4-cyclopropanesulfonylaminocarbonyl-13-methyl-2,14-dioxo-3,13-diazatricyclo-[13.3.0.0$^{4,6}$]octadec-7-en-17-yl ester (32)

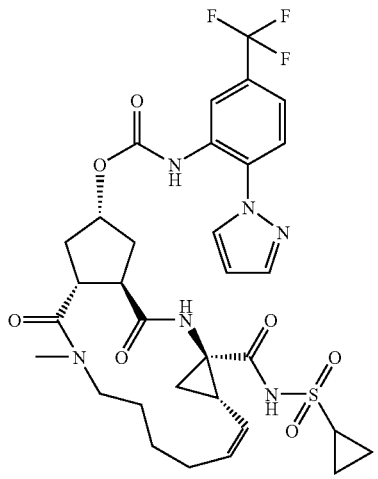

32

Synthesized according to the procedure described in Example 9-1. LC/MS (Method H): $t_R$=1.65 min, >95%, m/z (ESI$^+$)=707 (MH$^+$).

Example 9-4

Preparation of [2-(5-Methyl-pyrazol-1-yl)-5-trifluoromethylphenyl]-carbamic acid 4-cyclopropanesulfonylaminocarbonyl-13-methyl-2,14-dioxo-3,13-diazatricyclo-[13.3.0.0$^{4,6}$]-octadec-7-en-17-yl ester (33)

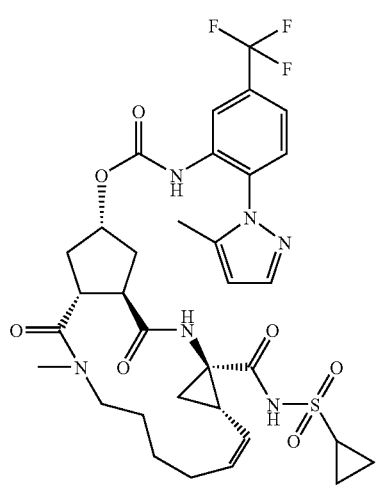

33

Synthesized according to the procedure described in Example 9-1. LC/MS (Method H): $t_R$=1.58 min, >95%, m/z (ESI$^+$)=721 (MH$^+$).

Example 9-5

Preparation of [5-Fluoro-2-(3-methylpyrazol-1-yl)phenyl]carbamic acid 4-cyclopropanesulfonyl-aminocarbonyl-13-methyl-2,14-dioxo-3,13-diazatricyclo-[13.3.0.0$^{4,6}$]-octadec-7-en-17 yl ester (34)

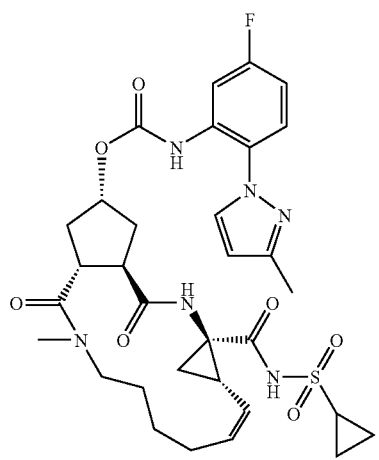

34

Synthesized according to the procedure described in Example 9-1. LC/MS (Method H): $t_R$=1.35 min, >95%, m/z (ESI$^+$)=671 (MH$^+$).

Example 9-6

Preparation of biphenyl-2-yl-carbamic acid 4-cyclopropanesulfonyl-aminocarbonyl-13-methyl-2,14-dioxo-3,13-diaza-tricyclo[13.3.0.0$^{4,6}$]octadec-7-en-17-yl ester (35)

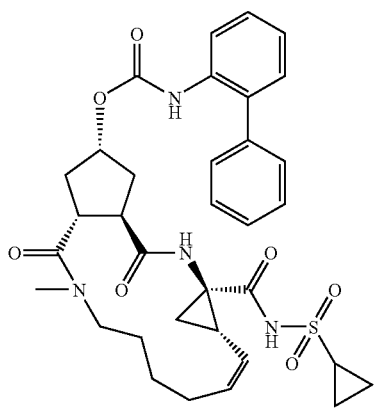

35

Synthesised according to the procedure described in Example 9-1. LC/MS (Method A): $t_R$=4.93 min, >95%, m/z (ESI$^+$)=649 (MH$^+$).

Example 9-7

Preparation of (2-Fluorophenyl)carbamic acid 4-cyclopropanesulfonyl-aminocarbonyl-13-methyl-2,14-dioxo-3,13-diazatricyclo[13.3.0.0$^{4,6}$]octadec-7-en-17-yl ester (36)

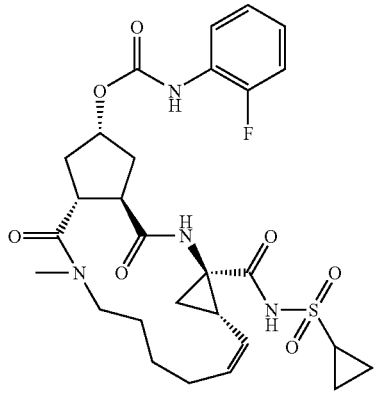

36

Synthesised according to the procedure described in Example 9-1. LC/MS (Method A): $t_R$=2.21 min, >95%, m/z (ESI$^+$)=591 (MH$^+$).

Example 9-8

Preparation of 2-(4-Cyclopropanesulfonylaminocarbonyl-13-methyl-2,14-dioxo-3,13-diaza-tricyclo-[13.3.0.0$^{4,6}$]octadec-7-en-17-yloxycarbonylamino)-benzoic acid ethyl ester (37)

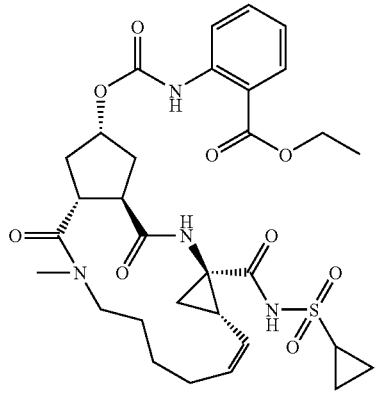

37

Synthesized according to the procedure described in Example 9-1. LC/MS (Method D): $t_R$=2.64 min, >95%, m/z (ESI$^+$)=645 (MH$^+$).

Example 9-9

Preparation of (2-Piperidin-1-yl-5-trifluoromethylphenyl)carbamic acid 4-cyclopropane-sulfonylaminocarbonyl-13-methyl-2,14-dioxo-3,13-diaza-tricyclo-[13.3.0.0$^{4,6}$]octadec-7-en-17-yl ester (38)

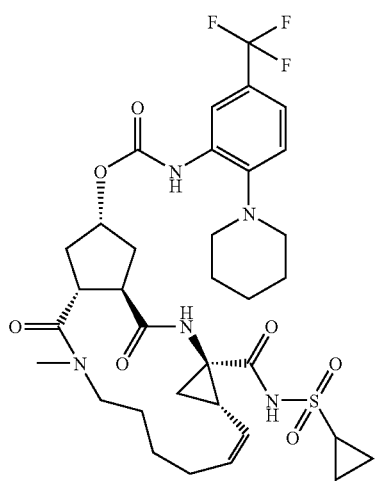

38

Synthesized according to the procedure described in Example 9-1. LC/MS (Method D): $t_R$=3.39 min, >95%, m/z (ESI$^+$)=724 (MH$^+$).

Example 10-1

Procedure for introduction of substituted pyrazoles in ortho-position, exemplified with synthesis of 1-(2-Nitro-4-trifluoromethylphenyl)-1H-pyrazole (41)

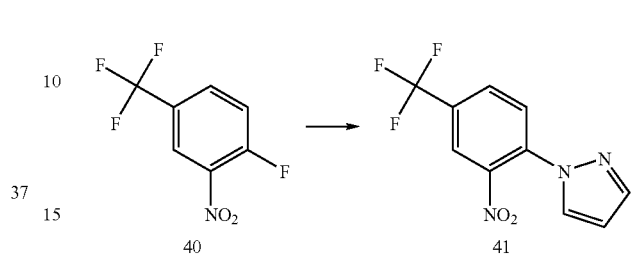

40   41

1-Fluoro-2-nitro-4-trifluoromethylbenzene (209 mg, 1 mmol) was dissolved in ethanol (4.5 ml) in a 5 ml microwave reaction vessel. 1H-pyrazole (83.5 mg, 1.2 mmol), DIPEA (329 µL, 2 mmol) and a stir bar were added followed by sealing of the reaction vessel. The reaction mixture was then heated in the microwave oven for 30 min at 120° C. TLC (Silica; Hexanes/ethyl acetate, 4:1): Rf=0.5 (40), 0.3 (41). The reaction was concentrated in vacuo and the residue purified by flash chromatography (Silica, Hexanes/ethyl acetate) to afford compound 41 (206 mg, 81%). LC/MS (Method F): $t_R$=2.26 min, >95%, m/z (ESI$^+$)=258 (MH$^+$).

Example 10-2

Preparation of 3-Methyl-1-(2-nitro-4-trifluoromethylphenyl)-1H-pyrazole (42)

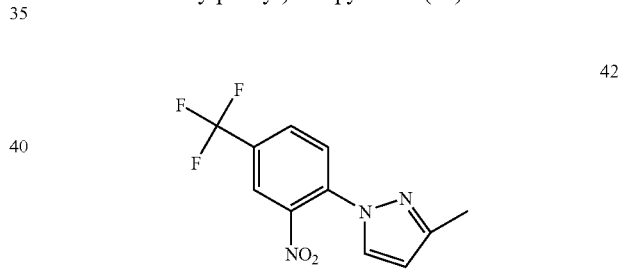

42

The title compound was synthesized from 3-methyl-1H-pyrazole according to the procedure described in Example 10-1. TLC (Silica; Hexanes/ethyl acetate, 4:1): Rf=0.3; LC/MS (Method F): $t_R$=2.28 min, >95%, m/z (ESI$^+$)=272 (MH$^+$).

Example 10-3

Preparation of 5-Methyl-1-(2-nitro-4-trifluoromethylphenyl)-1H-pyrazole (43)

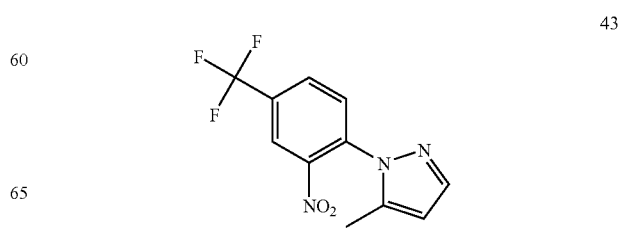

43

The title compound was synthesized from 3-methyl-1H-pyrazole according to the procedure described in Example 10-1. The 3-methyl-1H-pyrazole partially rearranges to 5-methyl-1H-pyrazole during the conditions in Example 10-1. TLC (Silica; Hexane/ethyl acetate, 4:1): Rf=0.4; LC/MS (Method F): $t_R$=2.50 min, >95%, m/z (ESI$^+$)=272 (MH$^+$).

Example 10-4

Preparation of 1-(4-Fluoro-2-nitrophenyl)-3-methyl-1H-pyrazole (44)

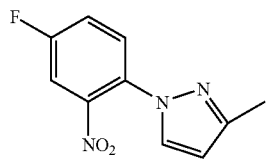

44

The title compound was synthesized from 3-methyl-1H-pyrazole according to the procedure described in Example 10-1. TLC (Silica; Hexane/ethyl acetate, 4:1): Rf=0.3; LC/MS (Method F): $t_R$=1.72 min, >95%, m/z (ESI$^+$)=222 (MH$^+$).

Example 11-1

Procedure for reduction of aromatic nitro groups to afford the P2-anilines, exemplified with synthesis of 2-Pyrazol-1-yl-5-trifluoromethylaniline (45)

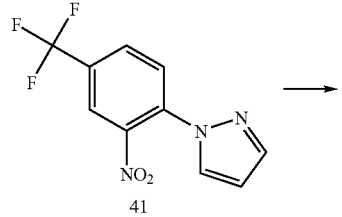

Compound 41 (206 mg, 0.8 mmol) was dissolved in ethanol (25 ml) in a 50 ml flask. Then, 2 spatulas of 5% Pd on activated carbon and a stir bar were added followed by evacuation and N$_2$(g) purging of the flask. H$_2$(g) was then introduced into the flask by a balloon and the reaction stirred at room temperature under H$_2$-atmosphere for 2 h. The H$_2$(g) inlet was closed and the flask evacuated and N$_2$(g) purged 3 times. LC/MS analysis showed complete hydrogenation and the mixture was filtered through a plug of celite before evaporation of the solvent in vacuo to afford the crude aniline 45 (163 mg, 90%). LC/MS (Method F): $t_R$=2.10 min, >95%, m/z (ESI)=228 (MH$^+$).

Example 11-2

Preparation of 2-(3-Methylpyrazol-1-yl)-5-trifluoromethylaniline (46)

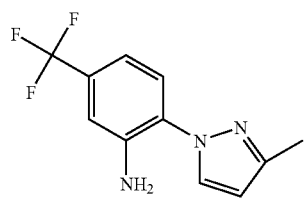

46

Synthesized according to the procedure described in Example 11-1. LC/MS (Method F): $t_R$=1.95 min, >95%, m/z (ESI$^+$)=242 (MH$^+$).

Example 11-3

Preparation of 2-(5-Methylpyrazol-1-yl)-5-trifluoromethylaniline (47)

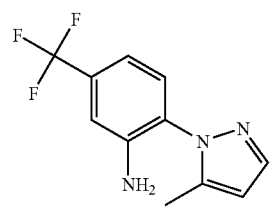

47

Synthesized according to the procedure described in Example 11-1. LC/MS (Method F): $t_R$=2.33 min, >95%, m/z (ESI$^+$)=242 (MH$^+$).

Example 11-4

Preparation of 5-Fluoro-2-(3-methyl-pyrazol-1-yl)aniline (48)

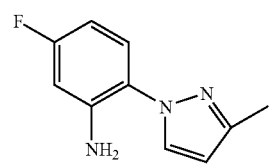

48

Synthesized according to the procedure described in Example 11-1. LC/MS (Method F): $t_R$=1.30 min, >95%, m/z (ESI$^+$)=192 (MH$^+$).

Example 12-1

Preparation of 5-Methyl-2-(2-nitro-4-trifluoromethyl-phenyl)-thiazole (49)

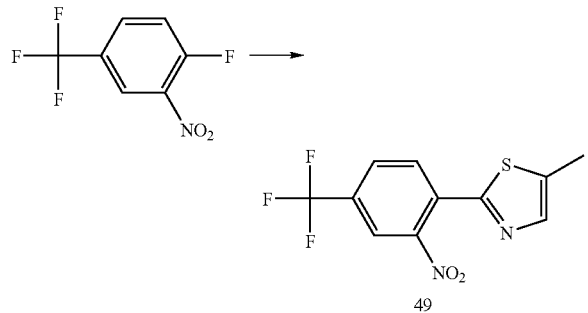

49

A solution of n-BuLi (2.5 mmol) in heptane (c=2.5 M) under nitrogen atmosphere was cooled to −78° C. To the solution was added drop-wise 5-methyl-thiazole (750 mg, 7.5 mmol) dissolved in anhydrous THF (10 ml). The reaction was stirred for 20 min at −78° C. followed by the addition of 1-fluoro-2-nitro-4-trifluoromethyl-benzene (1.56 g, 7.5 mmol) dissolved in anhydrous THF (10 ml). The reaction was stirred for 10 min at −78° C. and then allowed to reach ambient temperature. The reaction was quenched with aqueous sodium bicarbonate and the phases separated. The ether phase was washed with brine, dried with MgSO$_4$ and filtered. The solvent was removed in vacuo and the residue purified by flash chromatography (Silica, Hexane/ethyl acetate) to afford the title compound (620 mg, 29%). LC/MS (Method I): $t_R$=1.44 min, >90%, m/z (ESI$^+$)=289 (MH$^+$).

Example 12-2

Preparation of 4-Methyl-2-(2-nitro-4-trifluoromethyl-phenyl)-thiazole (50)

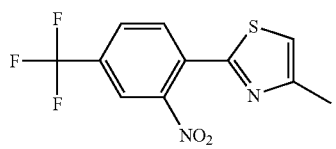

The procedure described in Example 12-1 was followed, but using 4-methyl-thiazole instead of 5-methyl-thiazole, which gave the title compound (495 mg, 23%), LC/MS (Method I): $t_R$=1.40 min, >90%, m/z (ESI$^+$)=289 (MH$^+$).

Example 12-3

Preparation of 4,5-Dimethyl-2-(2-nitro-4-trifluoromethyl-phenyl)-thiazole (51)

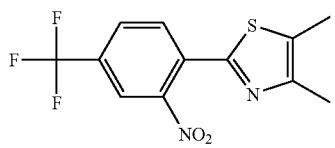

The procedure described in Example 12-1 was followed, but using 4,5-dimethyl-thiazole instead of 5-methyl-thiazole, which gave the title compound (700 mg, 31%), LC/MS (Method I): $t_R$=1.98 min, >90%, m/z (ESI$^+$)=303 (MH$^+$).

Example 13-1

Process for preparation of α-bromo aldehydes and α-bromo ketones exemplified with the synthesis of 1-bromo-3-methyl-butan-2-one (52)

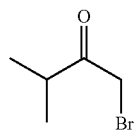

3-methyl-2-butanone (3.2 ml, 30 mmol) was dissolved in absolute ethanol (50 ml) and the solution cooled to −10° C. in an NaCl/ice-bath. To the chilled solution bromine (1.3 ml, 25 mmol) was added drop-wise, keeping the temperature below 2.5° C. The solution was left stirring at subambient temperature for 2 hours, followed by addition of water (25 ml) and additional 20 min of stirring. The product was then extracted with 3 portions of cold petroleum ether. The pooled organic phase was washed 2× with 10% aqueous sodium bicarbonate solution, dried (MgSO$_4$) and filtered. The solvent was removed under reduced pressure to afford the target haloketone, (2.6 g, 63%). H-NMR: CDCl$_3$, δ in ppm 1.17 (d, 6H), 2.97 (m, H), 4.0 (s, 2H).

Example 13-2

Preparation of 2-Bromo-3-methyl-butyraldehyde (53)

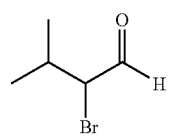

The procedure described in Example 13-1 was followed, but using 3-methyl-butyraldehyde on a 20 mmol scale instead of 3-methyl-2-butanone on a 30 mmol scale, which gave the target haloaldehyde, (2.64 g, 80%).

NMR: CDCl₃, δ in ppm 1.09 (d, 3H), 1.10 (d, 3H), 2.22 (m, H), 4.08 (s, 2H), 9.41 (d, H).

Example 13-3

Preparation of 2-Bromo-butyraldehyde (54)

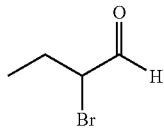

54

The procedure described in Example 13-1 was followed, but using n-butyraldehyde on a 20 mmol scale instead of 3-methyl-2-butanone on a 30 mmol scale, which gave the target α-bromo-aldehyde, (3.0 g, 95%).

NMR: CDCl₃, δ in ppm 1.05 (t, 3H), 2.10 (m, 2H), 4.18 (m, H), 9.43 (d, H).

Example 14-1

Preparation of 2-Nitro-4-trifluoromethyl-thiobenzamide (55)

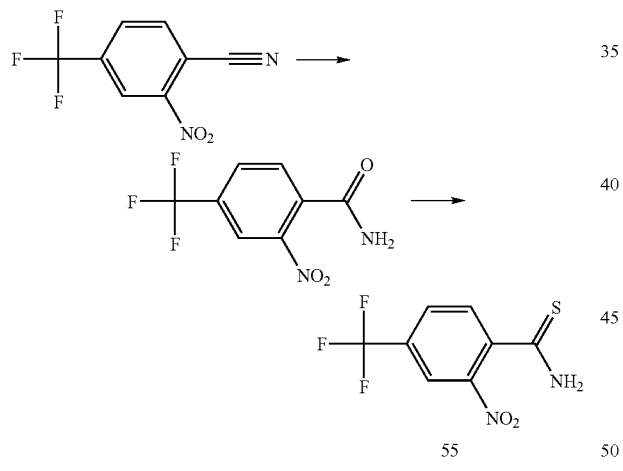

55

2-Nitro-4-trifluoromethyl-benzonitrile (3.9 g, 18 mmol) was dissolved in 70% aqueous H₂SO₄ and the reaction heated to reflux for 3 h. The reaction mixture was slowly poured on ice (300 ml) with vigorous stirring. The solution was filtered and the solid washed with cold water and hexane. The solid material was subsequently redissolved in ethyl acetate and the solution washed with 10% aqueous NaHCO₃ solution, brine, dried (MgSO₄) and filtered. Removal of the solvent in vacuo afforded 2-nitro-4-trifluorobenzamide (4.22 g, 99%). LC/MS (Method F): $t_R$=1.66 min, >95%, m/z (ESI⁺)=218 (M-NH₂)⁺. The afforded benzamide (4.22 g, 18 mmol) was dissolved in dioxane (200 ml) and phosphorous pentasulfide (3.4 g, 15 mmol) was added. The reaction was heated to 110° C. for 4 hours after which time no starting material could be detected.

The solvent was removed in vacuo and the residue partitioned between DCM and 10% aqueous NaHCO₃. The phases were separated and the organic phase was washed with brine, dried (MgSO₄), filtered and concentrated to afford an oil, which was further purified by flash chromatography (Silica, ethyl acetate/hexane) to afford the target thio-benzamide, (3.63 g, 81%). LC/MS: (Method F): $t_R$=2.21 min, >95%, m/z (ESI⁺)= 234 (M-NH₂)⁺.

Example 14-2

Preparation of 4-Methyl-2-nitro-thiobenzamide (56)

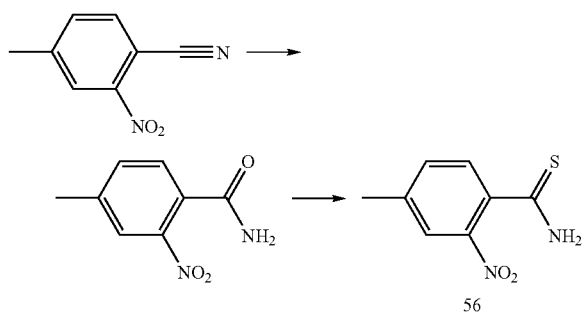

56

The thio-benzamide, was prepared as described in Example 14-1, starting from 4-methyl-2-nitro-benzonitrile via 4-methyl-2-nitro-benzamide which gave the title compound (1.03 g, 98%). LC/MS: (Method I): $t_R$=0.54 min, >80%, m/z (ESI)=180 (M-NH₂)⁺.

Example 15-1

Preparation of 4-Isopropyl-2-(2-nitro-4-trifluoromethyl-phenyl)-thiazole (57)

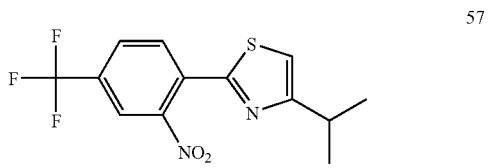

57

2-Nitro-4-trifluoromethyl-thiobenzamide (55), (100 mg, 0.4 mmol) was dissolved in dioxan (4 ml) in a 10 ml test tube and to this solution was added 1-bromo-3-methyl-butan-2-one (52) (72.6 mg, 0.44 mmol). A stirrbar was added and the tube was sealed and heated to 100° C. over night. After cooling to ambient temperature, the vessel was de-capped, the solvent removed in vacuo and the residue partitioned between DCM and 10% aqueous NaHCO₃ solution. The organic phase was separated and washed with additional 10% aqueous NaHCO₃ solution and brine. The organic phase was filtered through a hydrophobic frit and the solvent removed in vacuo

Example 15-2

Preparation of 4-tert-Butyl-2-(2-nitro-4-trifluoromethyl-phenyl)-thiazole (58)

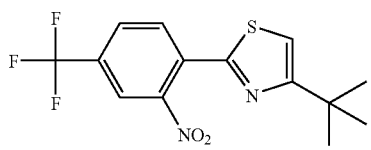

The procedure described in Example 15-1 was followed but using 1-bromo-3,3-dimethyl-butan-2-one instead of 1-bromo-3-methyl-butan-2-one, which gave the title compound (118 mg, 90%). LC/MS: (Method I): $t_R$=2.45 min, >90%, m/z (ESI)=331 (MH$^+$).

Example 15-3

Preparation of 4-Ethyl-2-(2-nitro-4-trifluoromethyl-phenyl)-thiazole (59)

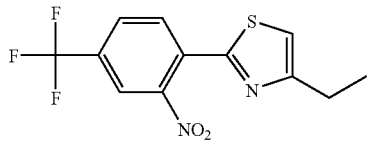

The procedure described in Example 15-1 was followed but using 1-bromo-2-butanone instead of 1-bromo-3-methyl-butan-2-one, which gave the title compound (115 mg, 95%) LC/MS: (Method I): $t_R$=1.91 min, >90%, m/z (ESI$^+$)=303 (MH$^+$).

Example 15-4

Preparation of 5-Ethyl-2-(2-nitro-4-trifluoromethyl-phenyl)-thiazole (60)

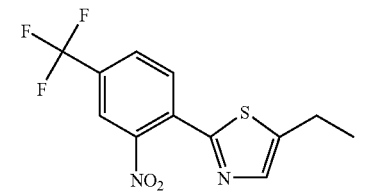

The procedure described in Example 15-1 was followed but using 2-bromo-butyraldehyde (54) instead of 1-bromo-3-methyl-butan-2-one, which gave the title compound (115 mg, 90%). LC/MS: (Method I): $t_R$=1.91 min, >90%, m/z (ESI$^+$)=303 (MH$^+$).

Example 15-5

Preparation of 5-Isopropyl-2-(2-nitro-4-trifluoromethyl-phenyl)-thiazole (61)

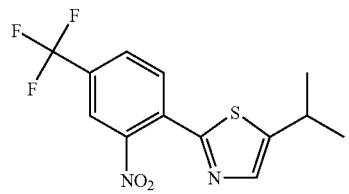

The procedure described in Example 15-1 was followed but using 2-bromo-3-methyl-butyraldehyde (53) instead of 1-bromo-3-methyl-butan-2-one, which gave the title compound (118 mg, 94%). LC/MS: (Method I): $t_R$=2.16 min, >90%, m/z (ESI$^+$)=317 (MH$^+$).

Example 15-6

Preparation of 4-Ethyl-2-(4-methyl-2-nitro-phenyl)-thiazole (62)

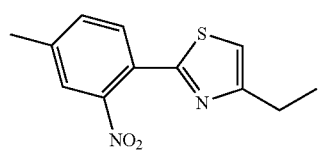

The procedure described in Example 15-1, was followed but 4-methyl-2-nitro-thiobenzamide (56) was used instead of 4-trifluoromethyl-2-nitro-thiobenzamide, and 1-bromo-2-butanone was used instead of 1-bromo-3-methyl-butan-2-one, which gave the title compound (90 mg, 91%). LC/MS: (Method I): $t_R$=1.55 min, >90%, m/z (ESI$^+$)=249 (MH$^+$).

Example 15-7

Preparation of 5-Ethyl-2-(4-methyl-2-nitro-phenyl)-thiazole (63)

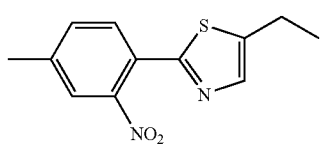

The procedure described in Example 15-1 was followed, except that 4-methyl-2-nitro-thiobenzamide (56) was used instead of 4-trifluoromethyl-2-nitro-thiobenzamide, and 2-bromo-butyraldehyde (54) was used instead of 1-bromo-3- methyl-butan-2-one, which gave the title compound (60 mg, 61%). LC/MS: (Method I): $t_R$=1.52 min, >95%, m/z (ESI$^+$)= 249 (MH$^+$).

Example 15-8

Preparation of 2-(2-nitro-4-trifluoromethyl-phenyl)-thiazole (64)

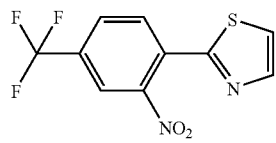
64

The procedure described in Example 15-1 was followed except that bromo-acetaldehyde-dimethylacetal was used instead of 1-bromo-3-methyl-butan-2-one, and the reaction was acid catalysed with 5% acetic acid, which gave the title compound (73 mg, 67%). LC/MS: (Method I): $t_R$=1.31 min, >90%, m/z (ESI$^+$)=275 (MH$^+$).

Example 15-9

Preparation of 2-(4-methyl-2-nitro-phenyl)-thiazole (65)

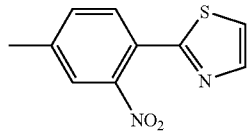
65

The procedure described in Example 15-1 was followed except that 4-methyl-2-nitro-thiobenzamide (56) was used instead of 4-trifluoromethyl-2-nitro-thiobenzamide, bromoacetaldehyde-dimethylacetal was used instead of 1-bromo-3-methyl-butan-2-one, and the reaction was acid catalyst with 5% acetic acid. This gave the title compound (66 mg, 75%). LC/MS: (Method I): $t_R$=0.98 min, >90%, m/z (ESI$^+$)=221 (MH$^+$).

Example 16-1

Procedure A for reduction of aromatic nitro groups, exemplified with the synthesis of 2-(4-Methyl-thiazol-2-yl)-5-trifluoromethyl-phenylamine (66)

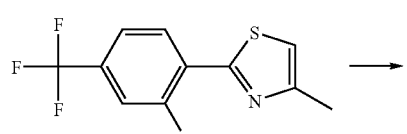
50

-continued

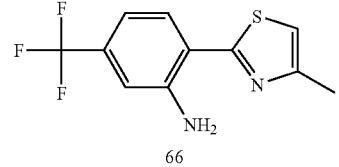
66

Procedure A, described in Example 11-1 was followed, except that 4-methyl-2-(2-nitro-4-trifluoromethyl-phenyl)-thiazole (50) was used instead of 1-(2-nitro-4-trifluoro-methyl-phenyl)-1H-pyrazole. Filtration through a plug of Celite before removal of the solvent in vacuo afforded the crude title compound (163 mg, 90%). LC/MS (Method F): $t_R$=2.10 min, >95%, m/z (ESI$^+$)=228 (MH$^+$).

Example 16-2

Procedure B for reduction of aromatic nitro groups, exemplified with the synthesis of 2-(5-Isopropyl-thiazol-2-yl)-5-trifluoromethyl-phenylamine (67)

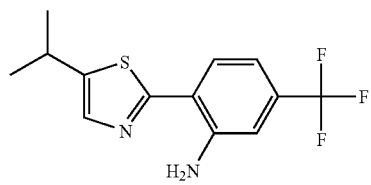
67

5-Isopropyl-2-(2-nitro-4-trifluoromethyl-phenyl)-thiazole (61) (118 mg, 378 µmol) was dissolved in ethanol (3 ml) in a 2-5 ml microwave reaction vessel. To this solution was added ammonium formate (240 mg, 3.8 mmol), PdOH/C (20 wt %) (24 mg, 38 µmol) and a stirrbar. The reaction vessel was sealed and irradiated in the microwave for 40 min at 150° C. The solution was then filtered through a celite plug and concentrated in vacuo. The residue was partitioned between H$_2$O and DCM and filtered through a hydrofobic frit with a Na$_2$SO$_4$-drying cartridge. The filtrated DCM was removed in vacuo to afford the title compound as a yellow solid (98.7 mg, 91%); LC/MS (Method I): $t_R$=2.67 min, >95%, m/z (ESI$^+$)= 287 (MH$^+$).

Example 16-3

Preparation of 2-(5-Methyl-thiazol-2-yl)-5-trifluoromethyl-phenylamine (68)

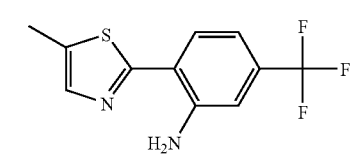
68

Procedure A, described in Example 11-1, was followed except that 5-methyl-2-(2-nitro-4-trifluoromethyl-phenyl)- thiazole (49) was used instead of 1-(2-nitro-4-trifluoro-methyl-phenyl)-1H-pyrazole. Purification by flash-chromatography (Silica; ethyl acetate/Heptane) afforded the title compound (165 mg, 30%). LC/MS (Method I): $t_R$=2.17 min, >95%, m/z (ESI$^+$)=259 (MH$^+$).

Example 16-4

Preparation of 2-(4,5-Dimethyl-thiazol-2-yl)-5-trifluoromethyl-phenylamine (69)

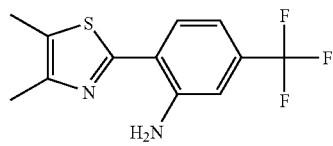

69

Procedure A, described in Example 11-1, was followed, except that 4,5-dimethyl-2-(2-nitro-4-trifluoromethyl-phenyl)-thiazole, (51) was used instead of 1-(2-nitro-4-trifluoromethyl-phenyl)-1H-pyrazole. Purification by flash-chromatography (Silica; ethyl acetate/Heptane) afforded the title compound (252 mg, 40%). LC/MS (Method I): $t_R$=2.39 min, >95%, m/z (ESI$^+$)=273 (MH$^+$).

Example 16-5

Preparation of 2-(4-Isopropyl-thiazol-2-yl)-5-trifluoromethyl-phenylamine (70)

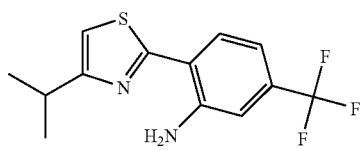

70

Procedure A, described in Example 11-1, was followed, except that 4-isopropyl-2-(2-nitro-4-trifluoromethyl-phenyl)-thiazole (57) was used instead of 1-(2-nitro-4-trifluoromethyl-phenyl)-1H-pyrazole. Purification by flash-chromatography (Silica; ethyl acetate/Heptane) afforded the title compound (61 mg, 38%). LC/MS (Method I): $t_R$=2.72 min, >95%, m/z (ESI$^+$)=287 (MH$^+$).

Example 16-6

Preparation of 2-(4-tert-Butyl-thiazol-2-yl)-5-trifluoromethyl-phenylamine (71)

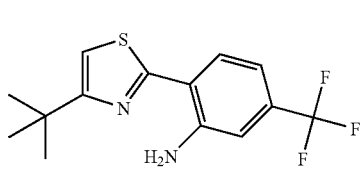

71

Procedure A, described in Example 11-1, was followed, except that 4-tert-butyl-2-(2 nitro-4-trifluoromethyl-phenyl)-thiazole (58) was used instead of 1-(2-nitro-4-trifluoromethyl-phenyl)-1H-pyrazole. Purification by flash-chromatography (Silica; ethyl acetate/Heptane) afforded the title compound (60 mg, 55%). LC/MS (Method I): $t_R$=2.68 min, >95%, m/z (ESI$^+$)=301 (MH$^+$).

Example 16-7

Preparation of 2-(4-Ethyl-thiazol-2-yl)-5-trifluoromethyl-phenylamine (72)

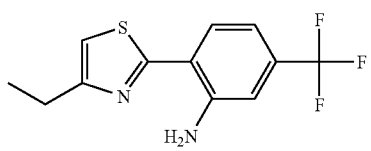

72

Procedure A, described in Example 11-1, was followed, except that 4-ethyl-2-(2-nitro-4-trifluoromethyl-phenyl)-thiazole (59) was used instead of 1-(2-nitro-4-trifluoro-methyl-phenyl)-1H-pyrazole. Purification by flash-chromatography (Silica; ethyl acetate/Heptane) afforded the title compound (40 mg, 39%). LC/MS (Method J): $t_R$=2.29 min, >85%, m/z (ESI$^+$)=273 (MH$^+$).

Example 16-8

Preparation of 2-(5-Ethyl-thiazol-2-yl)-5-trifluoromethyl-phenylamine (73)

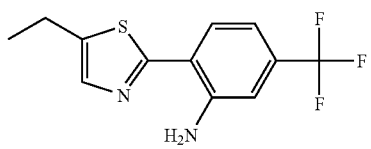

73

Procedure A, described in Example 11-1, was followed except that 5-ethyl-2-(2-nitro-4-trifluoromethyl-phenyl)-thiazole (60) was used instead of 1-(2-nitro-4-trifluoro-methyl-phenyl)-1H-pyrazole. Purification by flash-chromatography (Silica; ethyl acetate/Heptane) afforded the title compound (67 mg, 32%). LC/MS (Method I): $t_R$=2.37 min, >95%, m/z (ESI$^+$)=273 (MH$^+$).

Example 16-9

Preparation of 2-(4-Ethyl-thiazol-2-yl)-5-methyl-phenylamine (74)

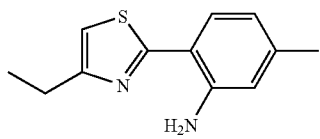

74

Procedure B, described in Example 16-2, was followed, except that 4-ethyl-2-(2-nitro-4-methyl-phenyl)-thiazole (62) was used instead of 5-isopropyl-2-(2-nitro-4-trifluoromethyl-phenyl)-thiazole which gave the title compound (62 mg, 79%). LC/MS (Method I): $t_R$=1.16 min, >90%, m/z (ESI$^+$)=219 (MH$^+$).

Example 16-10

Preparation of 2-(5-Ethyl-thiazol-2-yl)-5-methyl-phenylamine (75)

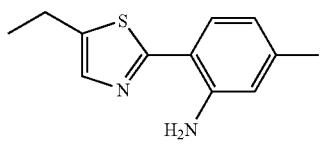

75

Procedure B, described in Example 16-2, was followed, except that 5-ethyl-2-(2-nitro-4-methyl-phenyl)-thiazole (63) was used instead of 5-isopropyl-2-(2-nitro-4-trifluoromethyl-phenyl)-thiazole, which gave the title compound (35 mg, 65%). LC/MS (Method I): $t_R$=1.09 min, >90%, m/z (ESI$^+$)=219 (MH$^+$).

Example 16-11

Preparation of 2-Thiazol-2-yl-5-trifluoromethyl-phenylamine (76)

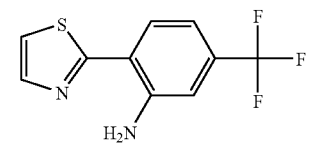

76

Procedure B, described in Example 16-2, was followed, except that 2-(2-nitro-4-trifluoromethyl-phenyl)-thiazole (64) was used instead of 5-isopropyl-2-(2-nitro-4-trifluoromethyl-phenyl)-thiazole, which gave the title compound (60 mg, 93%). LC/MS (Method I): $t_R$=1.71 min, >90%, m/z (ESI$^+$)=245 (MH$^+$).

Example 16-12

Preparation of 5-Methyl-2-thiazol-2-yl-phenylamine (77)

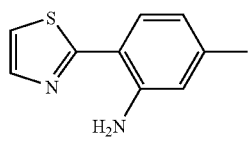

77

Procedure B, described in Example 16-2, was followed except that 2-(2-nitro-4-methyl-phenyl)-thiazole (65) was used instead of 5-isopropyl-2-(2-nitro-4-trifluoromethyl-phenyl)-thiazole, which gave the title compound, (52 mg, 91%). LC/MS (Method F): $t_R$=1.99 min, >90%, m/z (ESI$^+$)= 191 (MH$^+$).

Example 17-1

Procedure D for carbamate formation, exemplified with the synthesis of [2-(5-Ethyl-thiazol-2-yl)-5-trifluoromethyl-phenyl]-carbamic acid 3-(1-cyclopropanesulfonylaminocarbonyl-2-vinyl-cyclopropyl-carbamoyl)-4-(hex-5-enyl-methyl-carbamoyl)-cyclopentyl ester (78).

78

Compound 8 (described in Example 5) (50 mg, 103 μmol) was dissolved in dried DCM (2 ml) followed by addition of solid NaHCO$_3$ (17 mg, 209 μmol) and a stirrbar. To this slurry was then added phosgene in toluene (1.93 M, 800 μl, 1.52 mmol) and the mixture stirred vigorously for 3 h to afford the chloroformate (9). LC/MS (Method G): $t_R$=2.65 min, >95%, m/z (ESI⁺)=544 (MH⁺). The solvent was removed in vacuo and the residue was co-evaporated with DCM to remove any residual phosgene. The afforded chloroformate was subsequently re-dissolved in dried DCE (3 ml) and 2-(5-ethyl-thiazol-2-yl)-5-trifluoromethyl-phenylamine (73) (34 mg, 124 μmol) was added followed by the addition of K₂CO₃(s) (28.5 mg, 206 μmol) and powdered 4 Å molecular sieves (1 spatula). The mixture was heated to 120° C. for 30 min, after which time LC/MS analysis showed no remaining chloroformate. The reaction was filtered and the filtrate applied directly onto a Si-SPE cartridge and the cartridge washed with DCM. The SPE cartridge was then eluted with 5% methanol in DCM to elute the title compound (76 mg, 80%). LC/MS (Method J): $t_R$=2.72 min, 95%, m/z (ESI⁺)=780 (MH⁺).

Example 17-2

Preparation of [2-(4-Methyl-thiazol-2-yl)-5-trifluoromethyl-phenyl]-carbamic acid 3-(1-cyclopropanesulfonylaminocarbonyl-2-vinyl-cyclopropyl-carbamoyl)-4-(hex-5-enyl-methyl-carbamoyl)-cyclopentyl ester (79)

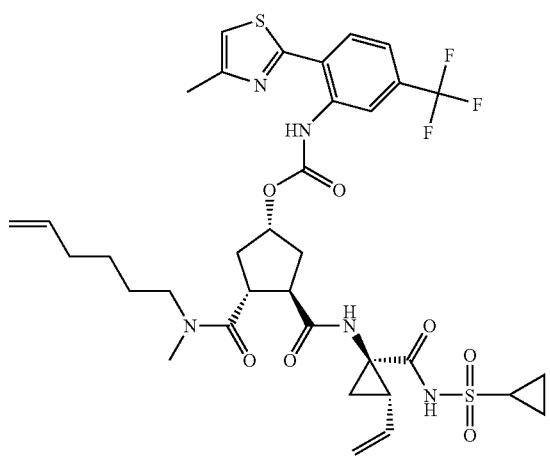

79

The title compound was prepared according to procedure B, described in Example 7-1, except that 2-(4-methyl-thiazol-2-yl)-5-trifluoromethyl-phenylamine (66) was used instead of 2-isocyanatobiphenyl. LC/MS (Method I): $t_R$=2.54 min, >90%, m/z (ESI⁺)=766 (MH⁺).

Example 17-3

Preparation of [2-(5-Methyl-thiazol-2-yl)-5-trifluoromethyl-phenyl]-carbamic acid 3-(1-cyclopropanesulfonylaminocarbonyl-2-vinyl-cyclopropyl-carbamoyl)-4-(hex-5-enyl-methyl-carbamoyl)-cyclopentyl ester (80)

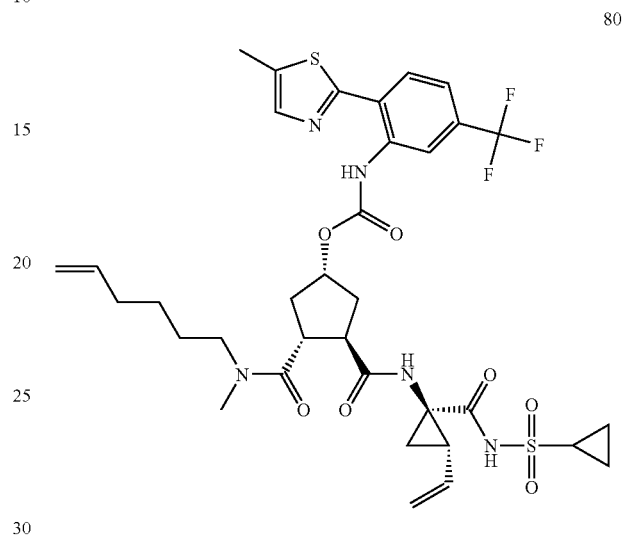

80

The title compound was prepared according to procedure B, described in Example 7-1, except that 2-(5-methyl-thiazol-2-yl)-5-trifluoromethyl-phenylamine (68) was used instead of 2-isocyanatobiphenyl. LC/MS (Method I): $t_R$=2.94 min, >90%, m/z (ESI⁺)=766 (MH⁺).

Example 17-4

Preparation of [2-(4,5-Dimethyl-thiazol-2-yl)-5-trifluoromethyl-phenyl]-carbamic acid 3-(1-cyclopropanesulfonylaminocarbonyl-2-vinyl-cyclopropylcarbamoyl)-4-(hex-5-enyl-methyl-carbamoyl)-cyclopentyl ester (81)

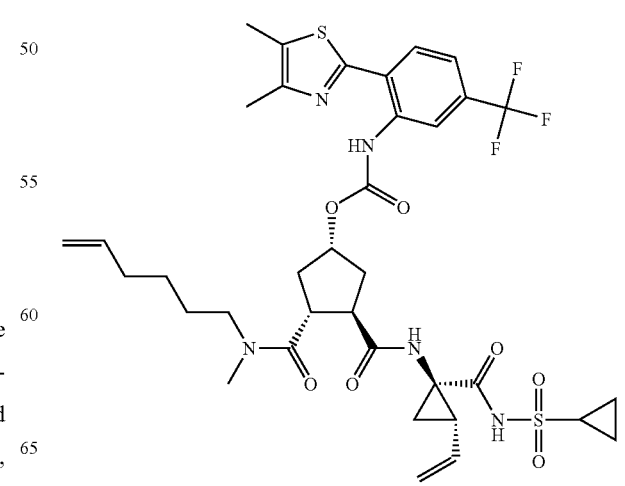

81

The title compound was prepared according to procedure B, described in Example 7-1, except that 2-(4,5-dimethyl-thiazol-2-yl)-5-trifluoromethyl-phenylamine (69) was used instead of 2-isocyanatobiphenyl. LC/MS (Method I): $t_R$=3.12 min, >90%, m/z (ESI$^+$)=781 (MH$^+$).

Example 17-5

Preparation of [2-(4-Isopropyl-thiazol-2-yl)-5-trifluoromethyl-phenyl]-carbamic acid 3-(1-cyclopropanesulfonylaminocarbonyl-2-vinyl-cyclopropylcarbamoyl)-4-(hex-5-enyl-methyl-carbamoyl)-cyclopentyl ester (82)

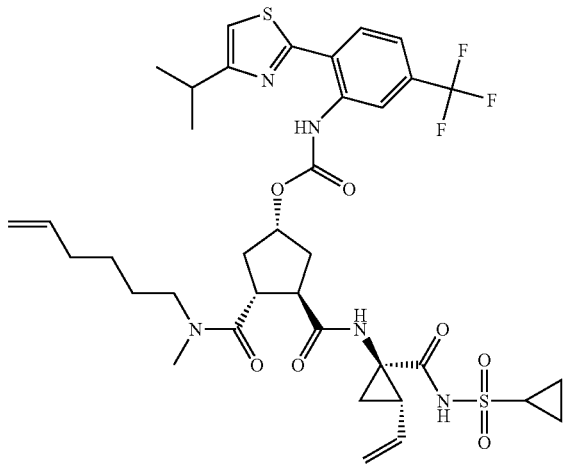

82

The title compound was prepared according to procedure B, described in Example 7-1, except that 2-(4-isopropyl-thiazol-2-yl)-5-trifluoromethyl-phenylamine (70) was used instead of 2-isocyanatobiphenyl. LC/MS (Method J): $t_R$=2.97 min, >90%, m/z (ESI$^+$)=794 (MH$^+$).

Example 17-6

Preparation of [2-(4-tert-Butyl-thiazol-2-yl)-5-trifluoromethyl-phenyl]-carbamic acid 3-(1-cyclopropanesulfonylaminocarbonyl-2-vinyl-cyclopropylcarbamoyl)-4-(hex-5-enyl-methyl-carbamoyl)-cyclopentyl ester (83)

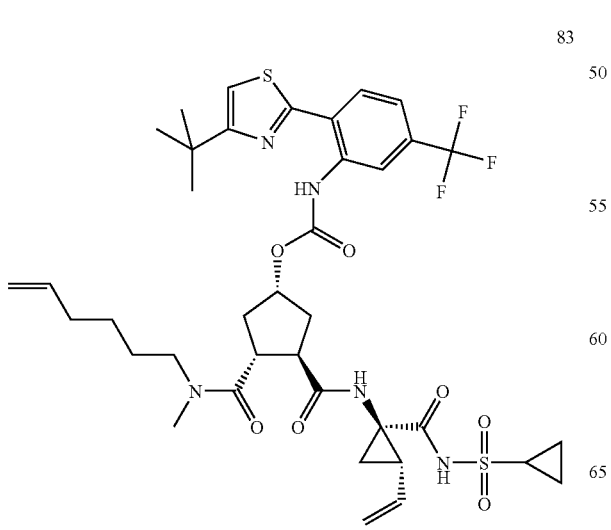

83

The title compound was prepared according to procedure B, described in Example 7-1, except that 2-(4-tert-butyl-thiazol-2-yl)-5-trifluoromethyl-phenylamine (71) was used instead of 2-isocyanatobiphenyl. LC/MS (Method J): $t_R$=3.07 min, >90%, m/z (ESI$^+$)=808 (MH$^+$).

Example 17-7

Preparation of [2-(4-Ethyl-thiazol-2-yl)-5-trifluoromethyl-phenyl]-carbamic acid 3-(1-cyclopropanesulfonylaminocarbonyl-2-vinyl-cyclopropyl-carbamoyl)-4-(hex-5-enyl-methyl-carbamoyl)-cyclopentyl ester (84)

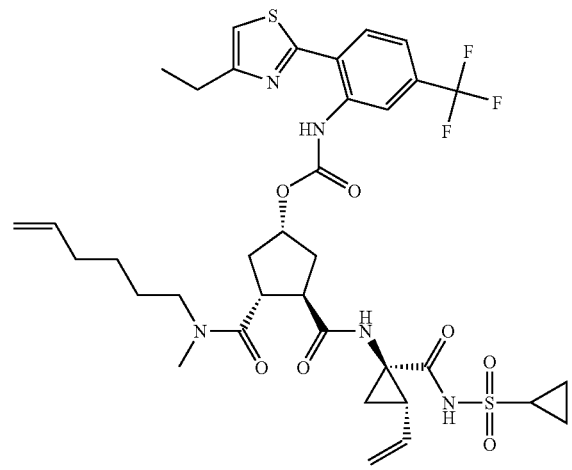

84

The title compound was prepared according to procedure B, described in Example 7-1, except that 2-(4-Ethyl-thiazol-2-yl)-5-trifluoromethyl-phenylamine (72) was used instead of 2-isocyanatobiphenyl. LC/MS (Method J): $t_R$=2.81 min, >90%, m/z (ESI$^+$)=780 (MH$^+$).

Example 17-8

Preparation of [2-(5-Isopropyl-thiazol-2-yl)-5-trifluoromethyl-phenyl]-carbamic acid 3-(1-cyclopropanesulfonylaminocarbonyl-2-vinyl-cyclopropylcarbamoyl)-4-(hex-5-enyl-methyl-carbamoyl)-cyclopentyl ester (85)

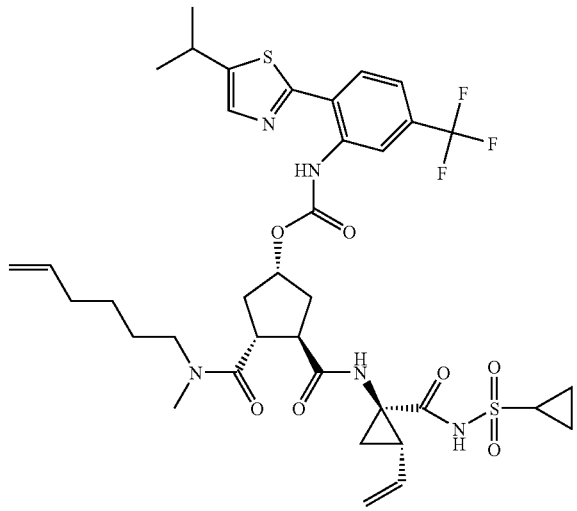

85

The title compound was prepared according to procedure D, described in Example 17-1, except that 2-(5-isopropyl-thiazol-2-yl)-5-trifluoromethyl-phenylamine (67) was used instead of 2-(5-ethyl-thiazol-2-yl)-5-trifluoromethyl-phenylamine. LC/MS (Method J): $t_R$=2.85 min, >90%, m/z (ESI$^+$)= 794 (MH$^+$).

Example 17-9

Preparation of [2-(4-Ethyl-thiazol-2-yl)-5-methyl-phenyl]-carbamic acid 3-(1-cyclopropanesulfony-laminocarbonyl-2-vinyl-cyclopropylcarbamoyl)-4-(hex-5-enyl-methyl-carbamoyl)-cyclopentyl ester (86)

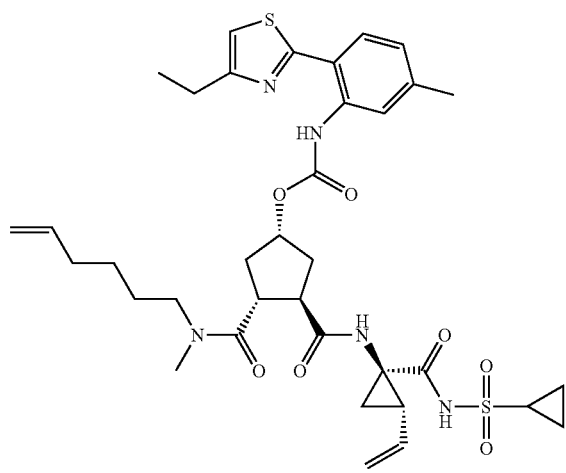

The title compound was prepared according to procedure D, described in Example 17-1, except that 2-(4-ethyl-thiazol-2-yl)-5-methyl-phenylamine (74) was used instead of 2-(5-ethyl-thiazol-2-yl)-5-trifluoromethyl-phenylamine. LC/MS (Method J): $t_R$=2.63 min, >90%, m/z (ESI$^+$)=726 (MH$^+$).

Example 17-10

Preparation of [2-(5-Ethyl-thiazol-2-yl)-5-methyl-phenyl]-carbamic acid 3-(1-cyclopropanesulfony-laminocarbonyl-2-vinyl-cyclopropylcarbamoyl)-4-(hex-5-enyl-methyl-carbamoyl)-cyclopentyl ester (87)

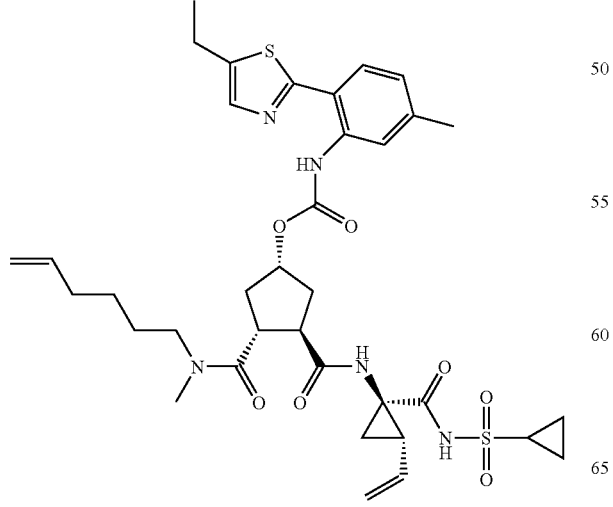

The title compound was prepared according to procedure D, described in Example 17-1, except that 2-(5-ethyl-thiazol-2-yl)-5-methyl-phenylamine (75) was used instead of 2-(5-ethyl-thiazol-2-yl)-5-trifluoromethyl-phenylamine. LC/MS (Method J): $t_R$=2.61 min, >90%, m/z (ESI$^+$)=726 (MH$^+$).

Example 17-11

Preparation of [2-(thiazol-2-yl)-5-trifluoromethyl-phenyl]-carbamic acid 3-(1-cyclopropane-sulfony-laminocarbonyl-2-vinyl-cyclopropylcarbamoyl)-4-(hex-5-enyl-methyl-carbamoyl)-cyclo-pentyl ester (88)

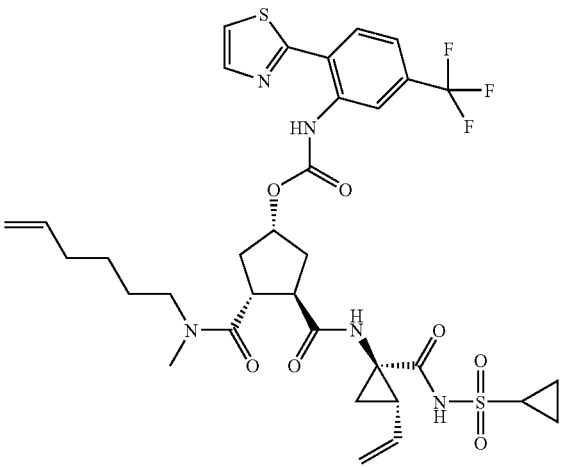

The title compound was prepared according to procedure D, described in Example 17-1, except that 2-thiazol-2-yl-5-trifluoromethyl-phenylamine (76) was used instead of 2-(5-ethyl-thiazol-2-yl)-5-trifluoromethyl-phenylamine (73). LC/MS (Method I): $t_R$=2.54 min, 90%, m/z (ESI$^+$)=752 (MH$^+$).

Example 17-12

Preparation of [2-(thiazol-2-yl)-5-methyl-phenyl]-carbamic acid 3-(1-cyclopropanesulfonylamino-carbonyl-2-vinyl-cyclopropylcarbamoyl)-4-(hex-5-enyl-methyl-carbamoyl)-cyclo-pentyl ester (89).

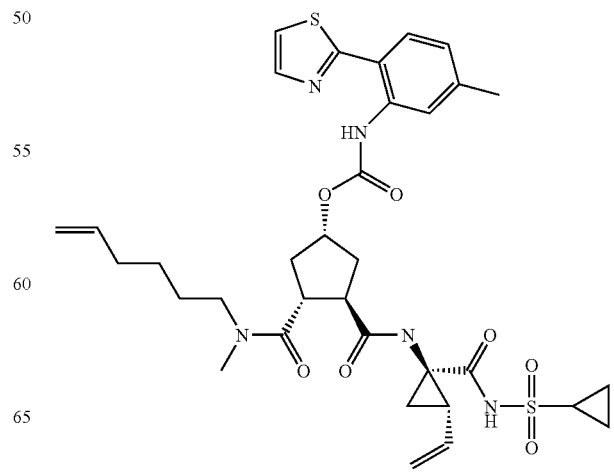

The title compound was prepared according to the procedure D, described in Example 17-1, except that 5-methyl-2-thiazol-2-yl-phenylamine (77) was used instead of 2-(5-ethyl-thiazol-2-yl)-5-trifluoromethyl-phenylamine. LC/MS (Method I): $t_R$=2.39 min, 90%, m/z (ESI$^+$)=698 (MH$^+$).

Example 17-13

Preparation of (2-Pyridin-2-yl-5-trifluoromethyl-phenyl)-carbamic acid 3-(1-cyclopropane-sulfonylaminocarbonyl-2-vinyl-cyclopropylcarbamoyl)-4-(hex-5-enyl-methyl-carbamoyl)-cyclopentyl ester (90)

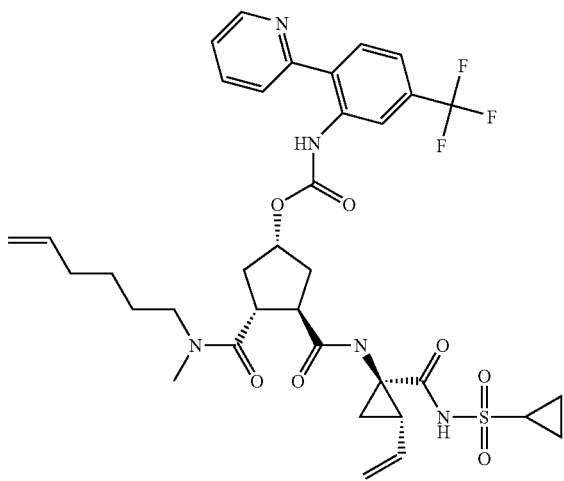

The title compound was prepared according to procedure D, described in Example 17-1, except that 2-pyridin-2-yl-5-trifluoromethyl-phenylamine (108) was used instead of 2-(5-ethyl-thiazol-2-yl)-5-trifluoromethyl-phenylamine. LC/MS (Method I): $t_R$=2.01 min, >90%, m/z (ESI$^+$)=746 (MH$^+$).

Example 17-14

Preparation of [2-(2-methyl-thiazol-4-yl)-5-trifluoromethyl-phenyl]-carbamic acid 3-(1-cyclopropane-sulfonylaminocarbonyl-2-vinyl-cyclopropyl-carbamoyl)-4-(hex-5-enyl-methyl-carbamoyl)-cyclopentyl ester (91)

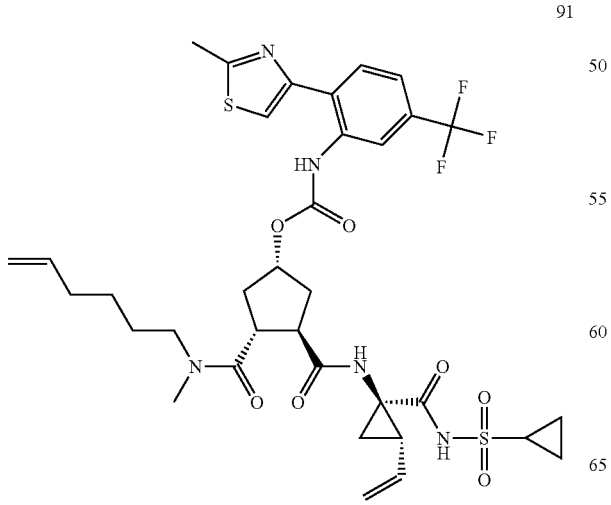

The title compound was prepared according to procedure D, described in Example 17-1, except that 2-(2-methyl-thiazol-4-yl)-5-trifluoromethyl-phenylamine, (109) was used instead of 2-(5-ethyl-thiazol-2-yl)-5-trifluoromethyl-phenylamine. LC/MS (Method I): $t_R$=2.57 min, >90%, m/z (ESI$^+$)=766 (MH$^+$).

Example 17-15

Preparation of [2-(6-methyl-pyridin-2-yl)-5-trifluoromethyl-phenyl]-carbamic acid 3-(1-cyclopropane-sulfonylaminocarbonyl-2-vinyl-cyclopropylcarbamoyl)-4-(hex-5-enyl-methyl-carbamoyl)-cyclopentyl ester (92)

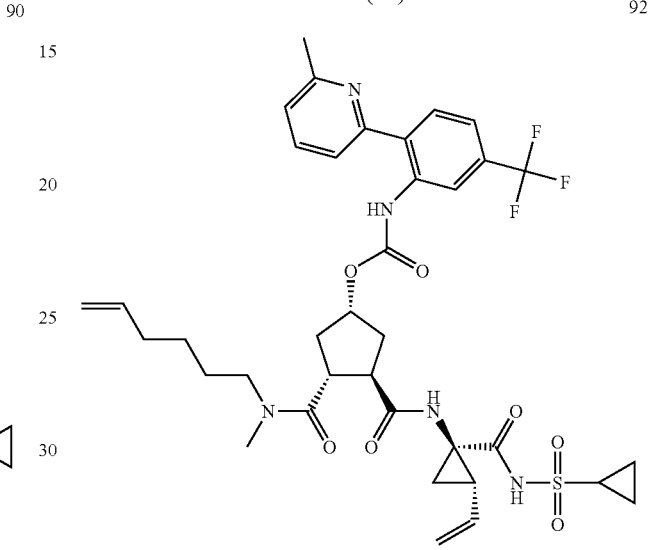

The title compound was prepared according to procedure D, described in Example 17-1, except that 2-(6-methyl-pyridin-2-yl)-5-trifluoromethyl-phenylamine, (110) was used instead of 2-(5-ethyl-thiazol-2-yl)-5-trifluoromethyl-phenylamine. LC/MS (Method I): $t_R$=1.82 min, >90%, m/z (ESI$^+$)=760 (MH$^+$).

Example 18-1

Preparation of [2-(4-methyl-thiazol-2-yl)-5-trifluoromethyl-phenyl]-carbamic acid 4-cyclopropane-sulfonyl-aminocarbonyl-13-methyl-2,14-dioxo-3,13-diaza-tricyclo-[13.3.0.0$^{4,6}$]-octadec-7-en-17-yl ester (93).

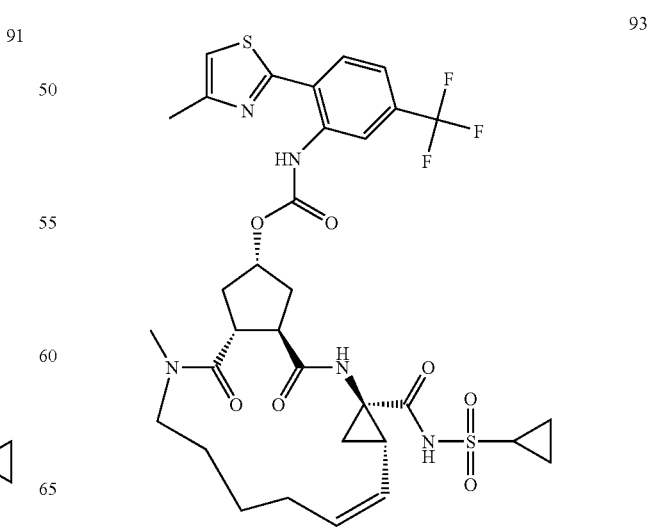

The title compound was prepared according to the procedure described in Example 9-1, except that compound 79 was used instead of compound 10. LC/MS (Method I): $t_R$=2.30 min, >95%, m/z (ESI$^+$)=738 (MH$^+$).

Example 18-2

Preparation of [2-(5-methyl-thiazol-2-yl)-5-trifluoromethyl-phenyl]-carbamic acid 4-cyclopropanesulfonylaminocarbonyl-13-methyl-2,14-dioxo-3,13-diaza-tricyclo[13.3.0.0$^{4,6}$]-octadec-7-en-17-yl ester (94)

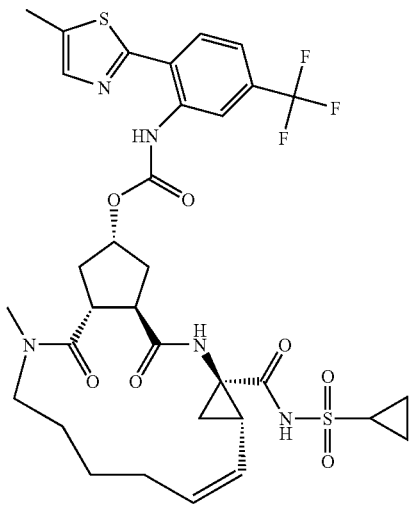

94

The title compound was prepared according to the procedure described in Example 9-1, except that compound 80 was used instead of compound 10. LC/MS (Method I): $t_R$=2.81 min, >95%, m/z (ESI$^+$)=752 (MH$^+$).

Example 18-3

Preparation of [2-(4,5-dimethyl-thiazol-2-yl)-5-trifluoromethyl-phenyl]-carbamic acid 4-cyclo-propane-sulfonylaminocarbonyl-13-methyl-2,14-dioxo-3,13-diaza-tricyclo-[13.3.0.0$^{4,6}$]octadec-7-en-17-yl ester (95)

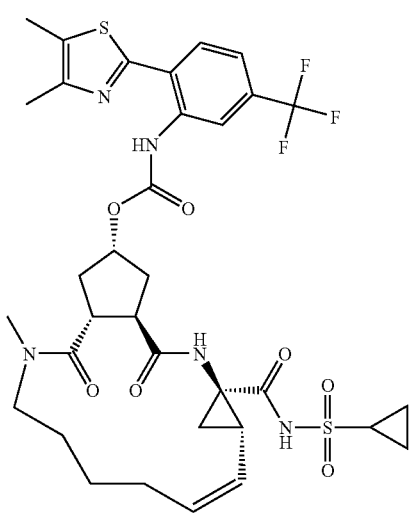

95

The title compound was prepared according to the procedure described in Example 9-1, except that compound 81 was used instead of compound 10. LC/MS (Method I): $t_R$=2.81 min, >95%, m/z (ESI$^+$)=752 (MH$^+$).

Example 18-4

Preparation of [2-(4-Isopropyl-thiazol-2-yl)-5-trifluoromethyl-phenyl]-carbamic acid 4-cyclo-propane-sulfonylaminocarbonyl-13-methyl-2,14-dioxo-3,13-diaza-tricyclo-[13.3.0.0$^{4,6}$]octadec-7-en-17-yl ester (96).

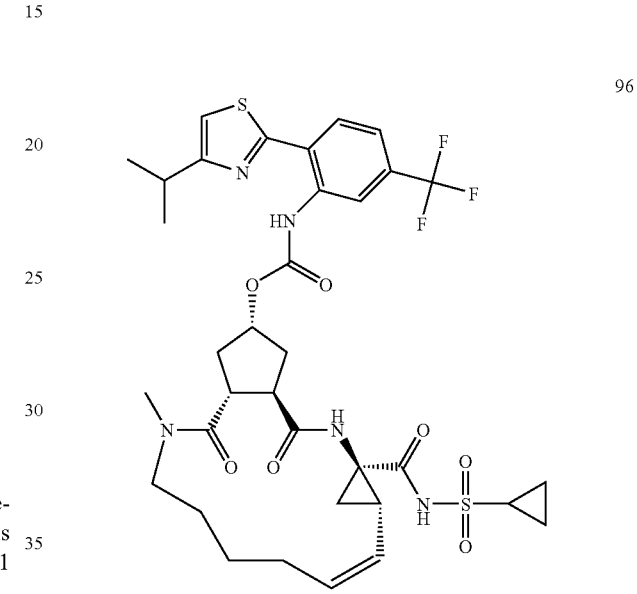

96

The title compound was prepared according to the procedure described in Example 9-1, except that compound 82 was used instead of compound 10. LC/MS (Method J): $t_R$=2.70 min, >95%, m/z (ESI$^+$)=752 (MH$^+$).

Example 18-5

Preparation of [2-(4-tert-Butyl-thiazol-2-yl)-5-trifluoromethyl-phenyl]-carbamic acid 4-cyclopropanesulfonylaminocarbonyl-13-methyl-2,14-dioxo-3,13-diaza-tricyclo[13.3.0.0^{4,6}]octadec-7-en-17-yl ester (97)

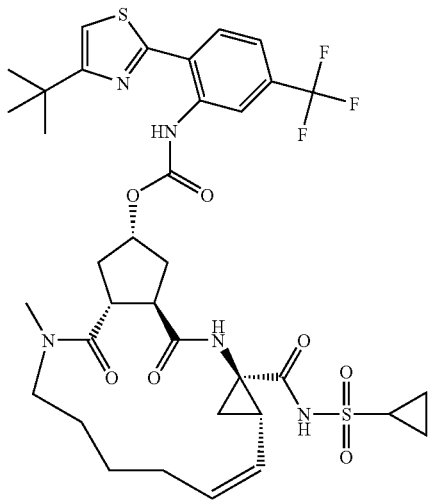

97

The title compound was prepared according to the procedure described in Example 9-1, except that compound 83 was used instead of compound 10. LC/MS (Method J): $t_R$=2.83 min, >95%, m/z (ESI$^+$)=780 (MH$^+$).

Example 18-6

Preparation of [2-(4-Ethyl-thiazol-2-yl)-5-trifluoromethyl-phenyl]-carbamic acid 4-cyclopropane-sulfonylaminocarbonyl-13-methyl-2,14-dioxo-3,13-diaza-tricyclo[13.3.0.0^{4,6}]octadec-7-en-17-yl ester (98)

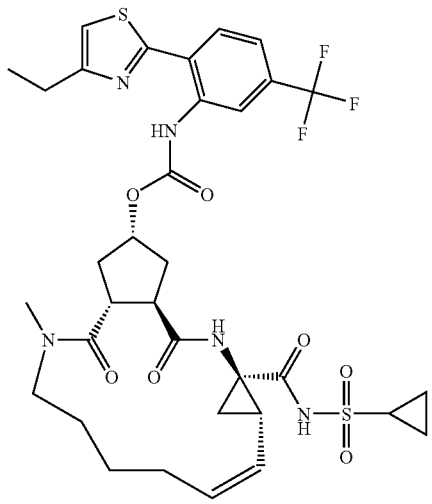

98

The title compound was prepared according to the procedure described in Example 9-1, except that compound 84 was used instead of compound 10. LC/MS (Method J): $t_R$=2.54 min, >95%, m/z (ESI$^+$)=752 (MH$^+$).

Example 18-7

Preparation of [2-(5-Ethyl-thiazol-2-yl)-5-trifluoromethyl-phenyl]-carbamic acid 4-cyclopropane-sulfonylaminocarbonyl-13-methyl-2,14-dioxo-3,13-diaza-tricyclo[13.3.0.0^{4,6}]octadec-7-en-17-yl ester (99)

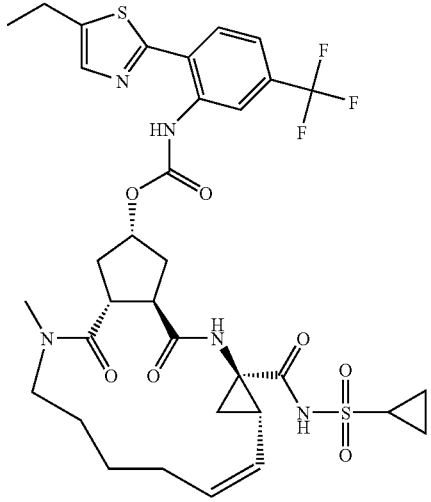

99

The title compound was prepared according to the procedure described in Example 9-1, except that compound 78 was used instead of compound 10. LC/MS (Method J): $t_R$=2.45 min, >95%, m/z (ESI$^+$)=752 (MH$^+$).

Example 18-8

Preparation of [2-(5-isopropyl-thiazol-2-yl)-5-trifluoromethyl-phenyl]-carbamic acid 4-cyclopropane-sulfonylaminocarbonyl-13-methyl-2,14-dioxo-3,13-diaza-tricyclo[13.3.0.0^{4,6}]octadec-7-en-17-yl ester (100).

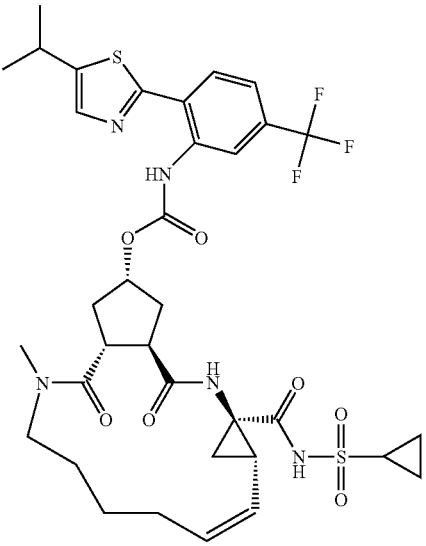

100

The title compound was prepared according to the procedure described in Example 9-1, except that compound 85 was used instead of compound 10. LC/MS (Method J): $t_R$=2.62 min, >95%, m/z (ESI$^+$)=766 (MH$^+$).

Example 18-9

Preparation of [2-(4-ethyl-thiazol-2-yl)-5-methyl-phenyl]-carbamic acid 4-cyclopropane sulfonylaminocarbonyl-13-methyl-2,14-dioxo-3,13-diaza-tricyclo-[13.3.0.0$^{4,6}$]octadec-7-en-17-yl ester (101)

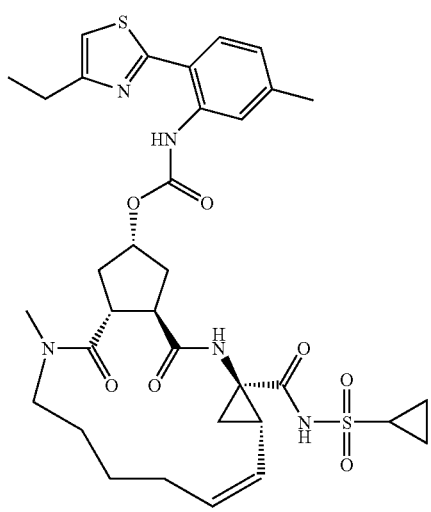

The title compound was prepared according to the procedure described in Example 9-1, except that compound 86 was used instead of compound 10. LC/MS (Method J): $t_R$=2.29 min, >95%, m/z (ESI$^+$)=698 (MH$^+$).

Example 18-10

Preparation of [2-(5-Ethyl-thiazol-2-yl)-5-methyl-phenyl]-carbamic acid 4-cyclopropane-sulfonylaminocarbonyl-13-methyl-2,14-dioxo-3,13-diaza-tricyclo[13.3.0.0$^{4,6}$]-octadec-7-en-17-yl ester (102)

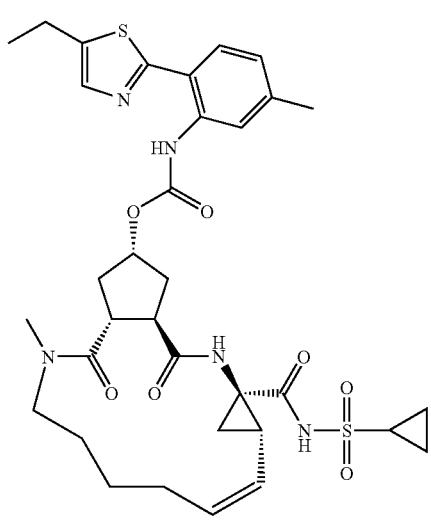

The title compound was prepared according to the procedure described in Example 9-1, except that compound 87 was used instead of compound 10. LC/MS (Method J): $t_R$=2.31 min, >95%, m/z (ESI$^+$)=698 (MH$^+$).

Example 18-11

Preparation of (2-Pyridin-2-yl-5-trifluoromethyl-phenyl)-carbamic acid 4-cyclopropanesulfonyl-aminocarbonyl-13-methyl-2,14-dioxo-3,13-diaza-tricyclo[13.3.0.0$^{4,6}$]octadec-7-en-17-yl ester (103)

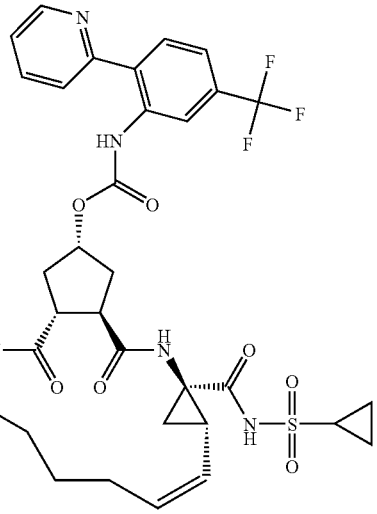

The title compound was prepared according to the procedure described in Example 9-1, except that compound 90 was used instead of compound 10. LC/MS (Method I): $t_R$=1.45 min, 93%, m/z (ESI$^+$)=718 (MH$^+$).

Example 18-12

Preparation of [2-(2-Methyl-thiazol-4-yl)-5-trifluoromethyl-phenyl]-carbamic acid 4-cyclopropane-sulfonylaminocarbonyl-13-methyl-2,14-dioxo-3,13-diaza-tricyclo[13.3.0.0$^{4,6}$]-octadec-7-en-17-yl ester (104)

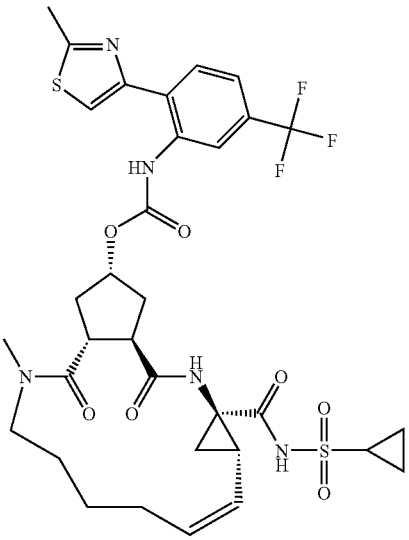

The title compound was prepared according to the procedure described in Example 9-1, except that compound 91 was used instead of compound 10. LC/MS (Method I): $t_R$=2.21 min, >95%, m/z (ESI$^+$)=738 (MH$^+$).

Example 18-13

Preparation of [2-(6-Methyl-pyridin-2-yl)-5-trifluoromethyl-phenyl]-carbamic acid 4-cyclopropanesulfonylaminocarbonyl-13-methyl-2,14-dioxo-3,13-diaza-tricyclo-[13.3.0.0$^{4,6}$]octadec-7-en-17-yl ester (105)

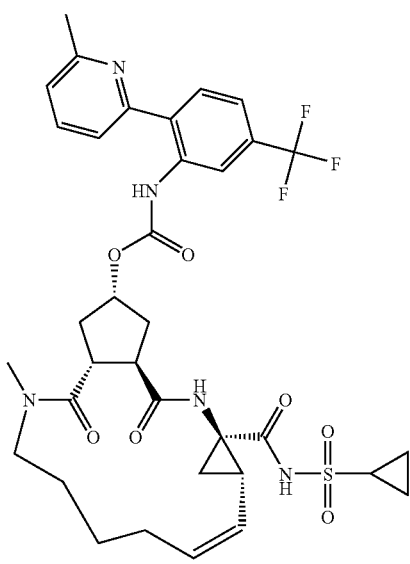

105

The title compound was prepared according to the procedure described in Example 9-1, except that compound 92 was used instead of compound 10. LC/MS (Method I): $t_R$=1.23 min, 95%, m/z (ESI$^+$)=732 (MH$^+$).

Example 19-1

General procedure for the preparation of tin derivatives for use in Stille-couplings, exemplified for the synthesis of 2-methyl-4-tributyltin-thiazole (106)

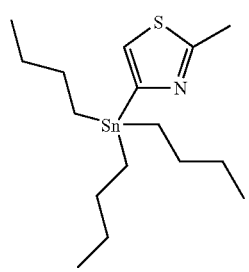

106

To a stirred solution of n-butyllithium (1.3 eq, 2.7 ml of 2.5M solution in hexanes) in dry diethyl ether (50 ml), cooled at −78° C., was added dropwise over 20 min a solution of 4-bromo-2-methylthiazole (950 mg, 5.3 mmol, 1 eq) in diethyl ether (5 ml). The mixture was stirred for 1 h at −78° C. and then a solution of trimethyltin chloride (2.2 g, 6.8 mmol, 1.3 eq) in diethyl ether was added dropwise over 15 min. After additional stirring for 1 h at −78° C., the reaction mixture was washed with saturated aqueous sodium hydrogen carbonate (30 ml) and the product extracted with diethyl ether (2×50 ml). The organic layer was dried with magnesium sulphate and concentrated by rotary evaporation. The resulting oil was purified by Kugelrohr distillation to afford the title compound (2.3 g) as colourless oil which was used as is in further coupling reaction.

Example 19-2

Preparation of 6-Methyl-2-tributyltin-pyridine (107)

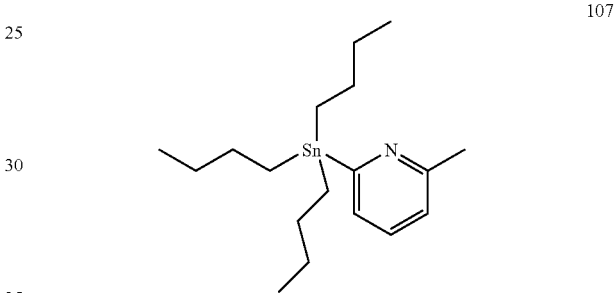

107

The procedure described in Example 19-1 was followed, but using 2-bromo-6-methyl-pyridine (1 g) instead of 4-bromo-2-methylthiazole. Purification was done by removing of excess of tributyltin chloride by kugelrohr distillation (200° C., 5×10$^{-3}$ mbar) and the residual oil was purified by fast column chromatography on silica (ethyl acetate/petroleum ether 95:5, decompose on the column) to give 1.1 g of the title compound as colourless oil (yield 50%).

Example 20-1

General procedure for Stille coupling, exemplified by synthesis of compound 2-Pyridin-2-yl-5-trifluoromethyl-phenylamine (108)

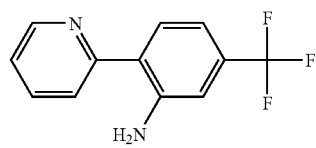

108

A screw cap tube was charged with 2-tributyltinpyridine (1.4 eq), prepared from 2-bromopyridine and tributyltin hydride according to the procedure described in example 19-1, o-bromoaniline (200 mg, 1 eq), Pd(dba)$_2$ (10-14 mg, 2 mol %), CuI (20 mg, 10 mol %), and PPh$_3$ (40 mg, 15 mol %). The mixture was degassed and back-filled with argon. Dry diethyl ether (5 ml) was added, and the reaction mixture was heated at 120° C. for 4 h in a microwave oven. The reaction mixture was cooled to room temperature, stirred with saturated aqueous KF (3 ml) for 3 h, and filtered. The solid was discarded after washing with ethyl acetate (three times). The liquid was poured into H$_2$O and extracted with ethyl acetate. The combined organic layer was washed with H$_2$O and brine, dried over MgSO$_4$, and filtered and the solvent was removed in vacuo. The residue was purified by column chromatography on silica (ethyl acetate/petroleum ether as eluent) to afford the title compound as a white solid (60 mg, 38%). M$^+$ 239.

Example 20-2

Preparation of 2-(2-Methyl-thiazol-4-yl)-5-trifluoromethyl-phenylamine (109)

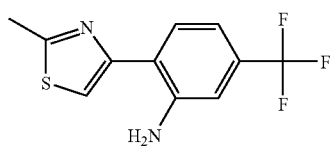

109

The general procedure described in Example 20-1 was followed, except that 2-methyl-4-tributyltin-thiazole (106) was used instead of 2-tributyltinpyridine and THF was used as solvent instead of diethyl ether, which gave the title compound as an off white solid (140 mg, 63%), M$^+$ 259.

Example 20-3

Preparation of 2-(6-Methyl-pyridin-2-yl)-5-trifluoromethyl-phenylamine (110)

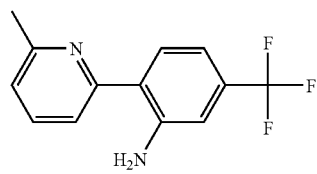

110

The general procedure described in Example 20-1 was followed, except that 6-methyl-2-tributyltinpyridine (107) was used instead of 2-tributyltinpyridine and THF was used as solvent instead of diethyl ether and the heating was performed in a thermo block for 23 h at 85° C., which gave the title compound as a yellowish solid (97 mg, 50%), M$^+$ 259.

Example 21

Preparation of 4-Hydroxycyclopentane-1,2-dicarboxylic acid 1-(hex-5-enyl-methylamide) 2-{[1-(1-methylcyclopropanesulphonylaminocarbonyl)-2-vinyl-cyclopropyl]-amide} (111)

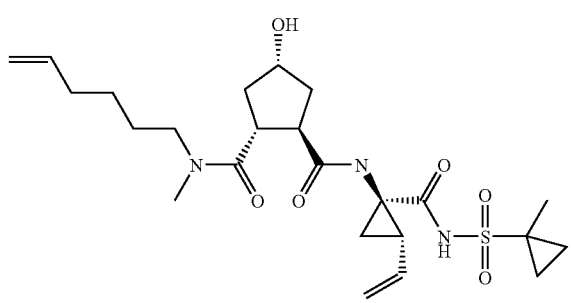

111

The procedure described in Example 5 was followed but using methylcyclopropane-sulphonic acid amide (405 mg, 3 mmol) instead of cyclopropanesulphonic acid amide, which gave the title compound (246 mg, 50%). LC/MS (Method F): t$_r$=2.26 min, >90%, m/z (ESI$^+$)=496 (MH$^+$).

Example 22

Preparation of [2-(5-Ethyl-thiazol-2-yl)-5-methyl-phenyl]-carbamic acid 3-(hex-5-enyl-methyl-carbamoyl)-4-[1-(1-methyl-cyclopropanesulfonylamino-carbonyl)-2-vinyl-cyclopropylcarbamoyl]-cyclopentyl ester (112)

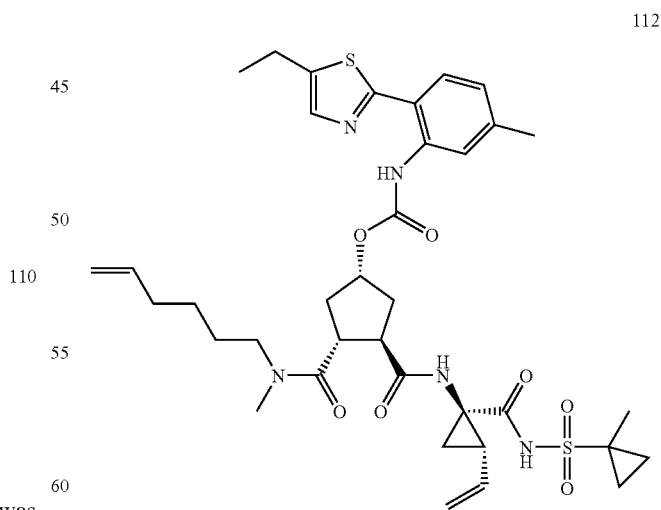

112

The procedure described in Example 17-10 was followed but using the compound prepared in Example 21 (111) (49 mg, 0.1 mmol) instead of the corresponding cyclopropanesulphonic acid amide derivative, which gave the title com-

Example 23

Preparation of [2-(4-Ethyl-thiazol-2-yl)-5-methyl-phenyl]-carbamic acid 13-methyl-4-(1-methyl-cyclopropanesulphonylaminocarbonyl)-2,14-dioxo-3,13-diaza-tricyclo[13.3.0.0$^{4,6}$]octadec-7-en-17-yl ester (113)

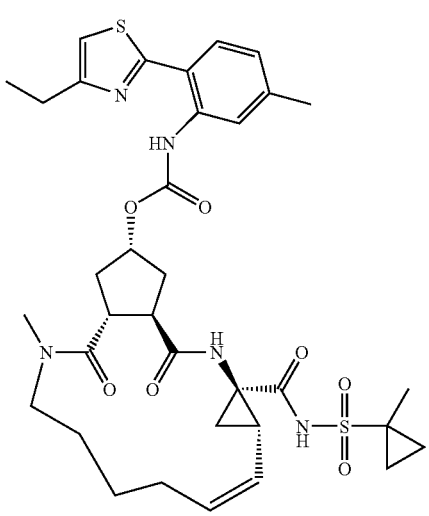

The procedure described in Example 18-10 was followed, but using the compound prepared in Example 22 (112) (22 mg, 30 μmol) instead of the corresponding cyclopropanesulphonic acid derivative, which gave the title compound (2.1 mg, 10%). LC/MS (Method I): t$_r$=2.41 min, >95%, m/z (ESI$^+$)=712 (MH$^+$).

Example 24

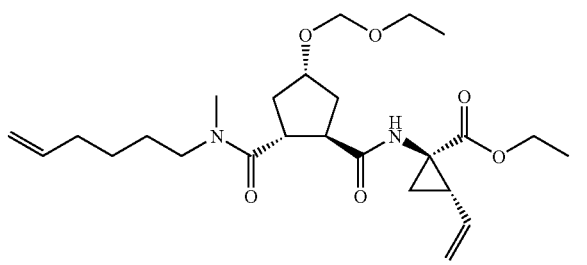

1-{[4-Ethoxymethoxy-2-(hex-5-enyl-methyl-carbamoyl)-cyclopentanecarbonyl]-amino}-2-vinyl-cyclopropanecarboxylic acid ethyl ester (114)

To a stirred solution of the alcohol (3) (1.91 g, 4.70 mmol) and N-ethyldiisopropylamine
(2.46 ml, 14.1 mmol) in dichloromethane (20 ml) at 0° C. was added chloromethyl ethyl ether (0.65 ml, 7.05 mmol).
After stirring at rt over night the reaction mixture was cooled to 0° C. and more N-ethyldiisopropylamine (0.82 ml, 4.7 mmol) and chloromethyl ethyl ether (0.22 ml, 2.4 mmol) was added, then stirred additional 16 h at rt. The reaction mixture was then directly applied on a silica gel column and eluted using stepwise gradient elution (ethyl acetate in hexane 50-100%). Concentration of the appropriate fractions gave the title compound as a slight yellow syrup (1.83 g, 84%). LR-MS: Calcd for C$_{25}$H$_{41}$N$_2$O$_6$: 465. Found: 465 [M+H].

Example 25

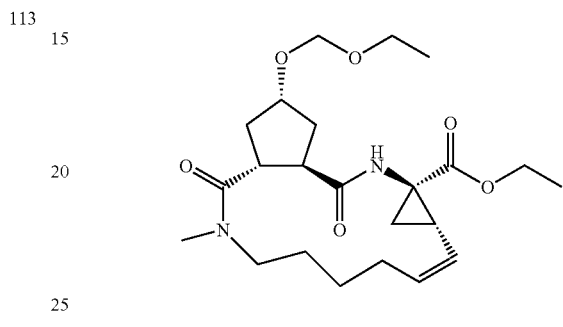

17-Ethoxymethoxy-13-methyl-2,14-dioxo-3,13-diaza-tricyclo[13.3.0.0*4,6*]octadec-7-ene-4-carboxylic acid ethyl ester (115)

A degassed solution of dialkene (114)(1.83 g, 3.93 mmol) in dichloroethane (1.8 L, stored over 4 Å molecular sieves before use) was added Howeyda-Grubbs 1$^{st}$ generation catalyst (0.165 g, 0.27 mmol), then shortly degassed and stirred at approximately 85° C. bath temperature overnight (monitored by LC-MS). The reaction mixture was then allowed to cool somewhat after which solid phase catalyst scavenger (1.3 g, MP-TMT, Argonaut Technologies) and stirred additional 1.5 h, then filtered and concentrated. Flash chromatography of the residue (YMC-GEL silica) using stepwise gradient elution (ethyl acetate in hexane, 50-100%) and concentration of the appropriate fractions gave the title compound as a brown syrup which crystallized upon standing (1.33 g, 77%, purity approx. 90%). This material was crystallized from 4:1 ethyl acetate (40 ml) giving a brown solid (0.79 g, 1.8 mmol) and chromatography of the mother liqure gave additional product (0.36 g, 0.81 mmol). LR-MS: Calcd for C$_{23}$H$_{37}$N$_2$O$_6$: 437. Found: 437 [M+H].

Example 26

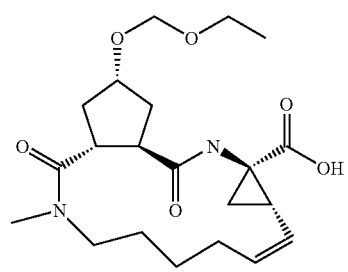

17-Ethoxymethoxy-13-methyl-2,14-dioxo-3,13-diaza-tricyclo[13.3.0.0*4,6*]octadec-7-ene-4-carboxylic acid (116)

A solution of the ester (115) (1.48 g, 3.39 mmol) in 1:1:1 THF-methanol-aq. 1M LiOH (102 ml) was stirred at 60° C., then at room temperature overnight. The reaction mixture was then concentrated into approximately ⅓ of the volume, diluted with water (30 ml) and acidified to approx. pH 4 using aq. 10% citric acid (60 ml), then washed with ethyl acetate (3×50 ml). The combined organic layers were washed with brine (1×100 ml), then dried ($Na_2SO_4$), filtered and concentrated. Column chromatography of the residue using 9:1 ethyl acetate-methanol as eluent gave the title compound as a slight yellow (The coloring from the previous step was removed during work up and chromatography). Yield: 1.35 g, 97%. LR-MS: Calcd for $C_{21}H_{31}N_2O_6$: 407. Found: 407 [M–H].

Example 27

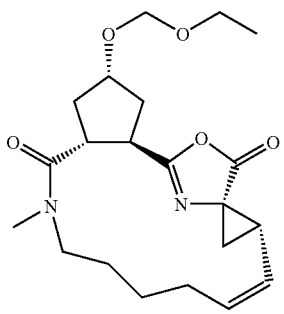

Compound 117

To a solution of the carboxylic acid (116) (1.31 g, 3.20 mmol) in dichloromethane (20 ml) at room temperature was added N-ethyl-N'-(3-dimethylaminopropyl)carbodiimide×HCl (0.74 g, 3.85 mmol), then stirred for 2.5 h after which TLC (9:1 ethyl acetate-methanol, stained using ammonium-molybdate-cerium sulfate in aq. 10% sulfuric acid) and LC-MS indicated complete conversion of the acid into the product. The reaction mixture was then diluted with dichloromethane (20 ml), washed with water (3×20 ml), then dried ($Na_2SO_4$) filtered and concentrated into a foamy syrup (1.26 g, quantitative) which was used immediately in the next step.

Example 28

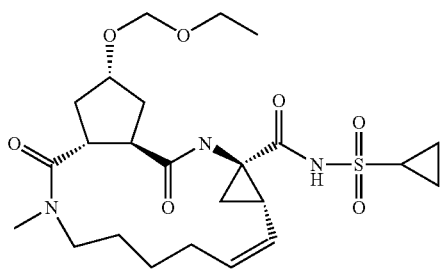

Cyclopropanesulfonic acid (17-ethoxymethoxy-13-methyl-2,14-dioxo-3,13-diaza-tricyclo[13.3.0.0*4,6*]octadec-7-ene-4-carbonyl)-amide(118)

To a stirred solution of the oxazolinone prepared in example 27 (0.85 g, 2.18 mmol) in dichloromethane (10 ml) was added cyclopropylsulfonamide (0.29 g, 2.39 mmol) and 1,8-diazabicyclo[5.4.0]-undec-7-ene (0.49 ml, 3.3 mmol), then stirred at room temperature overnight. The reaction mixture was monitored by TLC (9:1 ethyl acetate-methanol), then diluted with dichloromethane (25 ml), washed successively with aq. 10% citric acid (3×25 ml) and brine (1×25 ml), then dried ($Na_2SO_4$), filtered and concentrated into a foam. Flash chromatography of the residue using stepwise gradient elution (ethyl acetate in toluene 60-100%) followed by concentration and drying of the appropriate fractions gave the title compound as a colorless foam (0.90 g, 81%). LR-MS: Calcd for $C_{24}H_{38}N_3O_7S$: 512. Found: 512 [M+H].

Example 29

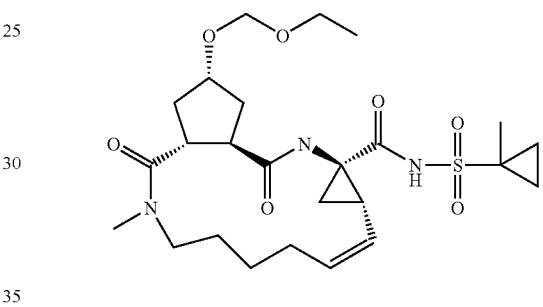

1-Methyl-cyclopropanesulfonic acid (17-ethoxymethoxy-13-methyl-2,14-dioxo-3,13-diaza-tricyclo[13.3.0.0*4,6*]octadec-7-ene-4-carbonyl)-amide (119)

To a stirred solution of the oxazolinone (0.395 g, 1.01 mmol) in dichloromethane (5 ml) was added cyclopropylmethylsulfonamide (0.15 g, 1.1 mmol) and 1,8-diazabicyclo[5.4.0]-undec-7-ene (0.23 ml, 1.5 mmol) then stirred at rt overnight. TLC (9:1 ethyl acetate-methanol) then indicated some starting material remained and more cyclopropylmethylsulfonamide (0.055 g, 0.4 mmol) and 1,8-diazabicyclo[5.4.0]-undec-7-ene (0.075 ml, 0.5 mmol) was added, then stirred another night at room temperature. Work up and chromatography as described in example 28 above gave the title compound as a colorless foam (0.40 g, 75%). LR-MS: Calcd for $C_{25}H_{38}N_3O_7S$: 524. Found: 524 [M–H].

Example 30

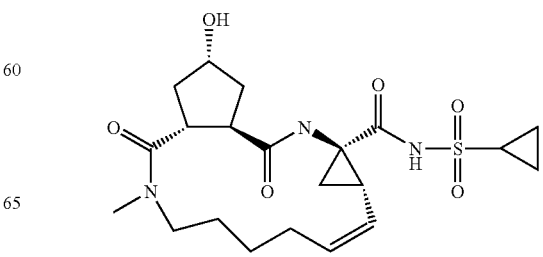

Cyclopropanesulfonic acid (17-hydroxy-13-methyl-2,14-dioxo-3,13-diaza-tricyclo[13.3.0.0*4,6*]octadec-7-ene-4-carbonyl)-amide (120)

To a stirred solution of the acetal (118) (0.099 g, 0.19 mmol) in 1:1:1 THF-methanol-water at rt was added concentrated hydrochloric acid (0.325 ml). The reaction mixture was monitored by TLC (9:1 ethyl acetate-methanol) and after 3 h; more hydrochloric acid (0.2 ml) was added. After 2 more hours the reaction mixture was neutralized using sodium hydrogen carbonate (s) (approx. 0.5 g). The reaction mixture was concentrated into ½ the volume, then partitioned between aq. 10% citric acid (10 ml) and dichloromethane (5 ml). The water layer was washed with dichloromethane (4×5 ml) and the combined organic layers were dried ($Na_2SO_4$), filtered and concentrated. Flash chromatography of the residue using stepwise gradient elution (methanol in ethyl acetate 5 to 10%) followed by concentration and drying of the appropriate fractions gave a colorless foam (0.068 g, 77%).

NMR data (500 MHz, DMSO-$d_6$): $^1H$, δ 0.9-1.4 (m, 8H), 1.5-1.9 (m, 6H), 2.18 (m, 1H), 2.4-2.6 (m, 2H), 2.9 (s, 3H), 3.0-3.2 (m, 2H), 4.2-4.4 (m, 2H), 4.85 (d, 1H, OH), 5.02 (m, 1H), 5.58 (m, 1H), 8.79 (s, 1H, NH), 11.77 (s, 1H, NH). LR-MS: Calcd for $C_{21}H_{32}N_3O_6S$: 454. Found: 454 [M+H].

Example 31

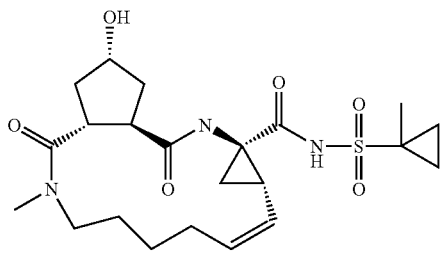

1-Methyl-cyclopropanesulfonic acid (17-hydroxy-13-methyl-2,14-dioxo-3,13-diaza-tricyclo[13.3.0.0*4,6*]octadec-7-ene-4-carbonyl)-amide (121)

To a stirred solution of the cyclopropylmethyl derivative (119) (0.38 g, 0.72 mmol) in 1:1:1 THF-methanol-$H_2O$ (6 ml) was added conc. hydrochloric acid (0.89 ml), then stirred at r for 6.5 h. The reaction mixture was then neutralized using sodium hydrogen carbonate (approx. 0.9 g solid) and concentrated into approx. half the volume. The residue was partitioned between aq. 10% citric acid (40 ml) and dichloromethane (10 ml). The water layer was washed with dichloromethane (3×10 ml), and the combined organic layers were dried (sodium sulfate), filtered and concentrated. Flash chromatography of the residue using stepwise gradient elution (methanol in ethyl acetate 5-10%) gave after concentration of the appropriate fractions the title compound as a colorless foam (0.315 g, 93%). LR-MS: Calcd for $C_{22}H_{34}N_3O_6S$: 468. Found: 468 [M+H].

Example 32

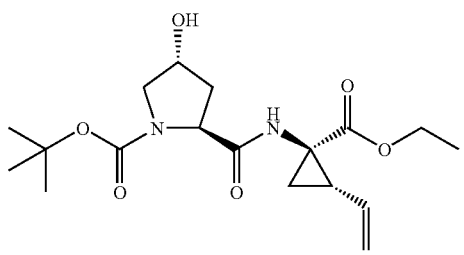

2-(1-Ethoxycarbonyl-2-vinyl-cyclopropylcarbamoyl)-4-hydroxy-pyrrolidine-1-carboxylic acid tert-butyl ester (122)

Boc-protected 4-hydroxy proline (4 g, 17.3 mmol), HATU (6.9 g, 18.2 mmol) and 1-amino-2-vinyl-cyclopropanecarboxylic acid ethyl ester prepared as described in WO03/099274, (3.5 g, 18.3 mmol) were dissolved in DMF (60 ml) and cooled to 0° on an ice-bath. Diisopropylethyl amine (DIPEA) (6 ml) was added. The ice-bath was removed and the mixture was left at ambient temperature over-night. Dichloromethane (~80 ml) was then added and the organic phase was washed with aqueous sodium hydrogen carbonate, citric acid, water, brine and dried over sodium sulphate. Purification by flash chromatography (ether→7% methanol in ether) gave pure title compound (6.13 g, 96%)

Example 33

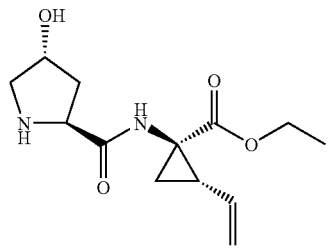

1-[(4-Hydroxy-pyrrolidine-2-carbonyl)-amino]-2-vinyl-cyclopropanecarboxylic acid ethyl ester (123)

Compound 122 (10.5 g, 28.4 mmol) was dissolved in DCM (70 ml) and cooled to 0° C., TFA (35 ml) was added. After appr 1 h the solution was evaporated and neutralized with aqueous sodium carbonate and evaporated on silica. Purification of the crude product by column chromatography on silica (MeOH/DCM: 15/85) gave 9.7 g of still unpure compound title compound. This material was used in the next step.

Example 34

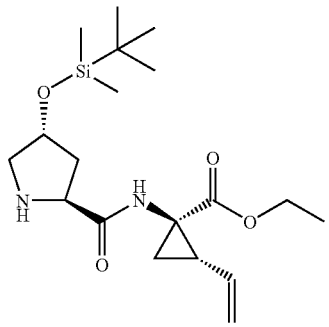

1-{[4-(tert-Butyl-dimethyl-silanyloxy)-pyrrolidine-2-carbonyl]-amino}-2-vinyl-cyclopropanecarboxylic acid ethyl ester (124)

Compound 123 (6.5 g) and imidazole (3.4 g, 50 mmol) was dissolved in DCM (100 ml), TBDMSCl (3.9 g, 26 mmol) was added and the reaction mixture was left stirring at room temperature overnight. The reaction mixture was washed with aqueous citric acid and brine, dried over MgSO₄ and evaporated. The crude product was purified by column chromatography on silica (EtOAc/n-Heptane 50/50-100/0) to give the title compound (4.26 g, 56%).

Example 35

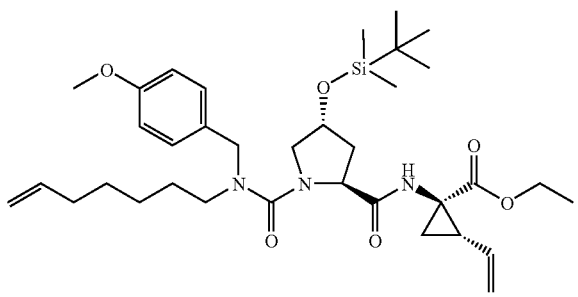

1-({4-(tert-Butyl-dimethyl-silanyloxy)-1-[hept-6-enyl-(4-methoxy-benzyl)-carbamoyl]-pyrrolidine-2-carbonyl}-amino)-2-vinyl-cyclopropanecarboxylic acid ethyl ester (125)

Compound 124 (5.88 g, 15.4 mmol) was dissolved in THF (200 ml), NaHCO₃ (s) (appr. 10 ml) was added followed by phosgene-solution (20% in toluene, 15.9 ml, 30.7 mmol). The reaction mixture was stirred vigorously for 1 h and then filtrated, evaporated and redissolved in DCM (200 ml). NaHCO₃ (s) (appr. 10 ml) was added followed by hept-6-enyl-(4-methoxy-benzyl)-amine (5.58 g, 23.9 mmol). The reaction mixture was stirred at room temperature overnight, filtrated and evaporated on silica. The crude product was purified by column chromatography on silica (EtOAc/n-Heptane 25/75-50/50) to give the title compound (4.9 g, 50%).

Example 36

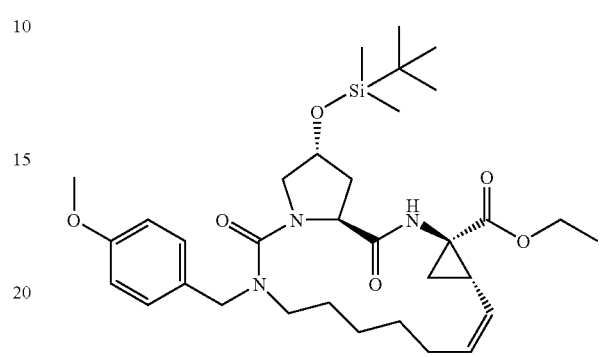

18-(tert-Butyl-dimethyl-silanyloxy)-14-(4-methoxy-benzyl)-2,15-dioxo-3,14,16-triaza-tricyclo[14.3.0.0*4,6*]nonadec-7-ene-4-carboxylic acid ethyl ester (126)

The diene (125) (1 g, 1.6 mmol) was dissolved in degassed DCE (1000 ml), Hoveyda-Grubbs 2$^{nd}$ generation (100 mg, 0.16 mmol) was added and the reaction mixture was refluxed under an atmosphere of argon overnight. The reaction mixture was evaporated on silica and purified by column chromatography on silica gel (30% EtOAc in Heptane→50% EtOAc in Heptane) to give the title compound (470 mg, 0.767 mmol, 48%). M+H=614.

Example 37

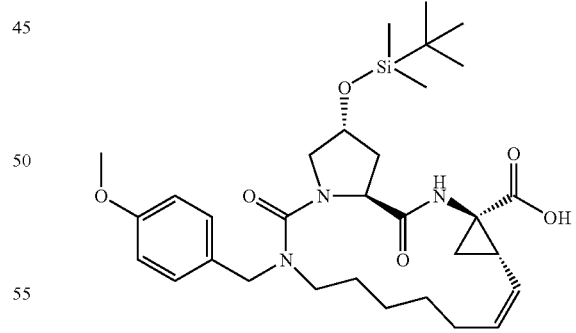

18-(tert-Butyl-dimethyl-silanyloxy)-14-(4-methoxy-benzyl)-2,15-dioxo-3,14,16-triaza-tricyclo[14.3.0.0*4,6*]nonadec-7-ene-4-carboxylic acid (127)

Compound 126 (450 mg, 0.734 mmol) was dissolved in THF/MeOH/H₂O (2:1:1). LiOH, 1M (7.4 ml, 7.4 mmol) was added and the reaction mixture was allowed to stir at RT over night. Acidification (5% citric acid) followed by extraction with chloroform gave the title compound (321 mg, 75%). M+H=586.

Example 38

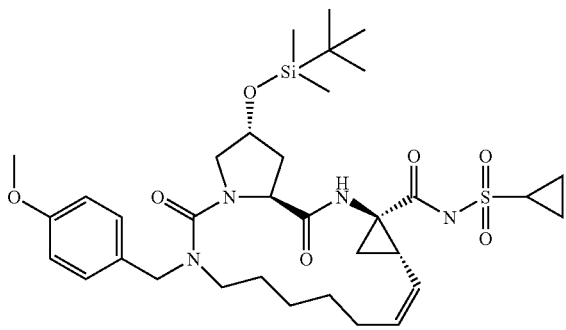

Cyclopropanesulfonic acid [18-(tert-butyl-dimethyl-silanyloxy)-14-(4-methoxy-benzyl)-2,15-dioxo-3,14,16-triaza-tricyclo[14.3.0.0*4,6*nonadec-7-ene-4-carbonyl]-amide (128)

A mixture of the acid 127 (275 mg, 0.472 mmol) and CDI (153 mg, 0.944 mmol) in dry THF (40 mL) was refluxed under argon for 2 h. Cyclopropylsulfonamide (172 mg, 1.416 mmol) and DBU (162 µl, 1.086 mmol) were added and the reaction mixture was stirred at 55° C. over night. The reaction mixture was concentrated by rotary evaporation, mixed with water, acidified with 5% citric acid and extracted into EtOAc. The organic phase was washed with brine, dried over magnesium sulfate and purified by column chromatography to give the title compound (220 mg, 68%). M+H=689.

Example 39

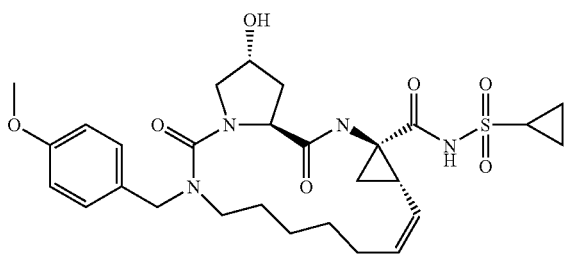

Cyclopropanesulfonic acid [18-hydroxy-14-(4-methoxy-benzyl)-2,15-dioxo-3,14,16-triaza-tricyclo[14.3.0.0*4,6*]nonadec-7-ene-4-carbonyl]-amide (129)

To a stirred solution of the silyl ether 38 (0.050 g, 0.073 mmol) in THF (1 ml) was added 1M tetrabutylammonium fluoride in THF (TBAF, 80 µl, 0.08 mmol). After 50 min, additional TBAF (0.8 ml) and after one more hour, the reaction mixture was concentrated onto silica. Flash chromatography of the residue using stepwise gradient elution (methanol in dichloromethane 2-10%) gave an off-white foam (0.035 g, 84%). %). LR-MS: Calcd for $C_{28}H_{39}N_4O_7S$: 575. Found: 575 [M+H].

Example 40

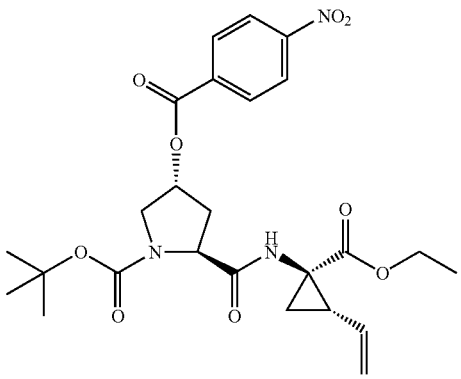

2-(1-Ethoxycarbonyl-2-vinyl-cyclopropylcarbamoyl)-4-(4-nitro-benzoyloxy-pyrrolidine-1-carboxylic acid tert-butyl ester (130)

Compound 122 (from example 32) (11.8 g, 32.0 mmol) and pyridine (27 ml, 305 mmol) was dissolved in DCM (200 ml) and cooled to 0° C., 4-nitrobenzoyl chloride (6.6 g, 35.6 mmol) was added and the solution was stirred at room temperature overnight. The reaction mixture was washed with NaHCO3 (aq), aqueous citric acid and brine, dried over MgSO4 and evaporated on silica. The crude product was purified by column chromatography on silica (EtOAc/n-Heptane 50/50) to give 11.84 g, 72% of the title compound.

Example 41

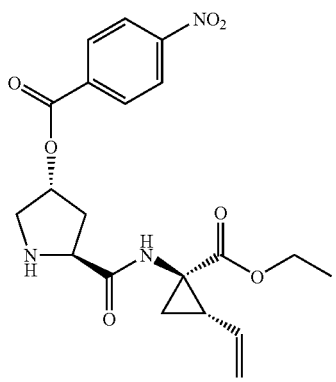

4-Nitro-benzoic acid 5-(1-ethoxycarbonyl-2-vinyl-cyclopropylcarbamoyl)-pyrrolidin-3-yl ester (131)

Compound 130 (11.84 g, 22.9 mmol) was deprotected in TFA (30 ml) dissolved in DCM (100 ml) and then worked up by methods known in the chemical art to give the title compound (9.37 g, 98%).

Example 42

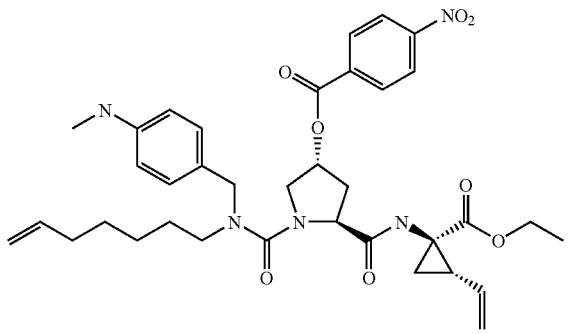

4-Nitro-benzoic acid 5-(1-ethoxycarbonyl-2-vinyl-cyclopropylcarbamoyl)-1-[hept-6-enyl-(4-methoxy-benzyl)-carbamoyl]-pyrrolidin-3-yl ester (132)

Compound 131 (4.68 g, 11.2 mmol) was dissolved in THF (100 ml), NaHCO3 (s) (appr. 5 ml) was added followed by phosgene-solution (20% in toluene, 11.6 ml, 22.5 mmol). The reaction mixture was stirred vigorously for 1 h and then filtrated, evaporated and redissolved in DCM (100 ml). NaHCO3 (s) (appr. 5 ml) was added followed by hept-6-enyl-(4-methoxy-benzyl)-amin (3.92 g, 16.8 mmol). The reaction mixture was stirred at room temperature overnight, filtrated and evaporated on silica. The crude product was purified by column chromatography on silica (EtOAc/n-Heptane 25/75) to give the title compound (6.9 g, 91%).

Example 43

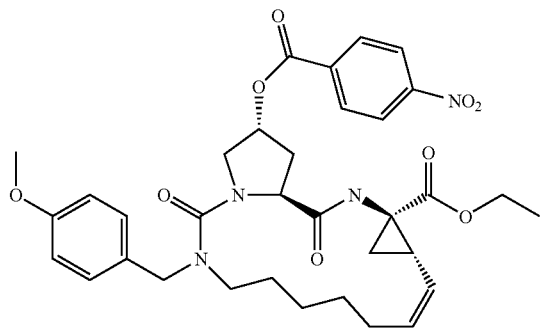

14-(4-Methoxy-benzyl)-18-(4-nitro-benzoyloxy)-2,15-dioxo-3,14,16-triaza-tricyclo[14.3.0.0*4,6*]nonadec-7-ene-4-carboxylic acid ethyl ester (133)

Compound 132 (406 mg, 0.6 mmol) was dissolved in DCE (250 ml) and degassed. Hoveyda-Grubbs Catalyst $2^{nd}$ generation (26 mg, 0.042 mmol) was added and the solution was heated to reflux. After 3 h the solution was evaporated and used direct in the next step.

Example 44

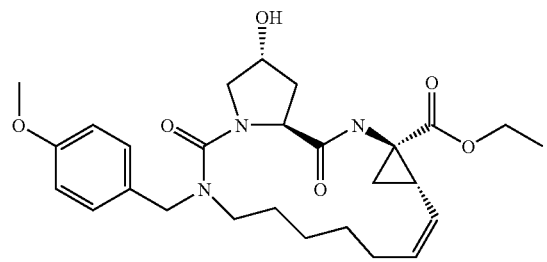

18-Hydroxy-14-(4-methoxy-benzyl)-2,15-dioxo-3,14,16-triaza-tricyclo[14.3.0.0*4,6*]nonadec-7-ene-4-carboxylic acid ethyl ester (134)

Crude compound 133 (445 mg) was dissolved in THF (20 ml), MeOH (10 ml) and water (10 ml). After cooling to 0° C. 1M LiOH (2 ml) was added. After 1.5 h the hydrolysis was completed and HOAc (1 ml) was added and the solution was evaporated to appr 10 ml. Water was added and the mixture was extracted with DCM (2×30 ml). The pooled organic phase was washed with NaHCO3 (aq), water, brine and dried over MgSO4. The crude product was purified by column chromatography on silica (DCM/MeOH: 100/0-80/20) to give the title compound (201 mg, 67%).

Example 45

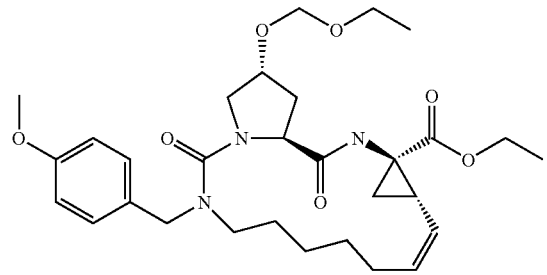

18-Ethoxymethoxy-14-(4-methoxy-benzyl)-2,15-dioxo-3,14,16-triaza-tricyclo[14.3.0.0*4,6*]nonadec-7-ene-4-carboxylic acid ethyl ester (135)

To a stirred solution of the alcohol 134 (1.35 g, 2.70 mmol, 75% purity) and N-ethyl-diisopropylamine (1.42 ml, 8.1 mmol) in dichloromethane (15 ml) at 0° C. was added chloromethyl ethyl ether (0.5 ml, 5.4 mmol). After stirring at rt on the reaction mixture was cooled to 0° C. and more N-ethyl-diisopropylamine (1 ml, 5.7 mmol) and chloro-methyl ethyl ether (0.3 ml, 3.2 mmol) was added, then stirred additional 16 h at rt. The reaction mixture was then directly applied on a silicagel column and eluted using stepwise gradient elution (ethyl acetate in hexane 50-80%). Concentration of the appropriate fractions gave the title compound as a slight brown syrup which crystallized upon standing (0.8 g, 53%). LR-MS: Calcd for $C_{30}H_{44}N_3O_7$: 558. Found: 558 [M+H].

Example 46

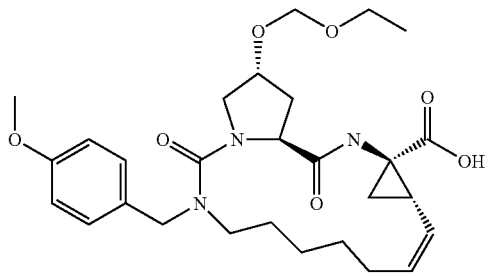

18-Ethoxymethoxy-14-(4-methoxy-benzyl)-2,15-dioxo-3,14,16-triaza-tricyclo[14.3.0.0*4,6*]nonadec-7-ene-4-carboxylic acid (136)

A solution of the ester 135 (0.775 g, 1.39 mmol) in 1:1:1 THF-Methanol-aq. 1M LiOH (36 ml) was stirred at rt for 3.5 h after which TLC (95:5 and 9:1 dichloromethane-methanol) and LC-MS indicated complete conversion into the carboxylic acid. The reaction mixture was then concentrated into approximately ⅓ of the volume, then diluted with water (10 ml) and acidified to approx. pH 4 using aq. 10% citric acid (60 ml) upon which a precipitate formed. The mixture was washed with ethyl acetate (3×25 ml) and the combined organic layers were washed with brine (2×50 ml), then dried (Na₂SO₄), filtered and concentrated. The residue was concentrated from toluene (3×10 ml) which gave the crude title compound as an off-white foam (0.75 g, quantitative). LR-MS: Calcd for $C_{28}H_{40}N_3O_7$: 530. Found: 530 [M–H].

Example 47

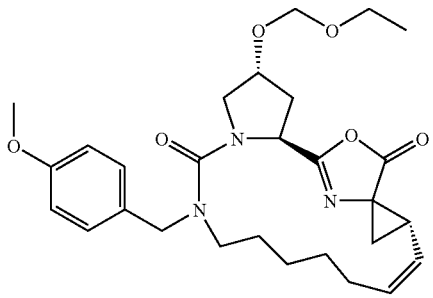

Compound 137

To a solution of the carboxylic acid 136 (approx. 1.39 mmol) in dichloromethane (10 ml) at rt was added N-Ethyl-N'-(3-dimethylaminopropyl)carbodiimide×HCl (0.32 g, 1.67 mmol), then stirred overnight after which LC-MS indicated complete conversion of the acid into the product. The reaction mixture was then diluted with dichloromethane (10 ml), washed with water (3×10 ml), then dried (Na₂SO₄) filtered and concentrated into a colorless solid (crude yield: 0.7 g) which was used immediately in the next step. LR-MS: Calcd for $C_{28}H_{38}N_3O_6$: 512. Found: 512 [M+H].

Example 48

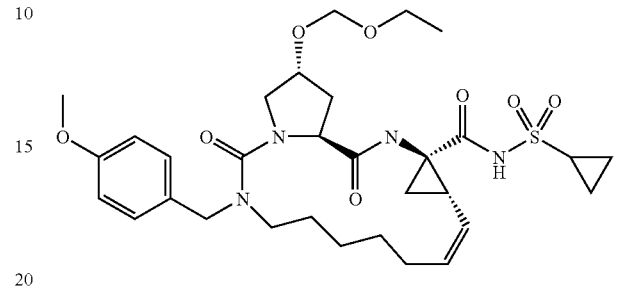

Cyclopropanesulfonic acid [18-ethoxymethoxy-14-(4-methoxy-benzyl)-2,15-dioxo-3,14,16-triaza-tricyclo[14.3.0.0*4,6*]nonadec-7-ene-4-carbonyl]-amide (138)

To a stirred solution of the crude oxazolinone 137 (0.328 g, 0.64 mmol) in dichloromethane (4 ml) was added cyclopropylsulfonamide (0.117 g, 0.96 mmol) and 1,8-diazabicyclo[5.4.0]-undec-7-ene (0.19 ml, 1.3 mmol), then stirred at rt overnight. The reaction mixture was monitored by LC-MS then diluted with dichloromethane (20 ml), washed successively with aq. 10% citric acid (3×15 ml) and brine (1×15 ml), then dried (Na₂SO₄), filtered and concentrated into an off-white foam. Column chromatography of the residue using stepwise gradient elution (ethyl acetate in toluene 60-100%) followed by concentration and drying of the appropriate fractions gave the title compound as a colorless foam (0.27 g, 66% over 3 steps).

NMR data (500 MHz, DMSO-d₆): ¹H, δ 0.9-1.6 (m, 14H), 1.80 (m, 1H), 1.90 (m, 1H), 2.0-2.2 (m, 3H), 2.25 (m, 1H), 2.95 (m, 1H), 3.05 (m, 1H), 3.3-3.4 (m, 2H), 3.50 (q, 2H), 3.7-3.8 (m, 4H), 3.97 (d, 1H), 4.3-4.4 (m, 2H), 4.55 (d, 1H), 4.63 (m, 2H), 5.12 (m, 1H), 5.70 (m, 1H), 6.88 (d, 2H), 7.19 (d, 2H), 8.12 (s, 1H). LR-MS: Calcd for $C_{31}H_{45}N_4O_8S$: 633. Found: 633 [M+H].

Example 49

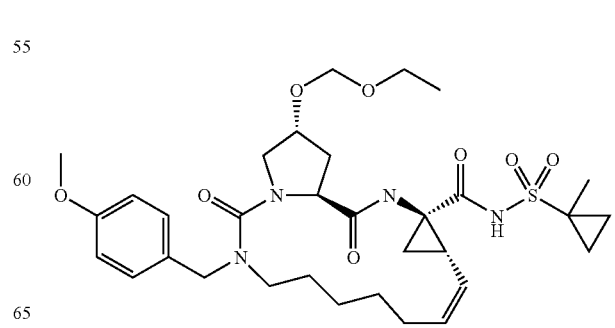

1-Methyl-cyclopropanesulfonic acid [18-ethoxymethoxy-14-(4-methoxy-benzyl)-2,15-dioxo-3,14,16-triaza-tricyclo[14.3.0.0*4,6*]nonadec-7-ene-4-carbonyl]-amide (139)

To a stirred solution of the oxazolinone (0.372 g, 0.73 mmol) in dichloromethane (4 ml) was added cyclopropylmethylsulfonamide (0.147 g, 1.09 mmol) and 1,8-Diazabicyclo[5.4.0]-undec-7-ene (0.22 ml, 1.45 mmol) then stirred at rt overnight. Work up and chromatography as described above gave the desired product as a colorless syrup which started to crystallize upon standing (0.31 g, 65% over 3 steps).

NMR data (500 MHz, DMSO-$d_6$): $^1$H, δ 0.92 (m, 2H), 1.1-1.6 (m, 15H), 1.78 (m, 1H), 1.88 (m, 1H), 2.0-2.1 (m, 3H), 2.26 (m, 1H), 3.02 (m, 1H), 3.2-3.4 (m, 2H), 3.49 (q, 2H), 3.7-3.8 (m, 4H), 3.95 (d, 1H), 4.3-4.4 (m, 2H), 4.54 (d, 1H), 4.6-4.7 (m, 2H), 5.06 (m, 1H), 5.69 (m, 1H), 6.88 (d, 2H), 7.19 (d, 2H), 8.22 (s, 1H), 11.23 (s, 1H). LR-MS: Calcd for $C_{32}H_{47}N_4O_8S$: 647. Found: 647 [M+H].

Example 50

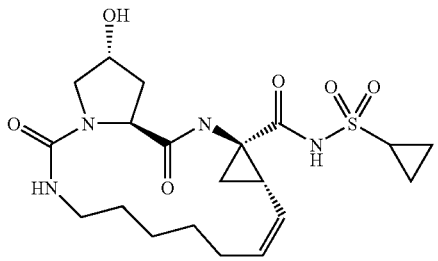

Cyclopropanesulfonic acid (18-hydroxy-2,15-dioxo-3,14,16-triaza-tricyclo-[14.3.0.0*4,6*]nonadec-7-ene-4-carbonyl)-amide (140)

A solution of the acetal 139 (0.038 g, 0.06 mmol) in 1:1:1 THF-methanol-2 M aq. hydrochloric acid (1.5 ml) was stirred at rt for 30 min, then additional conc. hydrochloric acid (0.1 ml) was added and then stirred at rt overnight. The reaction mixture was then neutralized using aq. saturated sodium hydrogen carbonate, then concentrated onto silica. Flash chromatography of the residue using 9:1 ethyl acetate-methanol gave a colorless foam (0.020 g, 73%). LR-MS: Calcd for $C_{20}H_{29}N_4O_6S$: 453. Found: 453 [M–H].

Example 51

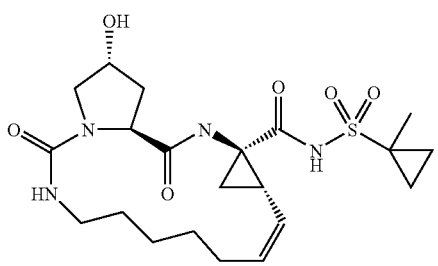

1-Methyl-cyclopropanesulfonic acid (18-hydroxy-2,15-dioxo-3,14,16-triaza-tricyclo[14.3.0.0*4,6*]nonadec-7-ene-4-carbonyl)-amide (141)

The above material (0.301 g, 0.465 mmol) was deprotected using 2:1:0.1 dichloro-methane-trifluoroacetic acid-$H_2O$ (6.2 ml) at rt for 4 h, then conc onto silica and flash chromatography using 9:1 ethyl acetate-methanol gave the product as a colorless foam (0.065 g, 30%). LR-MS: Calcd for $C_{21}H_{33}N_4O_6S$: 469. Found: 469 [M+H]. Preferably this material should be deprotected using the procedure described for the corresponding cyclopentane derivative.

Example 52

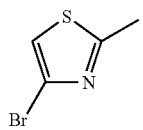

4-Bromo-2-methyl-thiazole (142)

2,4-Dibromothiazole (2.4 g, 9.8 mmol) was dissolved in abs. THF (50 ml) and the resulting solution was stirred under argon at −78° C. A solution of BuLi (4.2 ml, 6 mmol, 2.5 M in hexanes) was added and the stirring was continued for 1 h whereafter a solution of dimethylsulfate (2.7 ml) in THF (5 ml) was added dropwise. After stirring for 4 h at −78° C., the reaction mixture was warmed to room temperature and stirred overnight. The reaction mixture was diluted with saturated aqueous sodium bicarbonate (50 ml). The aqueous layer was extracted into diethyl ether and the combined organic extracts were washed with brine dried with magnesium sulfate and concentrated by rotary evaporation. Purification by column chromatography on silica gel gave the title compound as yellow oil (0.956 g, 55%).

Example 53

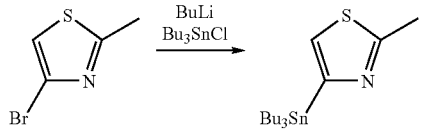

2-Methyl-4-tributylstannanyl-thiazole (143)

To a solution of 4-bromo-2-methylthiazole (950 mg, 5.3 mmol) in absolute THF (40 mL) at −78° C. was added dropwise n-butyllithium (2.7 mL, 1.6 M in hexane). The solution was stirred at −78° C. for 1 h, then tributyltinchloride (2.2 g, 6.8 mmol) was added, and the mixture was allowed to warm to room temperature. Water (90 mL) was poured into the reaction mixture and the phases were separated. The aqueous layer was extracted with diethyl ether (4×30 mL). The combined organic phases were dried over magnesium sulfate and the solvent was removed in vacuo. The resulting oil was purified by fractionated Kugelrohr distillation to give the title compound (2.3 g). The product was used without further purification.

Example 54

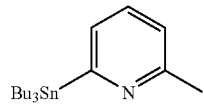

2-Methyl-6-tributylstannanyl-pyridine (144)

To 2-bromo-6-picoline (28.4 g, 165 mmol) in absolute THF (250 mL) at −78° C. was added dropwise n-butyllithium (110 mL, 178 mmol, 1.6 M in hexane). The solution was stirred at −78° C. for 90 min, then tributyltinchloride (53.6 mL, 198 mmol) was added and the mixture was allowed to warm to room temperature. Water (90 mL) was poured into the reaction mixture, and the phases were separated. The aqueous layer was extracted with diethyl ether (4×200 mL). The combined organic phases were dried over $Na_2SO_4$, and the solvent was removed in vacuo. The resulting oil was purified by fractionated Kugelrohr distillation. Yield 50%.

General Procedure [A] for the Preparation of Substituted Anilines:

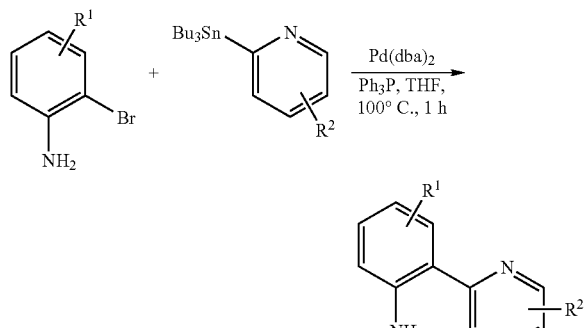

A screw cap tube was charged with $Pd(dba)_2$ (10 mg, 2 mol %), CuI (10 mg, 6 mol-%), and $PPh_3$ (30 mg, 12 mol-%), the desired tributyltinpyridine or thiazole derivative (1.6 eq) and bromoaniline (200 mg, 1 eq), The mixture was degassed and back-filled with argon. THF (4 mL) was added, and the reaction mixture was heated by microwave irradiation for 4 h at 150° C. The reaction mixture was cooled to room temperature, stirred overnight with aqueous KF (saturated 15 mL), and filtered. The solid was discarded after washing with EtOAc (three times). The liquid was poured into $H_2O$ and extracted with EtOAc. The combined organic layers were washed with $H_2O$ and brine, dried over $MgSO_4$, and filtered and the solvent was removed in vacuo. The residue was purified by column chromatography (20 g of YMC silica, EtOAc: petroleum ether) which gave the desired aniline derivative.

General Procedure [B] for the Preparation of Substituted Anilines:

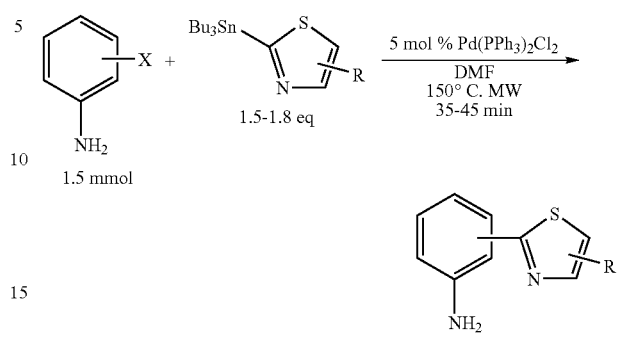

The stannane (1.5-1.8 eq) was added to a solution of the bromoaniline (1.5 mmol) and catalyst in degassed DMF in a 5 mL microwave tube. Argon was bubbled into the mixture for 1 min, the tube was capped and subjected to microwave irradiation. The black precipitates were removed by centrifugation or filtration. The liquid part was evaporated and then partitioned between EtOAc and 10% $NH_4OH$, extracting the aqueous phase several times with EtOAc. The organic phase was dried over $Na_2SO_4$ and concentrated. Flash column chromatography on silica gel gave the substituted aniline derivatives.

Example 55

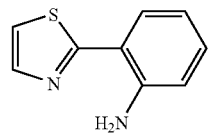

2-Thiazol-2-yl-phenylamine (145)

2-Tributylstannanyl-thiazole (600 mg, 1.6 mmol) was reacted with 2-bromoaniline (200 mg, 1.2 mmol) according to general procedure [B] for the preparation of substituted anilines described above, which gave the title compound (51 mg, 25%). [M+1] 177.

Example 56

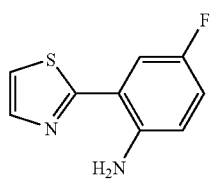

4-Fluoro-2-thiazol-2-yl-phenylamine (146)

2-Tributylstannanyl-thiazole (600 mg, 1.6 mmol) was reacted with 2-bromo-4-fluoroaniline (220 mg, 1.2 mmol)

according to general procedure [B] for the preparation of substituted anilines described above, which gave the title compound (18 mg, 8%). [M+1] 195.

Example 57

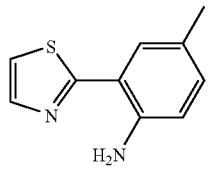

4-Methyl-2-thiazol-2-yl-phenylamine (147)

2-Tributylstannanyl-thiazole (600 mg, 1.6 mmol) was reacted with 2-bromo-4-methylaniline (220 mg, 1.2 mmol) according to general procedure [B] for the preparation of substituted anilines described above, which gave the title compound (17 mg, 8%). [M+1] 191.

Example 58

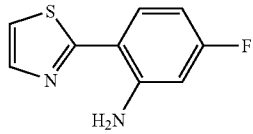

5-Fluoro-2-thiazol-2-yl-phenylamine (148) 2-Tributylstannanyl-thiazole (600 mg, 1.6 mmol) was reacted with 2-bromo-5-fluoro-aniline (209 mg, 1.1 mmol) according to general procedure [A] for the preparation of substituted anilines described above, which gave the title compound (140 mg, 51%). [M+1] 195.

Example 59

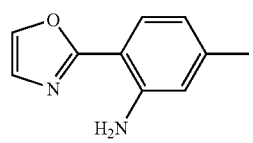

5-Methyl-2-oxazol-2-yl-phenylamine (149)

2-(Tri-n-butylstannyl)oxazole (500 mg, 1.4 mmol) was reacted with 2-bromo-4-methyl-aniline (200 mg, 1.1 mmol) according to general procedure [B] for the preparation of substituted anilines described above, which gave the title compound (90 mg, 48%). [M+1] 175.

Example 60

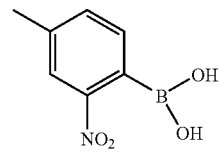

4-Methyl-2-nitrobenzene boronic acid (150)

4-Iodo-3-nitrotoluene (2 g, 7.6 mmol) was dissolved in 20 ml abs. THF, the flask was flushed with argon and cooled down to −70° C. Phenylmagnesium chlorid (4.2 ml, 8.4 mmol, 2M solution) was added slowly (during 15 min) at −64° C. and the reaction mixture was stirred for appr. 10 min. Trimethyl boronic ester was then added dropwise to the reaction mixture which then was left to stir for 1 h at temp between −60° C. and −68° C. A solution of 1M HCl was added (temp below −20° C.) and the reaction mixture was left to stir overnight at room temperature. The reaction mixture was partitioned between diethyl ether and 1M HCl. The water phase was extracted twice into ether and the combined organic extracts were washed with brine and dried over magnesium sulfate. The drying agent was filtered off and the resulting solution was concentrated by rotary evaporation to give a brown oil which was dried on high vacuum overnight. A precipitate was formed which was collected by filtration and washed with diethyl ether to give the title compound (962 mg, 69%) as white powder. M$^+$190.

Example 61

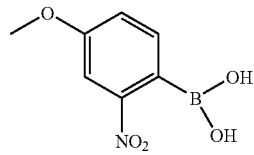

4-Methoxy-2-nitrobenzene boronic acid (151)

4-Iodo-3-nitroanisole (2 g, 7.2 mmol) was dissolved in 20 ml abs. THF, the flask was flushed with argon and cooled down to −70° C. Phenylmagnesium chlorid (4 ml, 8 mmol, 2M solution) was added slowly (during 15 min) at a temp below −60° C., and the reaction mixture stirred for appr. 10 min. Trimethyl boronic ester (1.4 g, 13.5 mmol) was then added dropwise and the reaction mixture left to stir for 1 h at temp about −60° C. A solution of 1M HCl was added (temp below −20° C.) and the reaction mixture was left to stir overnight at room temperature. The reaction mixture was partitioned between diethyl ether and 1M HCl. The water phase was extracted twice into ether. The combined organic extracts were washed with brine and dried over magnesium sulfate. The drying agent was filtered off and the resulting solution was concentrated by rotary evaporation to give brown oil which was dried on high vacuum overnight. A precipitate was formed, collected by filtration and washed with diethyl ether to give the title compound (767 mg, 54%) as beige powder.

General Procedure [C] for the Preparation of Substituted Anilines:

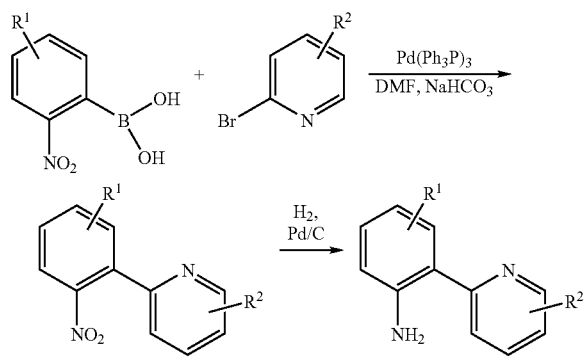

A boronic acid derivative (1.5 eq.) and an aryl bromide (1 eq.) were dissolved in 3 ml dry DMF (in 5 ml microwave vial), the solution was flushed with argon for 10 min. Tetrakis (triphenylphosphine)palladium (5 mol %) was then added to the reaction mixture, which again was flushed with argon. 1 ml of saturated sodium bicarbonate was added and the reaction mixture was heated by microwave irradiation at 150° C. for 15 min and then left to stay overnight at room temperature. The reaction mixture was mixed with water (about 50-70 ml) and extracted into ethyl acetate (3×30 ml). The combined organic extracts were washed with brine, dried over magnesium sulfate for 3 h, filtered and concentrated by rotary evaporation. The afforded residue was purified by column chromatography on silica gel (30 g, EtOAc/petroleum ether 1:9 to 1:4) which gave then gave the substituted nitro derivative.

The nitro compound (100-200 mg) was dissolved in 10-20 ml of ethanol. The reaction flask was degassed and filled with nitrogen. 20-50 mg of 10% Pd on carbon was added and the reaction mixture was stirred overnight under an atmosphere of hydrogen at ambient temperature. The reaction mixture was filtered through Celite, concentrated by rotary evaporation and purified by column chromatography on silica (ethyl acetate:petroleum ether) which gave the aniline derivative.

Example 62

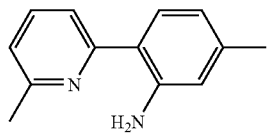

5-Methyl-2-(6-methyl-pyridin-2-yl)-phenylamine
(152)

4-methyl-2-nitropbenzen boronic acid (250 mg, 1.4 mmol) was reacted with 2-bromo-6-methylpyridine (172 mg, 1 mmol) according to general procedure [C] for the preparation of substituted anilines described above, which gave the title compound (103 mg, 52%). MS [M+1] 199.

Example 63

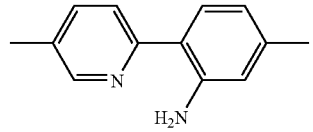

5-Methyl-2-(5-methyl-pyridin-2-yl)-phenylamine
(153)

4-methyl-2-nitropbenzen boronic acid (106 mg, 0.6 mmol) was reacted with 2-bromo-5-methylpyridine (70 mg, 0.4 mmol) according to general procedure [C] described above, which gave the title compound (50 mg, 63%). [M+1] 199.

Example 64

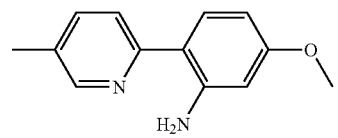

5-Methoxy-2-(5-methyl-pyridin-2-yl)-phenylamine
(154)

4-methoxy-2-nitropbenzen boronic acid (161 mg, 0.8 mmol) was reacted with 2-bromo-5-methylpyridine (105 mg, 0.61 mmol) according to general procedure [C] for the preparation of substituted anilines described above, which gave the title compound (44 mg, 34%). [M+1] 215.

General Procedure for the Synthesis of Carbamates:

Alcohol (30-60 mg) was dissolved in dry DCE and of sodium bicarbonate (20-30 mg) was added, followed by 2 ml of phosgene solution in toluene (20%). The reaction mixture was stirred at room temperature for 2-3 h (full conversion to chloroimidate according to LC-MS). The reaction mixture was then concentrated by rotary evaporation and dried from excess of phosgene in high vacuum (1.5 h). The dry reaction mixture was transferred into a "microwave" vial (2-5 ml), mixed with dry DCE (3-4 ml), aniline (2 eq), potassium carbonate (9 mg, 1.5 eq), pulvered molecular sieves (4 Å, 5-10 mg) and heated by microwaves at 100° C. for 45 min. The reaction mixture was passed through a short pad of silica (eluent DCM, then 10% methanol in DCM). The resulting fractions containing the desired carbamate were combined, concentrated by rotary evaporation and purified by column chromatography on YMC silica (15 g, ethyl acetate/petroleum ether 1:3 to remove excess of aniline, followed by dichloromethane and then 2% methanol in dichloromethane) to give desired compound as a powder. Yield 40-70%.

Example 65

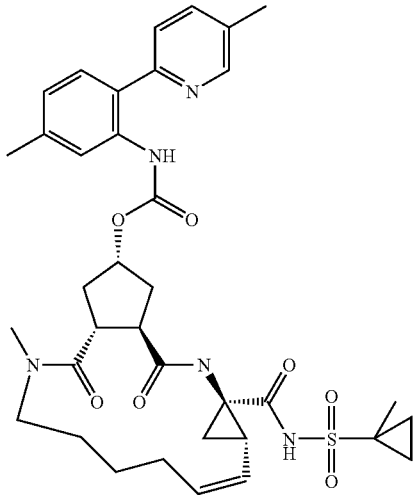

[5-Methyl-2-(5-methyl-pyridin-2-yl)-phenyl]-carbamic acid 13-methyl-4-(1-methyl-cyclopropane-sulfonylaminocarbonyl)-2,14-dioxo-3,13-diaza-tricyclo[13.3.0.0*4,6*]octadec-7-en-17-yl ester (155)

The general procedure for synthesis of carbamates described above was followed, using alcohol 121 (Ex. 31, 19 mg, 0.04 mmol) and 5-methyl-2-(5-methyl-pyridin-2-yl)-phenylamine (20 mg, 0.1 mmol), which gave the final compound (16 mg, 57%). [M+1] 692.

$^{13}$C NMR (CDCl$_3$, 400 MHz) δ 12.58, 14.25, 18.15, 18.20, 21.31*, 21.59, 22.32, 23.90, 25.85*, 27.51, 30.30, 32.01*, 33.63*, 34.91, 35.28*, 36.28, 43.90*, 45.07, 48.08, 48.15, 74.72, 120.64*, 122.00, 122.63, 123.60, 124.52, 128.52*, 131.14*, 133.05, 137.21, 138.15, 138.202, 139.99, 147.88, 153.37, 155.39, 167.24*, 172.57*, 180.13. (*=carbon doublets).

Example 66

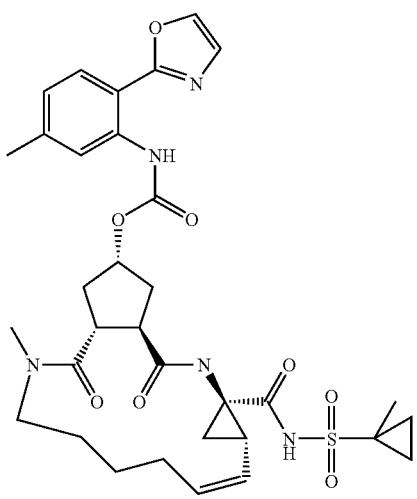

(5-Methyl-2-oxazol-2-yl-phenyl)-carbamic acid 13-methyl-4-(1-methyl-cyclopropane-sulfonylaminocarbonyl)-2,14-dioxo-3,13-diaza-tricyclo[13.3.0.0*4,6*]octadec-7-en-17-yl ester (156)

The general procedure for synthesis of carbamates described above was followed, using alcohol 121 (Ex. 31, 35 mg, 0.075 mmol) and 5-methyl-2-oxazol-2-yl-phenylamine (30 mg, 0.17 mmol, which gave the final compound (21 mg, 42%). [M+1] 668.

$^{13}$C NMR (CDCl$_3$, 400 MHz) δ 12.60*, 13.97, 14.27*, 18.20*, 21.13, 21.31*, 21.96, 22.47, 23.93, 25.83*, 27.52, 30.46, 31.97*, 33.65*, 34.87*, 35.30, 36.28, 43.94*, 45.07*, 48.09, 48.15, 75.04, 110.63, 119.04, 123.14, 124.52*, 127.01, 127.23, 129.27*, 133.04*, 134.73, 136.47, 137.32*, 137.48, 142.24, 153.25, 160.91, 167.25, 172.53, 180.07. (*=carbon doublets).

Example 67

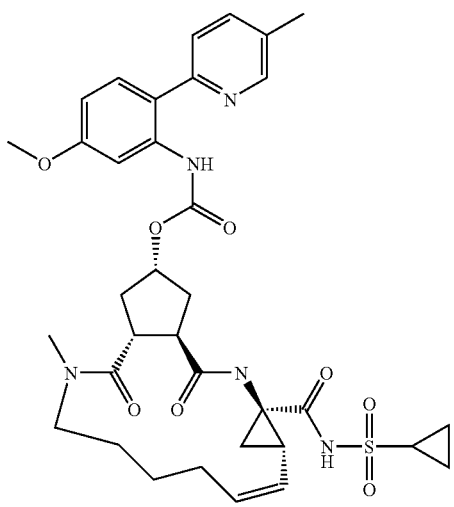

[5-Methoxy-2-(5-methyl-pyridin-2-yl)-phenyl]-carbamic acid 4-cyclopropanesulfonyl-aminocarbonyl-13-methyl-2,14-dioxo-3,13-diaza-tricyclo[13.3.0.0*4,6*]octadec-7-en-17-yl ester (157)

The general procedure for synthesis of carbamates described above was followed, using alcohol 120 (Ex. 30, 30 mg, 0.066 mmol) and 5-methoxy-2-(5-methyl-pyridin-2-yl)-phenylamine (44 mg, 0.2 mmol) which gave the final compound (20 mg, 44%). [M+1] 694.

$^{13}$C NMR (CDCl$_3$, 400 MHz) δ 14.14*, 18.13*, 21.39*, 24.09*, 25.85*, 27.57, 29.70, 31.00, 31.05, 31.93, 33.65*, 34.96, 35.58, 36.15, 43.99*, 44.87*, 47.30*, 48.05, 55.38*, 66.21, 74.75, 109.49, 117.63, 121.50, 124.24*, 128.83, 129.59, 130.67, 130.92, 133.06*, 138.20*, 139.12, 147.69, 153.39, 155.28*, 160.72, 167.71, 168.33, 172.61*, 173.06, 180.00. (*=carbon doublets).

Example 68

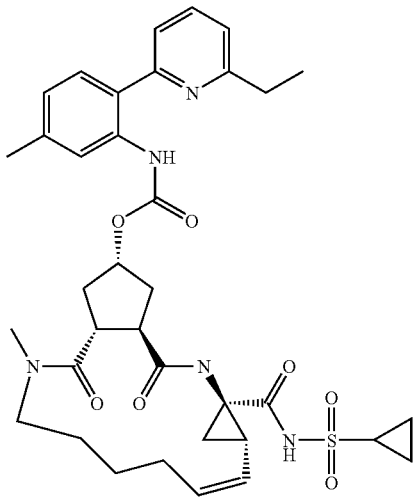

[2-(6-Ethyl-pyridin-2-yl)-5-methyl-phenyl]-carbamic acid 4-cyclopropanesulfonyl-aminocarbonyl-13-methyl-2,14-dioxo-3,13-diaza-tricyclo[13.3.0.0*4,6*]octadec-7-en-17-yl ester (158)

The general procedure for synthesis of carbamates described above was followed, using alcohol 120 (Ex. 30, 30 mg, 0.066 mmol) and 2-(6-ethyl-pyridin-2-yl)-5-methyl-phenylamine (30 mg, 0.1 mmol), which gave the final compound (20 mg, 44%). [M+1] 692.
$^1$H NMR (CDCl$_3$, 400 MHz) δ 12.2-12.27 (s+s, 1H), 10.6-10.9 (b s+s, 1H), 8.15 (s, 1H), 7.7 (dd, 1H), 7.55 (m, 1H), 7.1 (d, 1H), 6.9 (d, 1H), 6.1 (b s, 1H), 5.6-5.8 (m+m, 1H), 5.25 (b m, 1H), 5.03 (m, 1H), 4.6 (m, 1H), 3.1-3.4 (b m, 2H), 2.95 (s, 3H), 2.9 (m, 2H), 2.7 (m, 1H), 2.5-2.6 (m, 2H), 2.3-2.4 (m+s, 4H), 2.1-2.3 (m, 2H), 1.6-1.95 (m, 4H), 0.75-1.5 (tr+5m, 12H).

Example 69

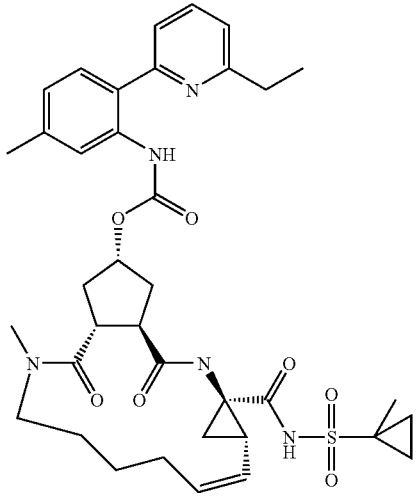

[2-(6-Ethyl-pyridin-2-yl)-5-methyl-phenyl]-carbamic acid 13-methyl-4-(1-methyl-cyclopropanesulfony-laminocarbonyl)-2,14-dioxo-3,13-diaza-tricyclo [13.3.0.0*4,6*]-octadec-7-en-17-yl ester (159)

The general procedure for synthesis of carbamates described above was followed, using alcohol 121 (Ex. 31, 31 mg, 0.66 mmol) and 2-(6-ethyl-pyridin-2-yl)-5-methyl-phenylamine (20 mg, 0.095 mmol, which gave the final compound (24 mg, 52%). [M+1] 706.
$^1$H NMR (CDCl$_3$, 500 MHz) δ 12.35, 12.30 (2:8, s, 1H), 10.8, 10.55 (8:2, s, 1H), 8.13 (s, 1H), 7.7 (dd, 1H), 7.55 (dd, 1H), 7.1 (d, 1H), 6.92 (d, 1H), 6.42, 6.1 (2:8, s, 1H), 5.6-5.8 (m, 1H), 5.3 (m, 1H), 5.03 (dd, 1H), 4.6 (m, 1H), 3.1-3.4 (m, 2H), 2.95 (s, 3H), 2.9 (m, 2H), 2.72 (m, 1H), 2.5-2.63 (m, 2H), 2.38-2.46 (m+s, 4H), 2.07-2.2 (m, 2H), 1.65-1.98 (m, 4H), 1.55-1.65 (m+s, 4H), 1.52 (s, 3H), 1.15-1.5 (m, 6H), 0.85 (m, 2H).

Example 70

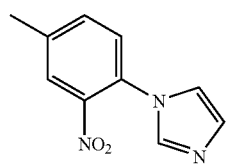

1-(4-Methyl-2-nitro-phenyl)-1H-imidazole (160)

4-fluoro-3-nitro-toluene (346 mg, 2.2 mmol) and imidazole (299 mg, 4.4 mmol) was dissolved in DMF (5 mL) and the reaction heated to 90° C. for 16 h. The solvent was removed in vacuo and the residue partitioned between ethyl acetate and 1 M HCl (aq). The aqueous layer was separated and basified with NaOH (s) and extracted with DCM. The DCM was concentrated in vacuo and the residue purified by flash chromatography (Silica, EtOAc:Heptane) to afford the title compound (337 mg, 75%). LC/MS: (00-60% B in A): $t_R$=1.69 min, >90%, m/z (ESI)=204 (MH$^+$).

Example 71

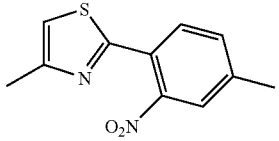

4-Methyl-2-(4-methyl-2-nitro-phenyl)-thiazole (161)

Compound 56 (Ex. 14-2, 214 mg, 1.09 mmol) was dissolved in dioxane (15 mL) and 1 M HCl (aq) (50 uL). To this solution was added 2,2-dimethoxy-4-bromo-propane (220 mg, 1.2 mmol) and the reaction sealed and heated in microwave for 15 min at 150° C. The solvent was removed in vacuo and the residue partitioned between DCM and NaHCO$_3$ (aq).

The organic layer was separated, dried (NaSO₄), filtered and concentrated in vacuo to afford a residue which was further purified by flash chromatography (Silica, EtOAc:Hexane) to afford the title compound (183 mg, 72%). LC/MS: (50-90% B in A): $t_R$=0.96 min, >90%, m/z (ESI⁺)=235 (MH⁺).

Example 72

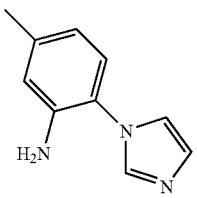

2-Imidazol-1-yl-5-methyl-phenylamine (162)

Compound 160 (337 mg, 1.66 mmol) was dissolved in EtOH (40 mL) in a 100 mL flask. 2 spatulas of 20% PdOH on carbon and a stirrbar was added followed repeated N₂(g) purging and evacuation of the flask. H₂(g) was then introduced into the flask by a balloon and the reaction stirred at room temperature under H₂-atmosphere for 2.5 h. The H₂(g) inlet was closed and the flask evacuated and N₂(g) purged 3 times. LC/MS analysis showed complete hydrogenation and the mixture was filtered through a plug of Celite before removal of the solvent in vacuo to afford the aniline 7 (quant). LC/MS (00-60% B in A): $t_R$=1.73 min, >95%, m/z (ESI⁺)= 174 (MH⁺).

Example 73

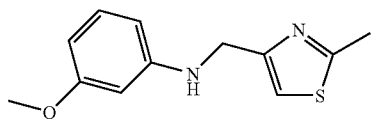

(3-Methoxy-phenyl)-(2-methyl-thiazol-4-ylmethyl)-amine (163)

4-Chloromethyl-2-methyl-thiazole.HCl (184 mg, 1 mmol) was dissolved in DMF (5 mL). To this solution was added K₂CO₃ (s) (276 mg, 2 mmol) and 3-methoxyaniline (123 mg, 1 mmol). The reaction was heated to 100° C. for 19 h. The solvent was removed in vacuo and the residue partitioned between ethyl acetate and aqueous sodium bicarbonate solution. The organic layer was separated, dried (NaSO₄), filtered and concentrated. The residue was purified by flash chromatography (Si, ethyl acetate:hexane) to afford the title compound (78 mg, 33%). LC/MS (20-80% B in A): $t_R$=1.07 min, 90% m/z (ESI⁺)=235 (MH⁺).

Example 74

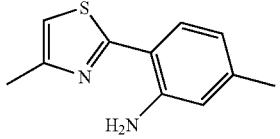

5-Methyl-2-(4-methyl-thiazol-2-yl)-phenylamine, (164)

The title compound was prepared according to the procedure described in Example 72, except that 4-methyl-2-(4-methyl-2-nitro-phenyl)-thiazole was used instead of 1-(4-methyl-2-nitro-phenyl)-1H-imidazole. LC/MS (50-90% B in A): $t_R$=0.71 min, 95%, m/z (ESI⁺)=205 (MH⁺).

Example 75

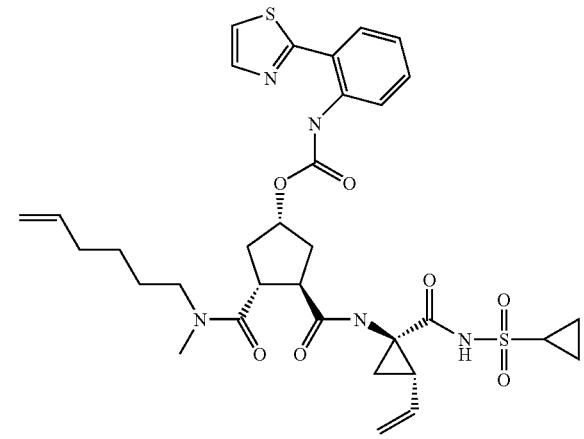

(2-Thiazol-2-yl-phenyl)-carbamic acid 3-(1-cyclopropanesulfonylaminocarbonyl-2-vinyl-cyclopropyl-carbamoyl)-4-(hex-5-enyl-methyl-carbamoyl)-cyclopentyl ester (165)

The title compound was prepared according to the procedure described in Example 17-1, except that 2-thiazol-2-yl-phenylamine was used instead of 2-(5-ethyl-thiazol-2-yl)-5-trifluoromethyl-phenylamine. LC/MS (50-90% B in A): $t_R$=2.11 min, >90%, m/z (ESI⁺)=684 (MH⁺).

Example 76

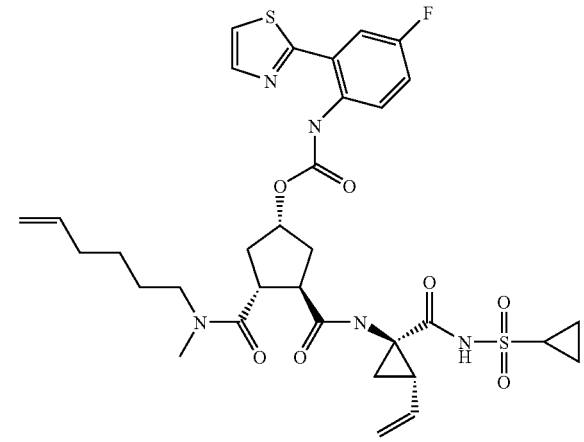

141

(4-Fluoro-2-thiazol-2-yl-phenyl)-carbamic acid 3-(1-cyclopropanesulfonylamino carbonyl-2-vinyl-cyclopropylcarbamoyl)-4-(hex-5-enyl-methyl-carbamoyl)-cyclo pentyl ester (166)

The title compound was prepared according to the procedure described in Example 17-1, except that 4-fluoro-2-thiazole-2-yl-phenylamine was used instead of 2-(5-ethyl-thiazol-2-yl)-5-trifluoromethyl-phenylamine. LC/MS (50-90% B in A): $t_R$=2.14 min, >90%, m/z (ESI$^+$)=702 (MH$^+$).

Example 77

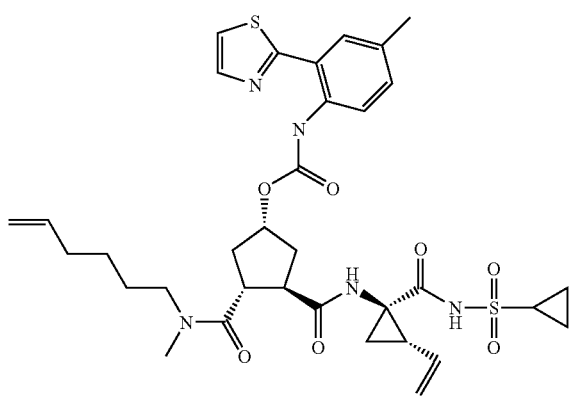

(4-Methyl-2-thiazol-2-yl-phenyl)-carbamic acid 3-(1-cyclopropanesulfonyl amino-carbonyl-2-vinyl-cyclopropylcarbamoyl)-4-(hex-5-enyl-methyl-carbamoyl)-cyclo-pentyl ester (167)

The title compound was prepared according to the procedure described in Example 17-1, except that 4-methyl-2-thiazol-2-yl-phenylamine was used instead of 2-(5-ethyl-thiazol-2-yl)-5-trifluoromethyl-phenylamine. LC/MS (50-90% B in A): $t_R$=2.30 min, >90%, m/z (ESI$^+$)=698 (MH$^+$).

Example 78

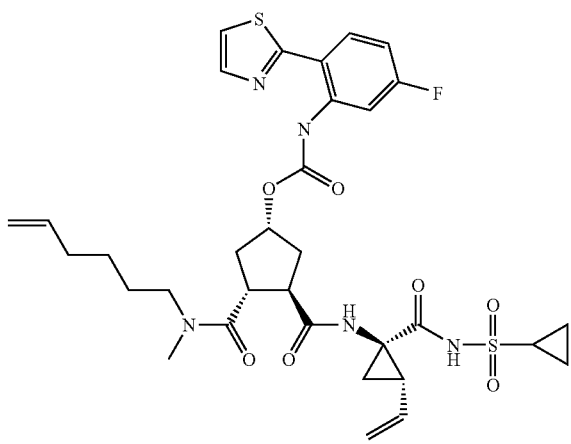

142

(5-Fluoro-2-thiazol-2-yl-phenyl)-carbamic acid 3-(1-cyclopropanesulfonylamino carbonyl-2-vinyl-cyclopropylcarbamoyl)-4-(hex-5-enyl-methyl-carbamoyl)-cyclo pentyl ester (168)

The title compound was prepared according to the procedure described in Example 17-1, except that 5-fluoro-2-thiazol-2-yl-phenylamine was used instead of 2-(5-ethyl-thiazol-2-yl)-5-trifluoromethyl-phenylamine. LC/MS (50-90% B in A): $t_R$=2.26 min, >90%, m/z (ESI$^+$)=702 (MH$^+$).

Example 79

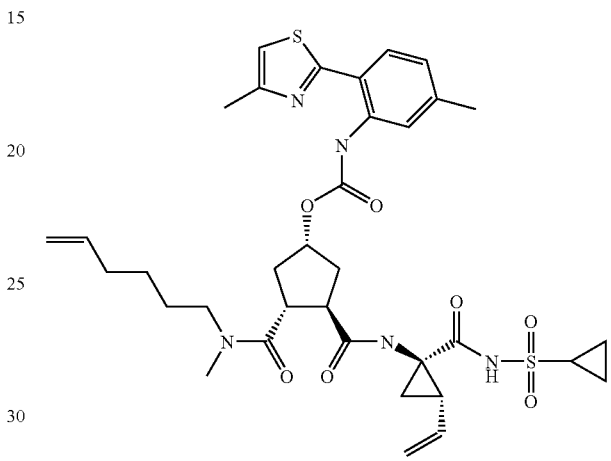

[5-Methyl-2-(4-methyl-thiazol-2-yl)-phenyl]-carbamic acid 3-(1-cyclopropane sulfonylaminocarbonyl-2-vinyl-cyclopropylcarbamoyl)-4-(hex-5-enyl-methyl-carbamoyl)-cyclopentyl ester (169)

The title compound was prepared according to the procedure described in Example 17-1, except that 5-methyl2-(4-methyl-thiazol-2-yl)-phenylamine was used instead of 2-(5-ethyl-thiazol-2-yl)-5-trifluoromethyl-phenylamine. LC/MS (50-90% B in A): $t_R$=2.56 min, >90%, m/z (ESI$^+$)=712 (MH$^+$).

Example 80

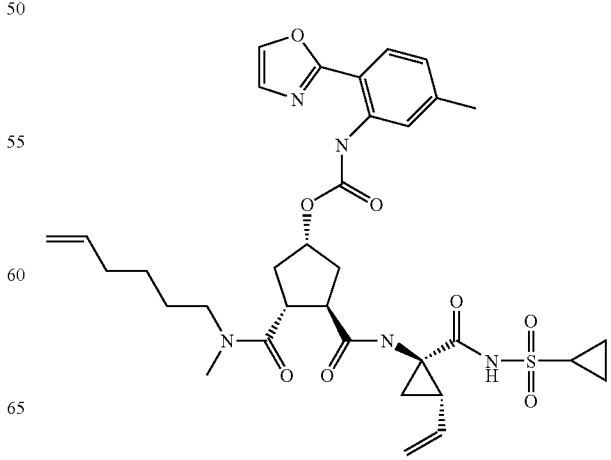

(5-Methyl-2-oxazol-2-yl-phenyl)-carbamic acid 3-(1-cyclopropanesulfonylamino carbonyl-2-vinyl-cyclopropylcarbamoyl)-4-(hex-5-enyl-methyl-carbamoyl)-cyclopentyl ester (170)

The title compound was prepared according to the procedure described in Example 17-1, except that 5-methyl-2-oxal-2-yl-phenylamine was used instead of 2-(5-ethyl-thiazol-2-yl)-5-trifluoromethyl-phenylamine. LC/MS (50-90% B in A): $t_R$=2.12 min, >90%, m/z (ESI$^+$)=682 (MH$^+$).

Example 81

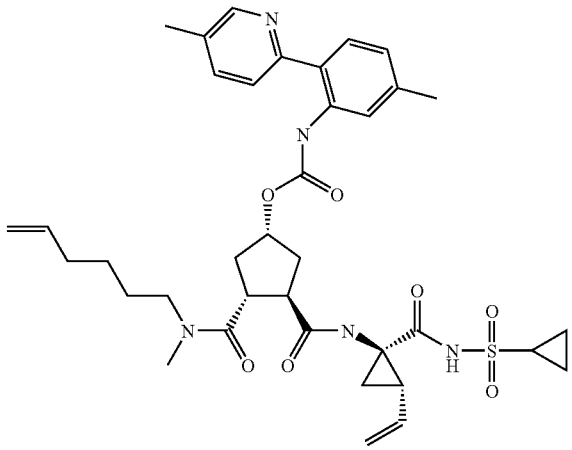

[5-Methyl-2-(5-methyl-pyridin-2-yl)-phenyl]-carbamic acid 3-(1-cyclopropane sulfonylaminocarbonyl-2-vinyl-cyclopropylcarbamoyl)-4-(hex-5-enyl-methyl-carbamoyl)-cyclopentyl ester (171)

The title compound was prepared according to the procedure described in Example 17-1, except that 5-methyl-2-(5-methyl-pyridin-2-yl)-phenylamine was used instead of 2-(5-ethyl-thiazol-2-yl)-5-trifluoromethyl-phenylamine. LC/MS (20-80% B in A): $t_R$=2.21 min, >90%, m/z (ESI$^+$)=706 (MH$^+$).

Example 82

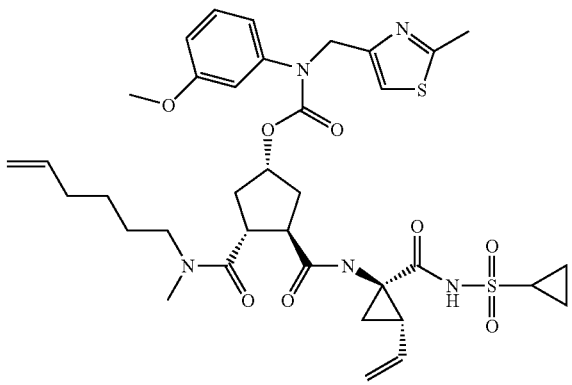

(3-Methoxy-phenyl)-(2-methyl-thiazol-4-ylmethyl)-carbamic acid 3-(1-cyclopropane sulfonylaminocarbonyl-2-vinyl-cyclopropylcarbamoyl)-4-(hex-5-enyl-methyl-carbamoyl)-cyclopentyl ester (172)

The title compound was prepared according to the procedure described in Example 17-1, except that (3-methoxyphenyl)-(2-methylthiazol-4-yl-methyl)-amine was used instead of 2-(5-ethyl-thiazol-2-yl)-5-trifluoromethyl-phenylamine. LC/MS (50-90% B in A): $t_R$=1.33 min, >90%, m/z (ESI$^+$)=742 (MH$^+$).

Example 83

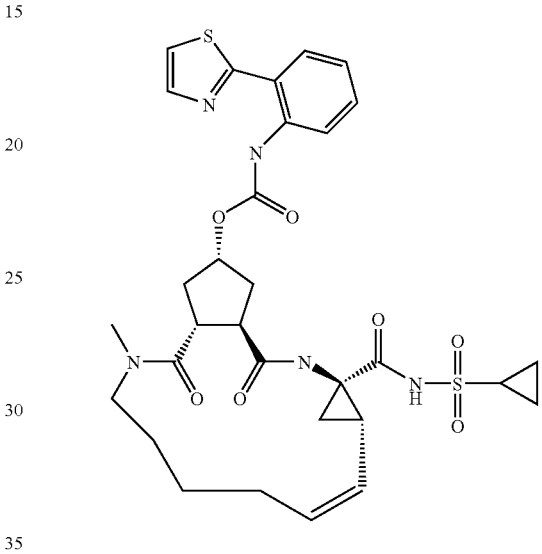

(2-Thiazol-2-yl-phenyl)-carbamic acid 4-cyclopropanesulfonylaminocarbonyl-13-methyl-2,14-dioxo-3,13-diaza-tricyclo[13.3.0.0*4,6*]octadec-7-en-17-yl ester (173)

The title compound was prepared according to the procedure described in Example 9-1, except that compound 165 was used instead of compound 10. LC/MS (50-90% B in A): $t_R$=1.64 min, >90%, m/z (ESI$^+$)=656 (MH$^+$).

Example 84

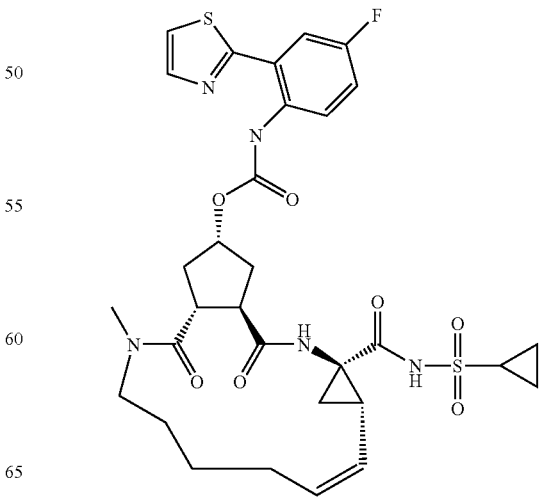

145

(4-Fluoro-2-thiazol-2-yl-phenyl)-carbamic acid 4-cyclopropanesulfonylamino carbonyl-13-methyl-2,14-dioxo-3,13-diaza-tricyclo[13.3.0.0*4,6*]octadec-17-yl ester (174)

The title compound was prepared according to the procedure described in Example 9-1, except that compound 166 was used instead of compound 10. LC/MS (50-90% B in A): $t_R$=1.73 min, 95%, m/z (ESI$^+$)=674 (MH$^+$).

Example 85

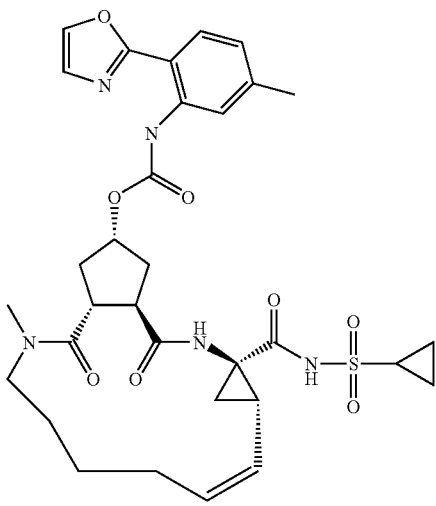

(4-Methyl-2-thiazol-2-yl-phenyl)-carbamic acid 4-cyclopropanesulfonylamino carbonyl-13-methyl-2,14-dioxo-3,13-diaza-tricyclo[13.3.0.0*4,6*]octadec-7-en-17-yl ester (175)

The title compound was prepared according to the procedure described in Example 9-1, except that compound 167 was used instead of compound 10. LC/MS (50-90% B in A): $t_R$=1.86 min, >95%, m/z (ESI$^+$)=670 (MH$^+$).

Example 86

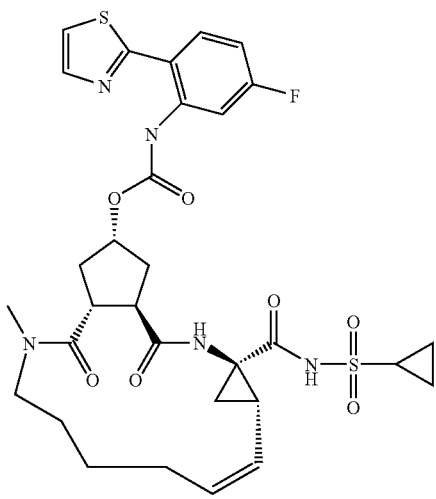

146

(5-Fluoro-2-thiazol-2-yl-phenyl)-carbamic acid 4-cyclopropanesulfonylamino carbonyl-13-methyl-2,14-dioxo-3,13-diaza-tricyclo[13.3.0.0*4,6*]octadec-7-en-17-yl ester (176)

The title compound was prepared according to the procedure described in Example 9-1, except that compound 168 was used instead of compound 10. LC/MS (50-90% B in A): $t_R$=1.82 min, >95%, m/z (ESI$^+$)=674 (MH$^+$).

Example 87

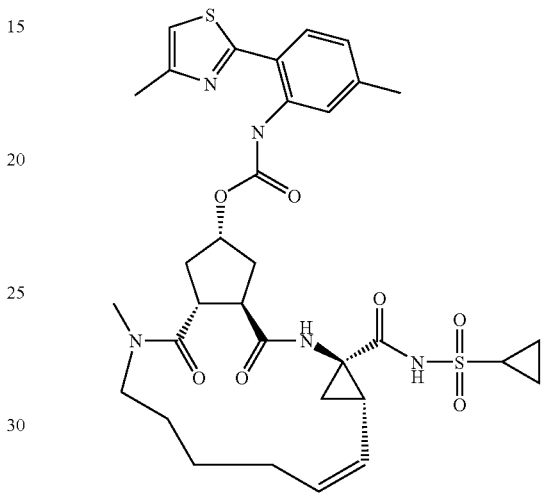

[5-Methyl-2-(4-methyl-thiazol-2-yl)-phenyl]-carbamic acid 4-cyclopropanesulfonyl aminocarbonyl-13-methyl-2,14-dioxo-3,13-diaza-tricyclo[13.3.0.0*4,6*]octadec-7-en-17-yl ester (177)

The title compound was prepared according to the procedure described in Example 9-1, except that compound 169 was used instead of compound 10. LC/MS (50-90% B in A): $t_R$=2.13 min, >95%, m/z (ESI$^+$)=684 (MH$^+$).

Example 88

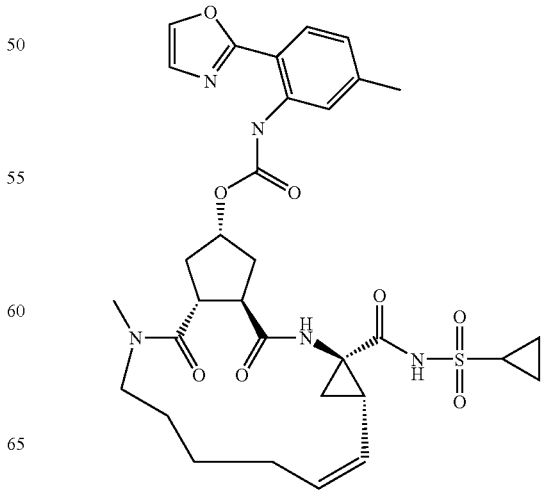

147

(5-Methyl-2-oxazol-2-yl-phenyl)-carbamic acid 4-cyclopropanesulfonylamino carbonyl-13-methyl-2,14-dioxo-3,13-diaza-tricyclo[13.3.0.0*4,6*]octadec-17-yl ester (178)

The title compound was prepared according to the procedure described in Example 9-1, except that compound 170 was used instead of compound 10. LC/MS (50-90% B in A): $t_R$=1.79 min, >90%, m/z (ESI$^+$)=654 (MH$^+$).

Example 89

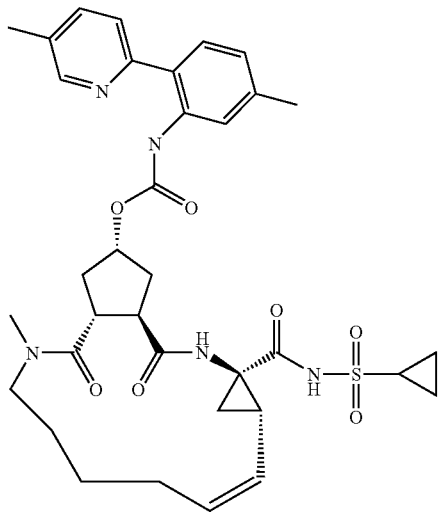

[5-Methyl-2-(5-methyl-pyridin-2-yl)-phenyl]-carbamic acid 4-cyclopropanesulfonyl aminocarbonyl-13-methyl-2,14-dioxo-3,13-diaza-tricyclo [13.3.0.0*4,6*]octadec-7-en-17-yl ester (179)

The title compound was prepared according to the procedure described in Example 9-1, except that compound 171 was used instead of compound 10. LC/MS (20-80% B in A): $t_R$=2.03 min, >95%, m/z (ESI$^+$)=678 (MH$^+$).

Example 90

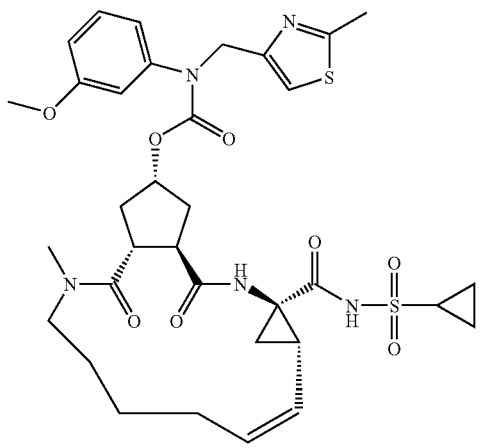

148

(3-Methoxy-phenyl)-(2-methyl-thiazol-4-ylmethyl)-carbamic acid 4-cyclopropane sulfonylaminocarbonyl-13-methyl-2,14-dioxo-3,13-diaza-tricyclo [13.3.0.0*4,6*]octadec-7-en-17-yl ester (180)

The title compound was prepared according to the procedure described in Example 9-1, except that compound 172 was used instead of compound 10. LC/MS (20-80% B in A): $t_R$=2.49 min, >95%, m/z (ESI$^+$)=714 (MH$^+$).

Example 91

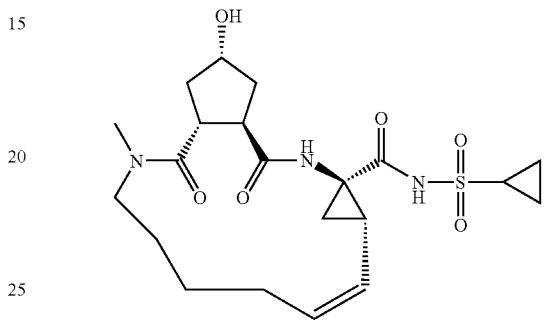

Cyclopropanesulfonic acid (17-hydroxy-13-methyl-2,14-dioxo-3,13-diaza-tricyclo [13.3.0.0*4,6*]octadec-7-ene-4-carbonyl)-amide, (120)

Compound 8 (150 mg, 310 umol) was dissolved in DCE (dried over mol sieves, N$_2$-gassed) (150 mL) and Hoyveda-Grubbs 2$^{nd}$ generation cat. (29.5 mg, 47 umol) was added. The flask was purged with N$_2$(g) and the reaction refluxed for 3 hours under N$_2$(g) atmosphere. The solvent was removed in vacuo and the residue purified by flash chromatography (Silica; DCM:MeOH) to afford the title compound (108 mg, 77%). LC/MS (20-80% B in A): $t_R$=1.79 min, >95%, m/z (ESI)=454 (MH$^+$).

Example 92

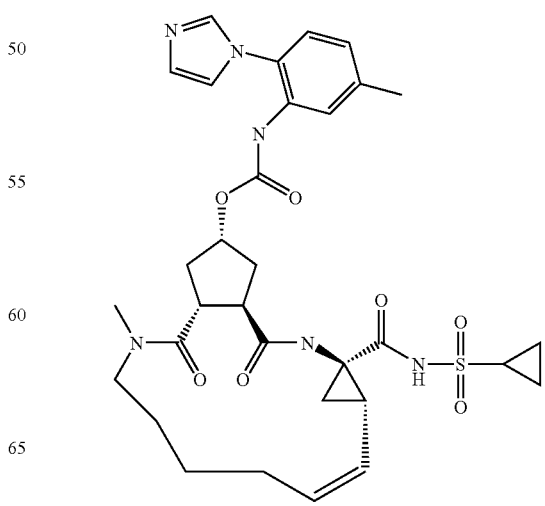

149

(2-Imidazol-1-yl-5-methyl-phenyl)-carbamic acid 4-cyclopropanesulfonylamino carbonyl-13-methyl-2, 14-dioxo-3,13-diaza-tricyclo[13.3.0.0*4,6*]octadec-7-yl ester (181)

Compound 120 (25 mg, 55 umol) was dissolved in dried DCM (1.5 mL). To this solution was added solid NaHCO$_3$ (14 mg, 165 umol) and phosgene (1.9 M in toluene, 435 uL, 825 umol). The mixture was stirred vigorously for 3 h to afford the intermediate chloroformate. LC/MS (Method F): $t_R$=2.32 min, m/z (ESI$^+$)=516 (MH$^+$). The solvent was removed in vacuo and the residue was co-evaporated with DCM to remove any residual phosgene. The afforded chloroformate was subsequently re-dissolved in dried DCE (2 ml) and 7 (19 mg, 110 μmol) was added followed by the addition of solid K$_2$CO$_3$ (20 mg, 149 μmol) and powdered 4 Å mol. sieves (1 spatula). The mixture was heated to 100° C. for 45 min, after which time LC/MS analysis showed no remaining chloroformate. The reaction was filtered and the filtrate concentrated in vacuo to afford a crude which was purified by preparative LC/MS to yield the title compound. LC/MS (30-80% B in A): $t_R$=1.82 min, >90%, m/z (ESI$^+$)=653 (MH$^+$).

Example 93

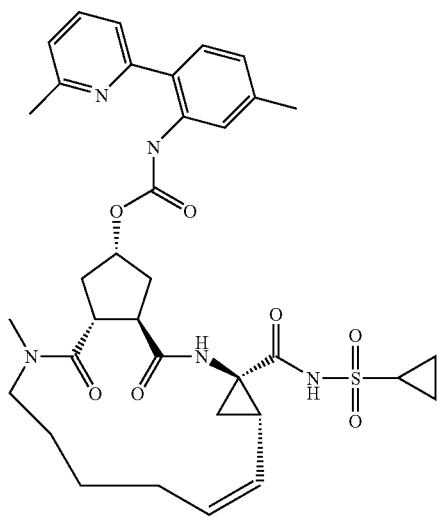

150

[5-Methyl-2-(6-methyl-pyridin-2-yl)-phenyl]-carbamic acid 4-cyclopropanesulfonyl aminocarbonyl-13-methyl-2,14-dioxo-3,13-diaza-tricyclo [13.3.0.0*4,6*]octadec-7-en-17-yl ester (182)

5-Methyl-2-(6-methylpyridin-2-yl)-phenylamine was coupled to compound 120 according to the procedure described in Example 6-1, which gave the title compound. LC/MS (20-80% B in A): $t_R$=2.05 min, 95%, m/z (ESI$^+$)=678 (MH$^+$).

Example 94

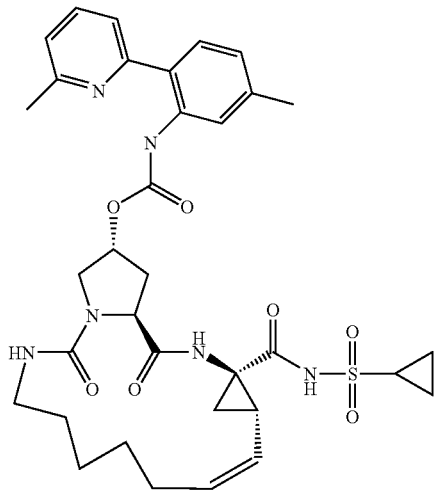

[5-Methyl-2-(6-methyl-pyridin-2-yl)-phenyl]-carbamic acid 4-cyclopropanesulfonyl aminocarbonyl-2,15-dioxo-3,14,16-triaza-tricyclo[14.3.0.0*4,6*] nonadec-7-en-18-yl ester (183)

Compound 140 (Ex. 50, 25 mg, 55 μmol) was dissolved in dried DCM (2 mL). To this solution was added solid NaHCO$_3$ (14 mg, 165 μmol) and phosgene (1.9 M in toluene, 868 μL, 1.65 mmol). The mixture was stirred for 48 h to afford the intermediate chloroformate. LC/MS (Method F): $t_R$=2.32 min, m/z (ESI$^+$)=516 (MH$^+$). The solvent was removed in vacuo and the residue was co-evaporated with DCM to remove any residual phosgene. The afforded chloroformate was subsequently re-dissolved in dried DCE (2 ml) and 5-methyl-2-(6-methylpyridin-2-yl)-phenylamine (16 mg, 83 μmol) was added followed by the addition of solid K$_2$CO$_3$ (15 mg, 110 μmol) and powdered 4 Å mol. sieves (1 spatula). The mixture was heated to 100° C. for 45 min, after which time LC/MS analysis showed no remaining chloroformate. The reaction was filtered and the filtrate concentrated in vacuo to afford a crude which was purified by preparative LC/MS to yield the title compound. LC/MS (20-80% B in A): $t_R$=2.02 min, >95%, m/z (ESI$^+$)=679 (MH$^+$).

Example 95

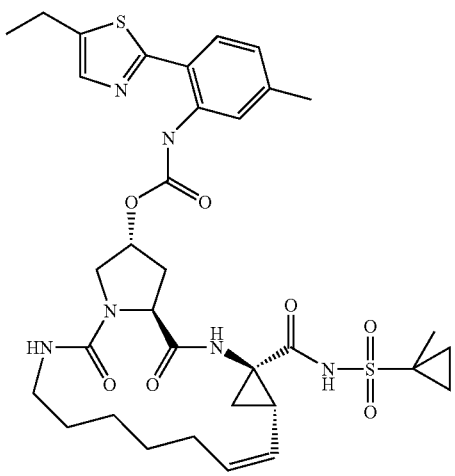

[2-(5-Ethyl-thiazol-2-yl)-5-methyl-phenyl]-carbamic acid 4-(1-methyl-cyclopropane sulfonylaminocarbonyl)-2,15-dioxo-3,14,16-triaza-tricyclo[14.3.0.0*4, 6*]nonadec-7-en-18-yl ester (184)

The title compound was prepared according to the procedure described in Example 94, except that compound 141 was used instead of compound 140 and 2-(5-ethyl-thiazol-2-yl)-5-methyl-phenylamine was used instead of 5-methyl-2-(6-methylpyridin-2-yl)-phenylamine. LC/MS (50-100% B in A): $t_R$=2.17 min, 95%, m/z (ESI$^+$)=713 (MH$^+$).

Example 96

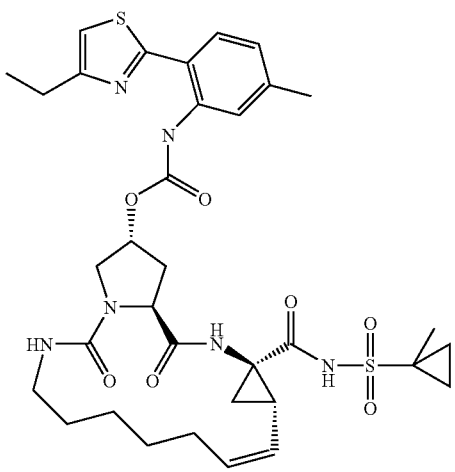

[2-(4-Ethyl-thiazol-2-yl)-5-methyl-phenyl]-carbamic acid 4-(1-methyl-cyclopropane sulfonylaminocarbonyl)-2,15-dioxo-3,14,16-triaza-tricyclo[14.3.0.0*4, 6*]nonadec-7-en-18-yl ester (185)

The title compound was prepared according to the procedure described in Example 94, except that compound 141 was used instead of compound 140 and 2-(4-ethyl-thiazol-2-yl)-5-methyl-phenylamine was used instead of 5-methyl-2-(6-methylpyridin-2-yl)-phenylamine. LC/MS (50-100% B in A): $t_R$=2.09 min, 95%, m/z (ESI$^+$)=713 (MH$^+$).

Example 97

Synthesis of crystalline cyclopentane exemplified by synthesis of 3-Oxo-2-oxa-bicyclo[2.2.1]heptane-5-carboxylic acid tert-butyl ester (186).

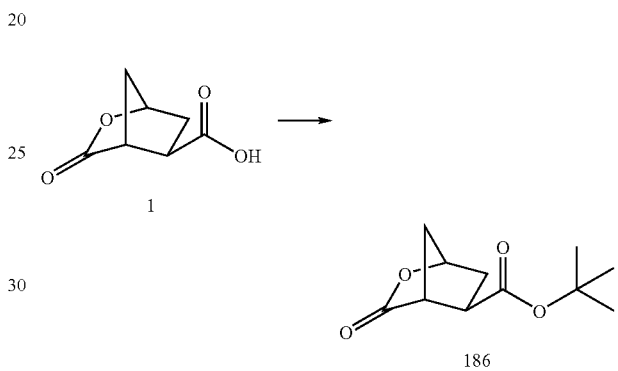

DMAP (14 mg, 0.115 mmol) and Boc$_2$O (252 mg, 1.44 mmol) was added to a stirred solution of 1 (180 mg, 1.15 mmol) in 2 mL CH$_2$Cl$_2$ under inert argon atmosphere at 0° C. The reaction was allowed to warm to room temperature and was stirred overnight. The reaction mixture was concentrated and the crude product was purified by flash column chromatography (toluene/ethyl acetate gradient 15:1, 9:1, 6:1, 4:1, 2:1) which gave the title compound (124 mg, 51%) as white crystals. $^1$H-NMR (300 MHz, CD$_3$OD) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, CD$_3$OD) δ 27.1, 33.0, 37.7, 40.8, 46.1, 81.1, 81.6, 172.0, 177.7.

Alternative method for the preparation of compound 186:

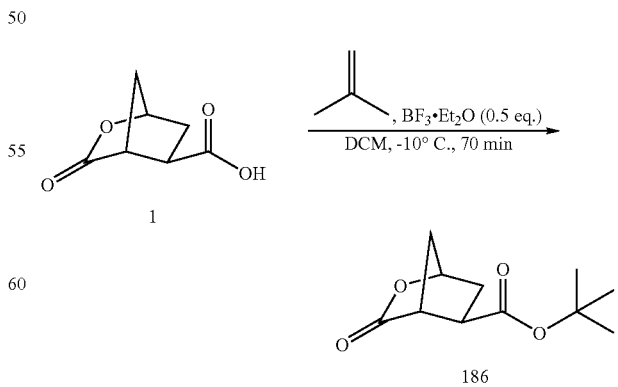

Compound 1 (13.9 g, 89 mmol) was dissolved in dichloromethane (200 ml) and then cooled to approximately −10°

C. under nitrogen. Isobutylene was then bubbled into the solution until the total volume had increased to approximately 250 ml which gave a turbid solution. $BF_3$.diethyl ether (5.6 ml, 44.5 mmol, 0.5 eq.) was added and the reaction mixture was kept at approximately −10° C. under nitrogen. After 10 min, a clear solution was obtained. The reaction was monitored by TLC (ethyl acetate/Toluene 3:2 acidified with a few drops of acetic acid and hexane/ethyl acetate 4:1, staining with basic permanganate solution). At 70 min only traces of compound 1 remained and aqueous saturated $NaHCO_3$ (200 ml) was added to the reaction mixture, which was then stirred vigorously for 10 min. The organic layer was washed with saturated $NaHCO_3$ (3×200 ml) and brine (1×150 ml), then dried with sodium sulfite, filtered and the residue was evaporated to an oily residue. Upon addition of hexane to the residue, the product precipitated. Addition of more hexane and heating to reflux gave a clear solution from which the product crystallized. The crystals were collected by filtration and were washed with hexane (rt), then air-dried for 72 h giving colourless needles (12.45 g, 58.7 mmol, 66%).

Example 98

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion ($neo^R$, neomycine phosphotransferase). The construct is bordered by 5' and 3' NTRs (non-translated regions) from HCV type 1b. Continued culture of the replicon cells in the presence of G418 ($neo^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay was to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-$NH_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 μM NS4A cofactor and inhibitor at 30° C. for 10 min, whereupon the reaction was initiated by addition of 0.5 μM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures [Liu, Analytical Biochemistry, 1999, vol. 267, pp. 331-335]. Ki values were estimated by non-linear regression analysis (GraFit, Erithacus Software, Staines, MX, UK), using a model for competitive inhibition and a fixed value for Km (0.15 μM). A minimum of two replicates was performed for all measurements.

The following Table 1 and Table 2 lists compounds that were prepared according to any one of the above examples. The activities of the compounds tested are also depicted in these tables.

TABLE 1
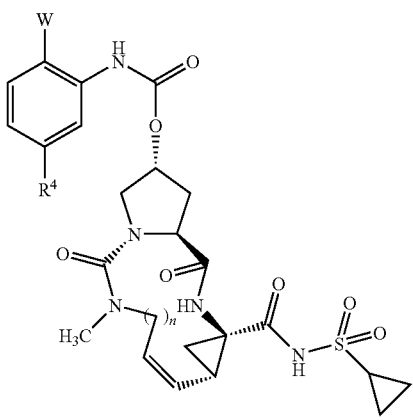
(I-f)
| Compound nr. | R⁴ | W | n | EC₅₀ (μM) Replicon assay | Ki (nM) Enzymatic assay |
|---|---|---|---|---|---|
| 1 | —CF₃ | piperidin-1-yl | 4 | 4.442 | 8 |
| 2 | H | 5-methylfuran-2-yl | 4 | 5.653 | 31.6 |
| 3 | H | thiophen-3-yl | 4 | 10 | 1281 |
| 4 | H | phenyl | 4 | 10 | 517 |
| 5 | H | —C(=O)OEt | 4 | 0.269 | 20 |

TABLE 2

(I-g)

| Compound nr. | R⁴ | W | n | EC$_{50}$ (μM) Replicon assay | Ki (nM) Enzymatic assay |
|---|---|---|---|---|---|
| 6 | —CF$_3$ | pyrazolyl-CH$_3$ | 4 | $7.06 \times 10^{-2}$ | 0.5 |
| 7 | H | piperidinyl | 4 | 0.111 | 5 |
| 8 | —CF$_3$ | pyrazolyl | 4 | 0.234 | — |
| 9 | F | pyrazolyl-CH$_3$ | 4 | 0.237 | 1.4 |
| 10 | F | pyrazolyl | 4 | 0.665 | — |
| 11 | —CF$_3$ | piperidinyl | 4 | 1.004 | — |
| 12 | pyrazolyl | pyrazolyl | 4 | 1.508 | 9 |

TABLE 2-continued
(I-g)
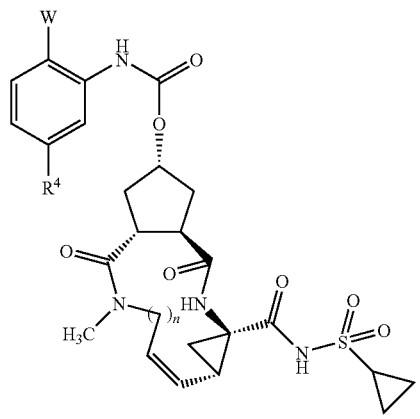
| Compound nr. | R⁴ | W | n | EC$_{50}$ (μM) Replicon assay | Ki (nM) Enzymatic assay |
|---|---|---|---|---|---|
| 13 | —CF$_3$ | 5-methyl-pyrazol-1-yl | 4 | 7.581 | 38 |
| 14 | F | 5-methyl-pyrazol-1-yl | 4 | >10 | — |
| 15 | H | phenyl (α-methyl) | 4 | 4.375 | 45 |
| 16 | —CF$_3$ | 4-methyl-thiazol-2-yl | 4 | 0.0074 | 0.1 |
| 17 | —CF$_3$ | 5-methyl-thiazol-2-yl | 4 | 0.0032 | 1.7 |
| 18 | —CF$_3$ | 4,5-dimethyl-thiazol-2-yl | 4 | 0.001 | 1.7 |

TABLE 2-continued (I-g)

| Compound nr. | R⁴ | W | n | EC$_{50}$ (µM) Replicon assay | Ki (nM) Enzymatic assay |
|---|---|---|---|---|---|
| 19 | —CF$_3$ | thiazole-ethyl | 4 | 0.016 | — |
| 20 | —CF$_3$ | thiazole-isopropyl | 4 | 0.039 | 1.9 |
| 21 | —CF$_3$ | thiazole-tert-butyl | 4 | 0.094 | — |
| 22 | —CF$_3$ | thiazole-ethyl | 4 | 0.0032 | — |
| 23 | —CH$_3$ | thiazole-ethyl | 4 | 0.0053 | — |

TABLE 2-continued

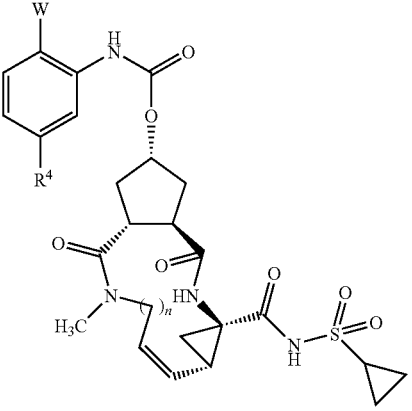

(I-g)

| Compound nr. | $R^4$ | W | n | $EC_{50}$ (μM) Replicon assay | $K_i$ (nM) Enzymatic assay |
|---|---|---|---|---|---|
| 24 | —CH$_3$ | 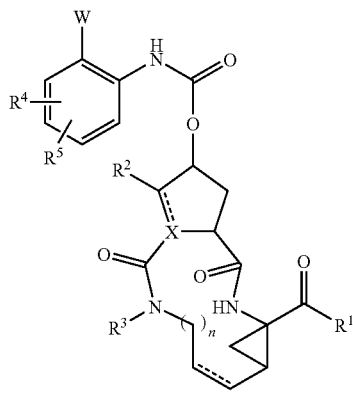 | 4 | 0.0032 | — |
| 25 | —H | —F | 4 | 8.401 | 51 |
| 26 | —H | —C(=O)OEt | 4 | 4.92 × 10$^{-2}$ | — |

The invention claimed is:

1. A compound having the formula (I)

an N-oxide, salt, or stereoisomer thereof, wherein
each dashed line (represented by - - - - -) represents an optional double bond;
X is N, CH and where X bears a double bond it is C;
$R^1$ is —OR$^6$, —NH—SO$_2$R$^7$;
$R^2$ is hydrogen, and where X is C or CH, $R^2$ may also be C$_{1-6}$alkyl;
$R^3$ is hydrogen, C$_{1-6}$alkyl, C$_{1-6}$alkoxyC$_{1-6}$alkyl, or C$_{3-7}$cycloalkyl;
n is 3, 4, 5, or 6;
$R^4$ and $R^5$ independently from one another are hydrogen, halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, C$_{1-6}$alkoxy-carbonyl, amino, azido, mercapto, C$_{1-6}$alkylthio, polyhaloC$_{1-6}$alkyl, aryl or Het;
W is aryl or Het;
$R^6$ is hydrogen; aryl; Het; C$_{3-7}$cycloalkyl optionally substituted with C$_{1-6}$alkyl; or C$_{1-6}$alkyl optionally substituted with C$_{3-7}$cycloalkyl, aryl or with Het;
$R^7$ is aryl; Het; C$_{3-7}$cycloalkyl optionally substituted with C$_{1-6}$alkyl; or C$_{1-6}$alkyl optionally substituted with C$_{3-7}$cycloalkyl, aryl or with Het;
aryl as a group or part of a group is phenyl or naphthyl, each of which may be optionally substituted with one, two or three substituents selected from halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, polyhaloC$_{1-6}$alkyl, polyhalo C$_{1-6}$alkoxy, C$_{3-7}$cycloalkyl, pyrrolidinyl, piperidinyl, piperazinyl, 4-C$_{1-6}$alkyl-piperazinyl, 4-C$_{1-6}$alkylcarbonyl-piperazinyl, and morpholinyl; wherein the morpholinyl and piperidinyl groups may be optionally substituted with one or with two C$_{1-6}$alkyl radicals;
Het as a group or part of a group is a 5 or 6 membered saturated, partially unsaturated or completely unsaturated heterocyclic ring containing 1 to 4 heteroatoms each independently selected from nitrogen, oxygen and sulfur, and being optionally substituted with one, two or three substituents each independently selected from the group consisting of halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or di-C$_{1-6}$alkylamino, azido, mercapto, polyhaloC$_{1-6}$alkyl, polyhaloC$_{1-6}$alkoxy, C$_{3-7}$cycloalkyl, pyrrolidinyl, piperidinyl, piperazinyl, 4-$C_{1-6}$alkyl-piperazinyl, 4-$C_{1-6}$alkylcarbonyl-piperazinyl, and morpholinyl; wherein the morpholinyl and piperidinyl groups may be optionally substituted with one or with two $C_{1-6}$alkyl radicals.

2. A compound according to claim 1, wherein the compound has the formula (I-c), (I-d), or (I-e):

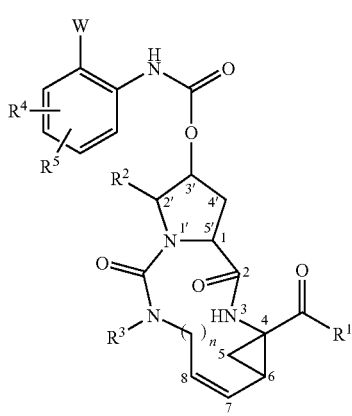

(I-c)

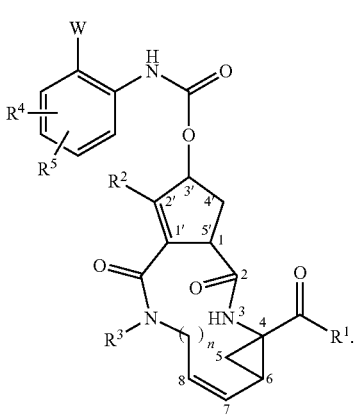

(I-d)

(I-e)

3. A compound according to claim 1, wherein W is phenyl, naphth-1-yl, naphth-2-yl, pyrrol-1-yl, 3-pyridyl, pyrimidin-4-yl, pyridazin-3-yl, pyridazin-2-yl, 6-oxo-pyridazin-1-yl, 1,2,3-triazol-2-yl, 1,2,4-triazol-3-yl, tetrazol-1-yl, tetrazol-2-yl, pyrazol-1-yl, pyrazol-3-yl, imidazol-1-yl, imidazol-2-yl, thiazol-2-yl, pyrrolidin-1-yl, piperidin-1-yl, furan-2-yl, thien-3-yl, morpholin-4-yl; all optionally substituted with one or two substituents selected from $C_{1-6}$alkyl, polyhalo$C_{1-6}$alkyl, or $C_{1-6}$alkoxycarbonyl.

4. A compound according to claim 1, wherein $R^4$ and $R^5$ independently from one another are hydrogen, halo, nitro, carboxyl, methyl, ethyl, isopropyl, tert-butyl, methoxy, ethoxy, isopropoxy, tert-butoxy, methylcarbonyl, ethylcarbonyl, isopropylcarbonyl, tert-butyl-carbonyl, methoxycarbonyl, ethoxycarbonyl, isopropoxycarbonyl, tert-butoxycarbonyl, methylthio, ethylthio, isopropylthio, tert-butylthio, trifluoromethyl, or cyano.

5. A compound according to claim 1, wherein
(a) $R^1$ is —$OR^6$, wherein $R^6$ is $C_{1-6}$alkyl or hydrogen;
(b) $R^1$ is —$NHS(=O)_2R^7$, wherein $R^7$ is methyl, cyclopropyl, or phenyl; or
(c) $R^1$ is —$NHS(=O)_2R^7$, wherein $R^7$ is 1-methylcyclopropyl.

6. A compound according to claim 1 other than an N-oxide, or salt.

7. A combination comprising
(a) a compound as defined in claim 1 or a pharmaceutically acceptable salt thereof; and
(b) ritonavir, or a pharmaceutically acceptable salt thereof.

8. A pharmaceutical composition comprising a carrier, and as active ingredient an anti-HCV effective amount of a compound of claim 1.

9. A method of inhibiting HCV replication in a warm-blooded animal said method comprising the administration of an effective amount of a compound according to claim 1 or an effective amount of each component of the combination according to claim 7.

10. A process for preparing a compound of claim 1, wherein said process comprises:
(a) preparing a compound of formula (I) wherein the bond between $C_7$ and $C_8$ is a double bond, which is a compound of formula (I-i), by forming a double bond between $C_7$ and $C_8$, in particular via an olefin metathesis reaction, with concomitant cyclization to the macrocycle as outlined in the following reaction scheme:

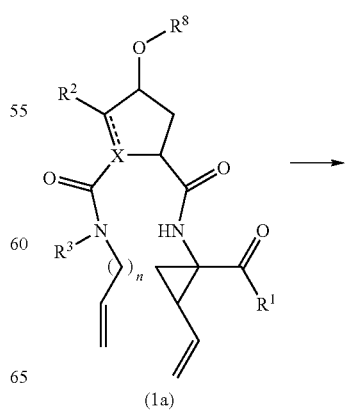

(Ia)

-continued

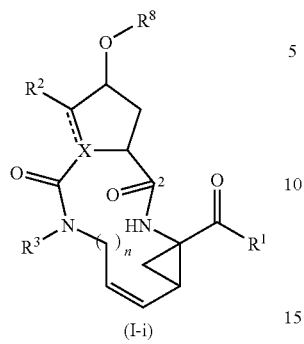
(I-i)

wherein in the above and following reaction schemes R⁸ represents a radical

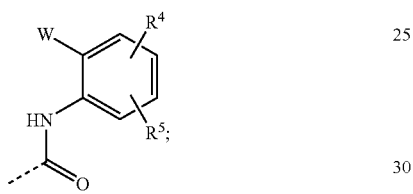

(b) converting a compound of formula (I-i) to a compound of formula (I) wherein the link between C7 and C8 in the macrocycle is a single bond, i.e. a compound of formula (I-j):

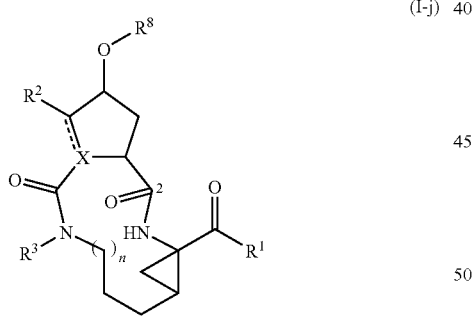
(I-j)

by a reduction of the C7-C8 double bond in the compounds of formula (I-j);

(c) preparing a compound of formula (I) wherein $R^1$ represents —NHSO₂R⁷, said compounds being represented by formula (I-k-1), by forming an amide bond between a intermediate (2a) and an sulfonylamine (2b), or preparing a compound of formula (I) wherein $R^1$ represents —OR⁶, i.e. a compound (I-k-2), by forming an ester bond between an intermediate (2a) and an alcohol (2c) as outlined in the following scheme wherein G represents a group:

(a)

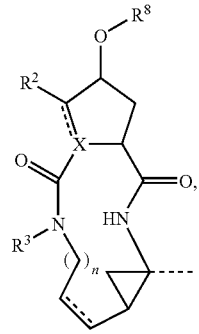

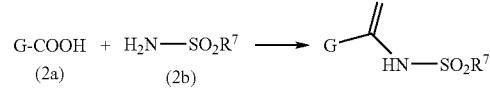

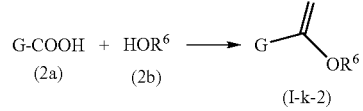

(d) preparing a compound of formula (I) wherein $R^3$ is hydrogen, said compound being represented by (I-l), from a corresponding nitrogen-protected intermediate (3a), wherein PG represents a nitrogen protecting group:

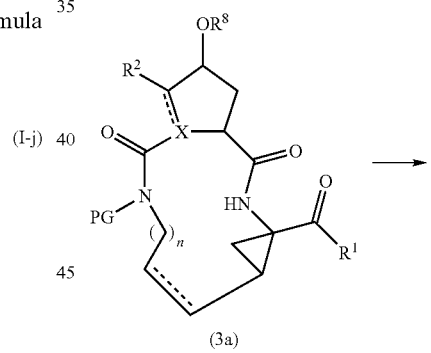
(3a)

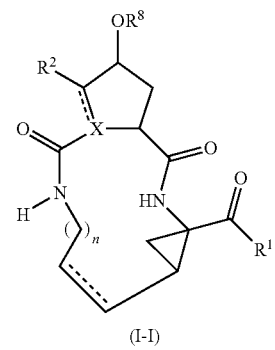
(I-l)

(e) reacting an intermediate (4a) with an aniline (4b) in the presence of a carbamate forming reagent as outlined in the following reaction scheme:

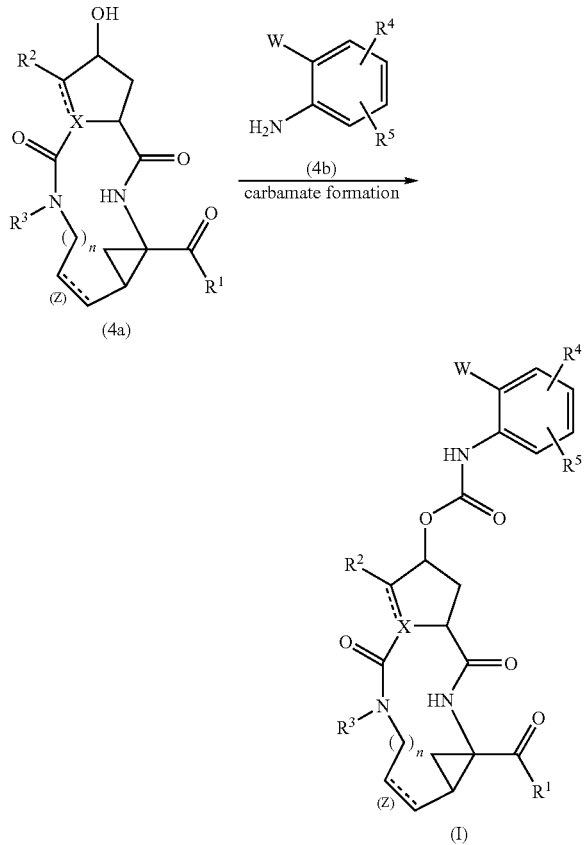

(f) converting compounds of formula (I) into each other by a functional group transformation reaction; or
(g) preparing a salt form by reacting the free form of a compound of formula (I) with an acid or a base.

11. A compound having the formula

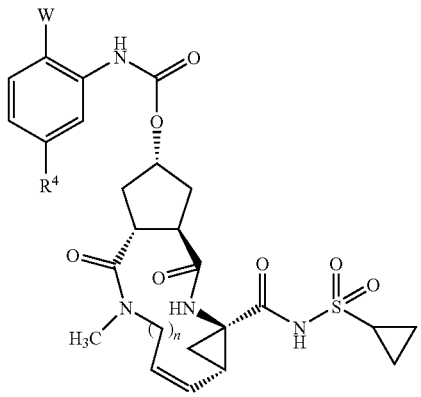

an N-oxide, salt, or stereoisomer thereof;
wherein each dashed line represents an optional double bond,
W is

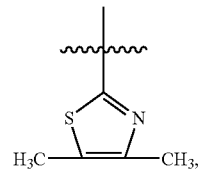

and
$R^4$ is —$CF_3$.

12. A pharmaceutical composition comprising a carrier, and as active ingredient an anti-HCV effective amount of a combination according to claim 7.